United States Patent
Klotz et al.

(10) Patent No.: US 12,138,296 B2
(45) Date of Patent: *Nov. 12, 2024

(54) FORMULATIONS FOR BOVINE GRANULOCYTE COLONY STIMULATING FACTOR AND VARIANTS THEREOF

(71) Applicant: ELANCO US INC., Greenfield, IN (US)

(72) Inventors: Alan Voskamp Klotz, Indianapolis, IN (US); Catherine Ngan Kha, Raleigh, NC (US); Juan Davagnino, Durham, NC (US)

(73) Assignee: ELANCO US INC., Greenfield, IN (US)

( * ) Notice: Subject to any disclaimer, the term of this patent is extended or adjusted under 35 U.S.C. 154(b) by 249 days.

This patent is subject to a terminal disclaimer.

(21) Appl. No.: 17/591,553

(22) Filed: Feb. 2, 2022

(65) Prior Publication Data

US 2022/0152155 A1 May 19, 2022

Related U.S. Application Data

(63) Continuation of application No. 13/239,493, filed on Sep. 22, 2011, now Pat. No. 11,273,202.

(60) Provisional application No. 61/385,629, filed on Sep. 23, 2010.

(51) Int. Cl.
 *C07K 14/535* (2006.01)
 *A61K 38/19* (2006.01)

(52) U.S. Cl.
 CPC .......... *A61K 38/193* (2013.01); *C07K 14/535* (2013.01)

(58) Field of Classification Search
 CPC .................................................. C07K 14/535
 See application file for complete search history.

(56) References Cited

U.S. PATENT DOCUMENTS

| | | |
|---|---|---|
| 3,773,919 A | 11/1973 | Boswell et al. |
| 4,289,872 A | 9/1981 | Denkewalter et al. |
| 4,401,666 A | 8/1983 | Wedig et al. |
| 4,412,989 A | 11/1983 | Iwashita et al. |
| 4,414,148 A | 11/1983 | Jansen et al. |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | DeBoer |
| 4,569,789 A | 2/1986 | Blattler et al. |
| 4,619,794 A | 10/1986 | Hauser |
| 4,659,839 A | 4/1987 | Nicolotti et al. |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,810,643 A | 3/1989 | Souza |
| 4,820,352 A | 4/1989 | Riedhammer et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,902,502 A | 2/1990 | Nitecki et al. |
| 4,904,584 A | 2/1990 | Shaw |
| 4,929,555 A | 5/1990 | Cregg et al. |
| 4,968,618 A | 11/1990 | Young |
| 4,999,291 A | 3/1991 | Souza |
| 5,021,234 A | 6/1991 | Ehrenfeld |
| 5,043,156 A | 8/1991 | Matsumoto et al. |
| 5,047,335 A | 9/1991 | Paulson et al. |
| 5,089,398 A | 2/1992 | Rosenberg et al. |
| 5,122,614 A | 6/1992 | Zalipsky |
| 5,162,601 A | 11/1992 | Slightom |
| 5,202,117 A | 4/1993 | Tsuji et al. |
| 5,218,092 A | 6/1993 | Sasaki et al. |
| 5,229,490 A | 7/1993 | Tam |
| 5,231,178 A | 7/1993 | Holtz et al. |
| 5,219,564 A | 8/1993 | Zalipsky et al. |
| 5,252,714 A | 10/1993 | Harris et al. |
| 5,281,698 A | 1/1994 | Nitecki |
| 5,290,686 A | 3/1994 | Kendal et al. |
| 5,320,840 A | 6/1994 | Camble et al. |
| 5,324,639 A | 6/1994 | Brierley et al. |

(Continued)

FOREIGN PATENT DOCUMENTS

| | | |
|---|---|---|
| DE | 3218121 A1 | 11/1983 |
| DE | 4242863 | 6/1994 |

(Continued)

OTHER PUBLICATIONS

Nicola, "Why Do Hemopoietic Growth Factor Receptors Interact with Each Other?", Immunol. Today (1987) 8 (5): 134-140.

Offord, "Protein engineering by chemical means?", Protein Eng., (1987) 1(3):151-157.

Oh-eda et al., "O-lin ked sugar chain of human granulocyte colony-stimulating factor protects it against polymerization and denaturation allowing it to retain its biological activity", J. Biol. Chem. (1990) 265(20): 11432-11435.

Ohno et al., "Co-Expression of Yeast Amber Suppressor tRNATyr and Tyrosyl-tRNA Synthetase in *Escherichia coli*: Possibility to Expand the Genetic Code", J. Biochem. (1998) 124:1065-1068.

Okkels, "A URA3-promoter deletion in a pYES vector increases the expression level of a fungal lipase in *Saccharomyces cerevisiae*", Ann. New York Aced. Sci. (1996) 782:202-207.

(Continued)

*Primary Examiner* — Prema M Mertz
(74) *Attorney, Agent, or Firm* — Barnes & Thornburg LLP

(57) ABSTRACT

This invention provides stable aqueous formulations comprising a bG-CSF polypeptide or a variant thereof, a buffer substance, and an excipient, wherein said formulation is substantially free of polyoxyethylene (20) sorbitan monolaurate. The invention also provides methods of using, a lyophilized or powdered form of, and processes for, preparing the formulation.

14 Claims, No Drawings

Specification includes a Sequence Listing.

(56) References Cited

U.S. PATENT DOCUMENTS

| | | |
|---|---|---|
| 5,324,844 A | 6/1994 | Zalipsky |
| 5,382,657 A | 1/1995 | Karasiewicz et al. |
| 5,416,195 A | 5/1995 | Camble et al. |
| 5,448,090 A | 8/1995 | Harris |
| 5,468,478 A | 11/1995 | Saifer et al. |
| 5,473,034 A | 12/1995 | Yasui et al. |
| 5,478,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,536,495 A | 7/1996 | Foster |
| 5,559,213 A | 9/1996 | Hakimi et al. |
| 5,571,709 A | 11/1996 | Devauchelle et al. |
| 5,580,723 A | 12/1996 | Wells et al. |
| 5,580,755 A | 12/1996 | Souza |
| 5,582,823 A | 12/1996 | Souza |
| 5,583,023 A | 12/1996 | Cerutti et al. |
| 5,602,034 A | 2/1997 | Tekamp-Olson |
| 5,605,827 A | 2/1997 | Jackwood et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,665,863 A | 9/1997 | Yeh |
| 5,672,662 A | 9/1997 | Harris et al. |
| 5,674,706 A | 10/1997 | Shuster |
| 5,681,720 A | 10/1997 | Kuga et al. |
| 5,718,893 A | 2/1998 | Oster |
| RE35,749 E | 3/1998 | Rosenberg et al. |
| 5,736,625 A | 4/1998 | Callstrom et al. |
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,883 A | 6/1998 | Ballance et al. |
| 5,766,885 A | 6/1998 | Carrington et al. |
| 5,773,569 A | 6/1998 | Wrighton et al. |
| 5,773,581 A | 6/1998 | Camble et al. |
| 5,776,895 A | 7/1998 | Alber et al. |
| 5,790,421 A | 8/1998 | Osslund |
| 5,795,968 A | 8/1998 | Kuga et al. |
| 5,808,096 A | 9/1998 | Zalipsky |
| 5,811,301 A | 9/1998 | Cameron |
| 5,824,778 A | 10/1998 | Ishikawa et al. |
| 5,824,784 A | 10/1998 | Kinstler et al. |
| 5,830,705 A | 11/1998 | Souza |
| 5,830,851 A | 11/1998 | Wrighton et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,849,883 A | 12/1998 | Boone et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,900,461 A | 5/1999 | Harris |
| 5,919,443 A | 7/1999 | Michaelis |
| 5,919,757 A | 7/1999 | Michaelis et al. |
| 5,932,462 A | 8/1999 | Harris et al. |
| 5,939,285 A | 8/1999 | Devauchelle et al. |
| 5,965,393 A | 10/1999 | Hasnain et al. |
| 5,980,948 A | 11/1999 | Goedemoed et al. |
| 5,985,265 A | 11/1999 | Kinstler et al. |
| 5,986,047 A | 11/1999 | Wrighton et al. |
| 5,989,868 A | 11/1999 | Harrison et al. |
| 5,990,237 A | 11/1999 | Bentley et al. |
| 5,998,595 A | 12/1999 | Kusumoto et al. |
| 6,001,800 A | 12/1999 | Mehta |
| 6,004,548 A | 12/1999 | Souza |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,017,876 A | 1/2000 | Gegg et al. |
| 6,083,723 A | 7/2000 | Tekamp-Olson |
| 6,096,304 A | 8/2000 | McCutchen |
| 6,126,944 A | 10/2000 | Pelett et al. |
| 6,129,912 A | 10/2000 | Hortin et al. |
| 6,162,426 A | 12/2000 | La Gamma |
| 6,165,283 A | 12/2000 | Dahlin et al. |
| 6,166,183 A | 12/2000 | Ishikawa et al. |
| 6,168,932 B1 | 1/2001 | Uckun et al. |
| 6,183,985 B1 | 2/2001 | Shuster |
| 6,183,987 B1 | 2/2001 | van de Wiel et al. |
| 6,184,344 B1 | 2/2001 | Kent et al. |
| 6,188,965 B1 | 2/2001 | Mayo et al. |
| 6,201,072 B1 | 3/2001 | Rathi et al. |
| 6,204,247 B1 | 3/2001 | Gegg et al. |
| 6,214,966 B1 | 4/2001 | Harris |
| 6,225,060 B1 | 5/2001 | Clark et al. |
| 6,235,710 B1 | 5/2001 | Mehta et al. |
| 6,239,100 B1 | 5/2001 | Rodgers et al. |
| 6,242,218 B1 | 6/2001 | Treco et al. |
| 6,245,528 B1 | 6/2001 | Chao |
| 6,261,550 B1 | 7/2001 | Osslund |
| 6,261,805 B1 | 7/2001 | Wood |
| 6,268,336 B1 | 7/2001 | Niitsu et al. |
| 6,269,312 B1 | 7/2001 | Mayo et al. |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,316,254 B1 | 11/2001 | Kaushansky |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,368,854 B2 | 4/2002 | Weiss et al. |
| 6,379,661 B1 | 4/2002 | Souza |
| 6,365,505 B1 | 5/2002 | Lipps |
| 6,403,312 B1 | 6/2002 | Dahiyat et al. |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,455,639 B1 | 9/2002 | Yasukohchi et al. |
| 6,461,603 B2 | 10/2002 | Bentley et al. |
| 6,489,293 B1 | 12/2002 | Sytkowski et al. |
| 6,489,293 B1 | 12/2002 | Sytkowski et al. |
| 6,497,869 B2 | 12/2002 | Williams et al. |
| 6,515,100 B2 | 2/2003 | Harris |
| 6,521,245 B1 | 2/2003 | Zaharia |
| 6,521,427 B1 | 2/2003 | Evans |
| 6,531,121 B2 | 3/2003 | Brines et al. |
| 6,552,167 B1 | 4/2003 | Rose |
| 6,555,660 B2 | 4/2003 | Nissen et al. |
| 6,565,841 B1 | 5/2003 | Niven et al. |
| 6,579,525 B1 | 6/2003 | Haran-Ghera et al. |
| 6,586,207 B2 | 7/2003 | Tirrell et al. |
| 6,602,498 B2 | 8/2003 | Shen |
| 6,608,183 B1 | 8/2003 | Cox, III |
| 6,610,281 B2 | 8/2003 | Harris |
| 6,632,426 B2 | 10/2003 | Osslund |
| 6,646,110 B2 | 11/2003 | Nissen et al. |
| 6,676,947 B1 | 1/2004 | Gottschalk et al. |
| 6,689,351 B1 | 2/2004 | Pierce et al. |
| 6,716,606 B2 | 4/2004 | Souza |
| 6,790,867 B2 | 9/2004 | Kohan et al. |
| 6,908,610 B1 | 6/2005 | Sato |
| 6,927,042 B2 | 8/2005 | Schultz et al. |
| 7,045,337 B2 | 5/2006 | Schultz et al. |
| 7,083,970 B2 | 8/2006 | Schultz et al. |
| 7,144,574 B2 | 12/2006 | Rasmussen et al. |
| 7,182,948 B2 | 2/2007 | Tyndall et al. |
| 7,285,661 B2 | 10/2007 | Sommermeyer et al. |
| 7,381,805 B2 | 6/2008 | Germansen et al. ......... 530/402 |
| 7,557,195 B2 | 7/2009 | Park |
| 11,273,202 B2 * | 3/2022 | Klotz .................. A61K 38/193 |

(56) References Cited

U.S. PATENT DOCUMENTS

| | | |
|---|---|---|
| 2001/0021783 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0037949 A1 | 3/2002 | Harris et al. |
| 2002/0040076 A1 | 4/2002 | Harris et al. |
| 2002/0042097 A1 | 4/2002 | Tirrell et al. |
| 2002/0051789 A1 | 5/2002 | Wagter-Lesperance et al. |
| 2002/0052009 A1 | 5/2002 | Hornauer et al. |
| 2002/0052430 A1 | 5/2002 | Harris et al. |
| 2002/0056169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0186047 A1 | 12/2002 | Zhao |
| 2003/0023023 A1 | 1/2003 | Harris et al. |
| 2003/0082575 A1 | 5/2003 | Schultz et al. |
| 2003/0105224 A1 | 6/2003 | Roberts et al. |
| 2003/0105275 A1 | 6/2003 | Bentley et al. |
| 2003/0108885 A1 | 6/2003 | Schultz et al. |
| 2003/0114647 A1 | 6/2003 | Harris et al. |
| 2003/0143596 A1 | 7/2003 | Bentley et al. |
| 2003/0158333 A1 | 8/2003 | Roberts et al. |
| 2003/0162949 A1 | 8/2003 | Cox |
| 2003/0208046 A1 | 11/2003 | Hunter et al. |
| 2003/0220447 A1 | 11/2003 | Harris |
| 2003/0228274 A1 | 12/2003 | Rose |
| 2003/0228593 A1 | 12/2003 | Suga et al. |
| 2004/0001838 A1 | 1/2004 | Zhao et al. |
| 2004/0013637 A1 | 1/2004 | Bentley et al. |
| 2004/0138412 A1 | 7/2004 | Botti et al. |
| 2004/0198637 A1 | 10/2004 | Schultz et al. |
| 2005/0009049 A1 | 1/2005 | Chin et al. |
| 2005/0063943 A1 | 3/2005 | Sommermeyer et al. |
| 2005/0085619 A1 | 4/2005 | Wilson |
| 2005/0142102 A1 | 6/2005 | Schaebitz et al. |
| 2005/0170404 A1 | 8/2005 | Cho et al. |
| 2005/0220762 A1 | 10/2005 | Cho et al. |
| 2005/0232898 A1 | 10/2005 | Canning |
| 2005/0234230 A1 | 10/2005 | Zander et al. |
| 2005/0238723 A1 | 10/2005 | Zander et al. |
| 2006/0019877 A1 | 1/2006 | Conradt et al. |
| 2006/0121073 A1 | 6/2006 | Goyal et al. |
| 2006/0194256 A1 | 8/2006 | Miao et al. |
| 2006/0217289 A1 | 9/2006 | Miao et al. |
| 2006/0217532 A1 | 9/2006 | Miao et al. |
| 2007/0081971 A1 | 4/2007 | Podobnik ............ A61K 9/0019 424/85.1 |
| 2007/0087961 A1 | 4/2007 | Eichner et al. |
| 2007/0134197 A1 | 6/2007 | Eichner et al. |
| 2007/0156799 A1 | 7/2007 | Glinka et al. |
| 2008/0026046 A1 | 1/2008 | Skufca |
| 2008/0146781 A1 | 6/2008 | Cho et al. |
| 2008/0200657 A1 | 8/2008 | Kang et al. |
| 2008/0300163 A1 | 12/2008 | Cho et al. .......................... 514/2 |
| 2010/0035812 A1 | 2/2010 | Hays Putnam et al. |
| 2010/0104627 A1 | 4/2010 | Furtinger |

FOREIGN PATENT DOCUMENTS

| | | | |
|---|---|---|---|
| EP | 164556 A2 | 12/1885 | |
| EP | 244234 A2 | 11/1887 | |
| EP | 036676 A1 | 9/1981 | |
| EP | 036776 A2 | 9/1981 | |
| EP | 052322 A2 | 5/1982 | |
| EP | 058481 A1 | 8/1982 | |
| EP | 073657 A1 | 3/1983 | |
| EP | 102324 A2 | 3/1984 | |
| EP | 121775 A1 | 10/1984 | |
| EP | 127839 A2 | 12/1984 | |
| EP | 133988 A2 | 3/1985 | |
| EP | 143949-41 | 6/1985 | |
| EP | 154316 A2 | 9/1985 | |
| EP | 155476-41 | 9/1985 | |
| EP | 183503 A2 | 6/1986 | |
| EP | 188256 A2 | 7/1986 | |
| EP | 229108 A1 | 7/1987 | |
| EP | 267851 A2 | 5/1988 | |
| EP | 284044 A | 9/1988 | |
| EP | 324274 A1 | 7/1989 | |
| EP | 329203-41 | 8/1989 | |
| EP | 340986 A2 | 11/1989 | |
| EP | 400472 A2 | 12/1990 | |
| EP | 402378 A1 | 12/1990 | |
| EP | 439508 A1 | 8/1991 | |
| EP | 480480 A2 | 4/1992 | |
| EP | 510358 A1 | 10/1992 | |
| EP | 605963 A2 | 7/1994 | |
| EP | 732403-41 | 9/1996 | |
| EP | 809996 A2 | 12/1997 | |
| EP | 921131 A1 | 6/1999 | |
| EP | 946736 A1 | 10/1999 | |
| EP | 0988861 | 3/2000 | |
| EP | 0985697 B1 | 1/2006 | |
| JP | 60-007934 A | 1/1985 | |
| WO | WO-86/04506 A1 | 8/1986 | |
| WO | WO-86/04605 A1 | 8/1986 | |
| WO | WO-87/02060 A1 | 4/1987 | |
| WO | WO-87/02670 A1 | 5/1987 | |
| WO | WO-87/03689 A1 | 6/1987 | |
| WO | WO-8901038 A1 | 2/1988 | |
| WO | WO-8807082 A1 | 9/1988 | |
| WO | WO-8901037 A1 | 2/1989 | |
| WO | WO-89/10932 A1 | 11/1989 | |
| WO | WO-90/01556 A1 | 2/1990 | |
| WO | WO-9002186 A1 | 3/1990 | |
| WO | WO-9002566 A1 | 3/1990 | |
| WO | WO-9005785 A1 | 5/1990 | |
| WO | WO-9010078 A1 | 9/1990 | |
| WO | WO-9010277 A1 | 9/1990 | |
| WO | WO-9013540-41 | 11/1990 | |
| WO | WO-9014428 A1 | 11/1990 | |
| WO | WO-9100357 A1 | 1/1991 | |
| WO | WO-9201801 A1 | 2/1992 | |
| WO | WO-9202628 A1 | 2/1992 | |
| WO | WO-9216555 A1 | 10/1992 | |
| WO | WO-9216619 A1 | 10/1992 | |
| WO | WO-9303173 A1 | 2/1993 | |
| WO | WO-9315189 A1 | 8/1993 | |
| WO | WO-9321259 A1 | 10/1993 | |
| WO | WO-9404193 A1 | 3/1994 | |
| WO | WO-9409027 A1 | 4/1994 | |
| WO | WO-9414758 A1 | 7/1994 | |
| WO | WO-9415625 A1 | 7/1994 | |
| WO | WO-9417039 A1 | 8/1994 | |
| WO | WO-9418247 A1 | 8/1994 | |
| WO | W-9428024 A1 | 12/1994 | |
| WO | WO-9500162 A1 | 1/1995 | |
| WO | WO-9506058 A1 | 3/1995 | |
| WO | WO-9511924 A1 | 5/1995 | |
| WO | WO-9513312 A1 | 5/1995 | |
| WO | WO-9520572 A1 | 8/1995 | |
| WO | WO-9533490 A1 | 12/1995 | |
| WO | WO-9600080 A1 | 1/1996 | |
| WO | WO-9606161 A1 | 2/1996 | |
| WO | WO-9607670 A1 | 3/1996 | |
| WO | WO-9621469 A1 | 7/1996 | |
| WO | WO-9629400 A1 | 9/1996 | |
| WO | WO-9640791 A1 | 12/1996 | |
| WO | WO-9703106-41 | 1/1997 | |
| WO | WO-9718832 A1 | 5/1997 | |
| WO | WO-97/24445 A1 | 7/1997 | |
| WO | WO-9726332 A1 | 7/1997 | |
| WO | WO-9732607 A2 | 9/1997 | |
| WO | WO-9805363 A2 | 2/1998 | |
| WO | WO-9513090-41 | 5/1998 | |
| WO | WO-9826080 A1 | 6/1998 | |
| WO | WO-9832466 A1 | 7/1998 | |
| WO | WO-9837208 A1 | 8/1998 | |
| WO | WO-9841562 A1 | 9/1998 | |
| WO | WO-98/47089 A1 | 10/1998 | |

(56) References Cited

FOREIGN PATENT DOCUMENTS

| WO | WO-9848837 A1 | 11/1998 |
|---|---|---|
| WO | WO-9903887 A1 | 1/1999 |
| WO | WO-9905297 A1 | 2/1999 |
| WO | WO-9907862 A1 | 2/1999 |
| WO | WO-9909193 A1 | 2/1999 |
| WO | WO-9910515 A1 | 3/1999 |
| WO | WO-9931257 A2 | 6/1999 |
| WO | WO-9932134 A1 | 7/1999 |
| WO | WO-9932139 A1 | 7/1999 |
| WO | WO-9932140 A1 | 7/1999 |
| WO | WO-9945130 A1 | 9/1999 |
| WO | WO-9951721 A1 | 10/1999 |
| WO | WO-9967291-42 | 12/1999 |
| WO | VVO-0020032 A1 | 4/2000 |
| WO | WO-00/23114-42 | 4/2000 |
| WO | WO-00/23472 A2 | 4/2000 |
| WO | WO-0026354 A1 | 5/2000 |
| WO | WO-0055345 A2 | 9/2000 |
| WO | WO-0055353 A1 | 9/2000 |
| WO | WO-0105956 A2 | 1/2001 |
| WO | WO-0127301 A2 | 4/2001 |
| WO | WO-9625496 A1 | 8/2001 |
| WO | WO-0190390 A1 | 11/2001 |
| WO | WO-02/06305 | 1/2002 |
| WO | WO-2003/042235 A2 | 5/2002 |
| WO | WO-02085923 A2 | 10/2002 |
| WO | WO-02088075 A2 | 10/2002 |
| WO | WO-2002/098902 A2 | 12/2002 |
| WO | WO 03/074087 | 9/2003 |
| WO | WO 03/074088 | 9/2003 |
| WO | WO-03101972 A1 | 12/2003 |
| WO | WO-04035605 A2 | 4/2004 |
| WO | WO-04035743 A2 | 4/2004 |
| WO | WO-04058946 A2 | 7/2004 |
| WO | WO-2004/094593 A2 | 11/2004 |
| WO | WO-04094593 A2 | 11/2004 |
| WO | WO-05007624 A2 | 1/2005 |
| WO | WO-05007870 A2 | 1/2005 |
| WO | WO-05019415 A2 | 3/2005 |
| WO | WO-05035727 A2 | 4/2005 |
| WO | 2005039620 | 5/2005 |
| WO | WO-2005042024 A1 | 5/2005 |
| WO | WO-05074524 A2 | 8/2005 |
| WO | WO-05074546-42 | 8/2005 |
| WO | WO-05074650 A2 | 8/2005 |
| WO | WO-2006/068802 A2 | 6/2006 |
| WO | WO-2006/069246 A2 | 6/2006 |
| WO | WO-2008/017603 A1 | 2/2008 |
| WO | 2008122415 | 10/2008 |
| WO | 2010011735 | 1/2010 |
| WO | 2011090305 | 7/2011 |
| WO | WO-9841813 A2 | 12/2019 |

OTHER PUBLICATIONS

Oliver et al., "Udder Health in Periparturient Period", J Dairy Sci (1988) 71:2584-2606.

Pankey et al., "Evalual nine teat dip fon ulations under experimental challenge to *staphylcoccus aureus* and *Streptococcus agalactiae*", J Dairy Sci (1983) 66(1 ):161-167.

Pastmak et al., "A new orthogonal supressor tRNA/Aminoacyl-tRNA Synthetase Pair for Evolving an Organism with an Expanded Genetic Code", Helv Chim Acta (2000) 83:2277-2286.

Pearce et al., "Growth Hormone Binding Affinity for its Receptor Surpasses the Requirements for Cellular Activity", Biochemistry (1999) 38:81-89.

Pearson et al., "The Importance of Silica Type for Reverse-Phase Protein Separations", Anal Biochem (1982) 124:217-230.

Peng et al., "Rapid Purification of Recombinant Baculovirus Using Jores ence-Activated Cell Sorting", BioTechniques (1993) 14(2):274-277.

Powers et al., "Three-dimensional solution structure of human interleukin-4 by multidimensional heteronuclear magnetic resonance spectroscopy," Science (1992) 256 (5064): 1673-1677.

Redfield et al., "Secondary structure and topology of human interleukin 4 in solution," Biochemistry (1991) 30 (46):11029-11035.

Reidhaar-Oison et al., "Identification of Residues Critical to the Activity of Human Granylocyte Colony-Stimulating Factor", Biochemistry (1996) 35(28):9034-9041.

Rice et al., "Regulated expression of an immunoglobulin kappa gene introduced into a mouse lymphoid cell line", PNAS USA (1982) 79(24):7862-7865.

Roberts et al., "Granulocyte colony-stimulating factor induces selective elevations of progenitor cells in the peripheral blood of mice", Expt'l Hematology (1994) 22(12):1156-1163.

Robertson et al., "A General and Efficient Route for Chemical Aminoacylation of Transfer RNAs", J. Am. Chem. Soc. (1991) 113:2722-2729.

Sakamoto et al., "Site-Specific incorporation on unnatural amino acid into proteins in mammalian cell", Nucleic Acids Res. (2002) 30(21):4692-4699.

Saks et al., "An Engineered Tetrahymena tRNAGln for in Vivo Incorporation of Unnatural Amino Acids into Proteins by Nonsense Suppression", J. Biol. Chem. (1996) 271(38):23169-23175.

Smith et al., "Companson of Biosequences", Adv. Appl. Math. (1970) 2:482-489.

Spencer et al., "Rabbit Liver Growth Hormone Receptor and Serum Binding Protein", J. Biol. Chem. (1988) 263 (16):7882-7887.

Tejedor et al., "Iodination of biological samples without loss of functional activity," Anal Biochem (1982) 127 (1):143-149.

Tilkins et al., "Transfection of Mammalian and Invertebrate Cells Using Catatonic Lipids", Cell Biology: A Laboratory Handbook (1998) 4:145-154.

Valls et al., "Protein sorting in yeast: the localization determinant of yeast vacuolar carboxypeptidase Y resides in the propeptide", Cell (1987) 48(5):887-897.

Venula et al., "Production and regulation of interleukin-2 in human lymphoblastic leukemias studied with T-cell monocional antibodies", Blood, (1983) 61(4):781-9.

Waiter et al. "Three-dimensional structure of recombinant human granulocyte-macrophage color-stimulating factor," J Mol Biol (1992) 224(4):1075-1085.

Wawrzynczak et al., "Recombinant mouse monoclonal antibodies with single amino acid substitutions affecting Clq and high affinity Fc receptor binding have identical serum half-lives in the BALB/c mouse", Molecular Immunology (1992) 29(2):221-227.

Weitkamp et al., "Additional data on the population distribution of human serum albumin genes; three new variants", Ann. Hum. Genet. (1973) 37(2):219-26.

Weite et al., Purification and biochemical characterization of human pluripotent hematopoietic colony-stimulating factor, PNAS USA (1985) 82(5):1526-30.

Yan et al., "Mobilization of long-term hematopoietic reconstituting cells in mice by the combination of stem cell factor plus granulocyte colony-stimulating factor", Blood (1994) 84(3):795-799.

Young et al., "Characterizion of the receptor binding determinants of granulocyte colony stimulating factor", Protein Sci., (1997) 6(6):1228-1236.

Zink et al "Secondary structure of human granulocyte colony-stimulating factor derived from NMR spectroscopy," FEBS Lett. (1992) 314(3):435-439.

Zink et al. "Structure and dynamics of the human granulocyle colony-stimulating factor determined by NMR spectroscopy. Loop mobility in a four-helix-bundle protein," Biochemistry (1994) 33(28):8453-8463.

Lovejoy et al., "Crystal structure of canine and bovine granulocyle-colony stimulating factor (G-CSF)", Journal of Molecular Biology, 234:640-653, 1993.

Sakmar, TP and Khorana HG, "Total synthesis and expression of a gene for the alpha-subunit of bovine rod outer segment guanine nucleotide-binding protein (transducin)" Nucleic Acids Res Jul. 25, 1988: 16(14A):6381-72.

Wang et al., "Expanding the genetic code," Chem Commun Jan. 7, 2002;1:1-11.

Weissmann, "The cloning of interferon and other mistakes." in Interferon 3 1981; ed. I. Gresser; Academic Press, London, 101-134.

(56) References Cited

OTHER PUBLICATIONS

Wells, JA et al., "Importance of hydrogen-bond formation in stabilizing the transition state of subtilisin." Phil. Trans. R. Soc. Land. A 1986; 317:415-423.
Wells. JA et al., "Cassette mutagenesis: an efficient method for generation of multiple mutations at defined sites." Gene. 1985:34(2-3):315-23.
Woghiren, C et al. "Protected thiol-polyethylene glycol: a new activated polymer for reversible protein modification," Bioconjug Chem. Sep.-Oct. 1993;4(5):314-8.
Wong, SS et al., "Chemical crosslinking and the stablization of proteins and enzymes," Enzyme Microb Technol. Nov. 1992;14(11):866-74.
Wright, K "Biotechnology: Insect virus as super-vector?" Nature (1986) 321(6072):718.
Holland, MJ et al., "Isolation and identification of yeast messenger ribonucleic acids coding for enolase, glyceraldehyde-3-phosphate dehydrogenase, and phosphorglycerate kinase," Biochemistry. Nov. 14, 1978;17 (23):4900-7.
Holland, MJ et al., "The primary structures of two yeast enolase genes. Homology between the S' noncoding flanking regions of yeast enolase and glyceraldehyde-3-phosphate dehydrogenase genes," J Biol Chem. Feb. 1 0, 1981;256(3): 1385-95.
Hsiao, CL et J Carbon, "High-frequency transformation of yeast by plasmids containing the cloned yeast ARG4 gene," PNAS USA Aug. 1979;76(8):3829-33.
Huisgen, R in 1 ,3-Dipolar Cycloaddilion Chemistry, vol. 1, 1984; Ed. Padwa A.; John Wiley and Sons, New York, p. 1-176.
Hwang, KJ et al., "Hepatic uptake and degradation of unilamellar sphingomyelin-cholesterol liposomes: a kinetic study," PNAS USA Jul. 1980;77(7):4030-4.
Ibba, M et al., "Substrate specificity is determined by amino acid binding pocket size in Escherichia coli phenylalanyl- tRNA synthetase," Biochemistry. Jun. 14, 1994:33(23):7107-12.
Ibba, M and H Hennecke, "Relaxing the substrate specificity of an aminoacyl-tRNA synthetase allows in vitro and in vivo synthesis of proteins containing unnatural amino acids," FEBS Lett. May 15, 1995; 364(3):272-5.
Ito, H. et al., "Transformation of intact yeast cells treated with alkali cations," J. Bacteriol. 1983; 153(1):163-8.
Jackson, DY et al. "A designed peptide ligase for total synthesis of ribonuclease A with unnatural catalytic residues," Science Oct. 14, 1994:268(5183):243-7.
Jakobsson, PJ et al., "Identification and characterization of a novel human microsomal glutathione S-transferase with leukotriene C4 synthase activity and significant sequence identity to 5-lipoxygenase-activating protein and leuxotriene C4 synthase," J Biol Chem Sep. 6, 1996;271(36):22203-10.
Jencks, WP, "Studies on the Mechanism of Oxime and Semicarbazone Formation," J. Am. Chem. Soc. 1959; 81 (2):475-481.
Joppich, M et al., "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979, 160:1381-4.
Kaiser, ET, "Synthetic approaches to biologically active peptides and proteins including enzymes," Acc Chem Res (1989): 22(2):47-54.
Kaiser, ET et al., "The chemical modification of enzymatic specificity," Annu Rev Biochem 1985; 64:565-95.
Kaiser, ET and OS Lawrence "Chemical mutation of enzyme ective sites," Science. Nov. 2, 1984: 226(4674):505-11.
Karlin, Sand SF Altschul "Applications and statistics for multiple high-scoring segments in molecular sequences," PNAS USA Jun. 15, 1993; 90(12):5873-7.
Kayser. B., et al., "Alkyne bridged alpha- amino acids by palladium mediated coupling of alkynes with N-t-Boc-4- iodo-phenylalanine methyl ester," Tetrahedron (1997); 53(7): 2475-2484.
Kelly, JM and MJ Hynes, "Transformation of Aspergillus niger by the amdS gene of Aspergillus nidulans," EMBO J. 1985; 4(2):475-479.

Kiick, K. L. and D. A. Tirrell, "Protein Engineering by In Vivo Incorporation of Non-Natural Amino Acids: Control of Incorporation of Methionine Analogues by Methionyl-tRNA Synthetase," Tetrahedron (2000), 56:9487-9493.
Kiick, KL et al., "Incorporation of azides into recombinant proteins for chemoselective modification by the Staudinger ligation," PNAS USA Jan. 8, 2002: 99(1):19-24. Epub Dec. 18, 2001.
Kim, OM and JR Swartz, "Regeneration of adenosine triphosphate from glycolytic intermediates for cell-free protein synthesis," Biotechnical Biceng Aug. 20, 2001:74(4):309-16.
Kim, OM and JR Swartz. "Oxalate improves protein synthesis by enhancing ATP supply in a cell-free system derived from Escherichia coli," Biotechnology Letters, 2000: 22:1537-1542.
Kim, OM and JR Swartz, "Prolonging cell-free protein synthesis by selective reagent additions," Biotechnol Prog May-Jun. 2000;16(3):385-90.
Kim, OM and JR Swartz, "Prolonging cell-free protein synthesis with a novel ATP regeneration system," Biotechnol Bioeng. 1999; 66(3):180-8.
King, FE & Kidd, Daa "A New thesis of Glutamine and of gamma-Dipeptides of Glutamic Acid from Phthylated Intermediates," J. Chem. Soc. 1949; 3315-3319.
Kingsman, AJ et al., "Replication in Saccharomyces cerevisiae of plasmid pBR313 carrying DNA from the yeast trpl region," Gene. Oct. 1979: 7(2):141-52.
Kitis, PA et al. "Linearization of baculovirus DNA enhances the recovery of recombinant virus expression vectors," Nucleic Acids Res. Oct. 11, 1990, 16(19):5867-72.
Klein, TM et al., "High velocity microprojectiles for delivering nucleic acids into living cells," Nature 1987; 327 (6117):70-73.
Kobayashi, T et al., "Structural basis for orthogonal tRNA specificities of tyrosyl-tRNA synthetases for genetic code expansion," Nature Structural Biology (2003); 10 (6):425-432.
Kogan, TP "The synthesis of substituted methoxy-poly(ethyleneglycol) derivatives suitable for selective protein modification protein modification," Synthetic Comm 1992; 22(16):2417-24.
Kool, ET "Synthetically modified DNAs as substrates for polymerases," Curr Opin Chem Biol Dec. 2000; 4(6):602-8.
Koskinen, AMP & Rapoport, H "Synthesis of 4-Substituted Pralines as Confrmationally Constrained Amino Acid Analogues," J. Org. Chem (1989) 54(8): 1859-1866.
Kost, TA et al., "Production of a urokinase plasminogen activator-IgG fusion protein (uPA-IgG) in the baculovirus expression system," Gene. Apr. 29, 1997; 190(1):139-44.
Kramer, W & Fritz HJ. "Oligonucieotide-directed construction of mutations via gapped duplex DNA" Methods Enzymol. 1987;154:350-67.
Kramer, W. et al., "Improved enzymatic in vitro reactions in the gapped duplex DNA approach to oligonucleotide- directed construction of mutations," Nucleic Acids Res. Jul. 25, 1998; 16(14B):7207.
Kramer, B. et al., "Different base/base mismatches are corrected with different efficiencies by the methyl-directed DNA mismatch-repair system of E. Coli," Cell. Oct. 1984; 38(3):879-87.
Kreitman, RJ and I. Pastan "Purification and characterization of IL6-PE4E, a recombinant fusion of interleukin 6 with Pseudomonas exotoxin," Bioconjug Chem. Nov.-Dec. 1993; 4(6):581-5.
Kreig. UC et al., "Photocrosslinking of the signal of nascent preprolactin to the 54-kilodation polypeptide of the signal recognition particle," PNAS USA Nov. 1986; 83(22):8604-8.
Kunitani, M. et al., "Reversed-phase chromatography of interleukin-2 muteins," J Chromatogr. May 30, 1986; 359:391-402.
Kunkel, "The efficiency of oligonucleotide directed mutagenesis," in Nucleic Acids & Molecular Biology 1987: Eckstein, F. and Lilley, D.M J. eds.; Springer Verlag, Berlin; 124-135.
Kunkel, TA Rapid and efficie at site-specific mutagenesis without phenotypic selection, PNAS USA Jan. 1985: 82(2):468-92.
Kunkel TA et al., "Rapid and efficient site-specifc mutagenesis without phenotypic selection," Methods Enzymol. 1987; 154: 367-82.
Kunze, Get al., "Transformation of the industrially important yeasts Candida maltosa and Pichia guilliermondii," J. Basic Microbiol. 1985; 25:141-4.

(56) References Cited

OTHER PUBLICATIONS

Kurtz et al., "Integrative transformation of Candida albicans, using a cloned Candida ADE2 gene," Mol Cell Biol. Jan. 1986;6(1):142-9.
Kurtzhals, Pet al., "Albumin binding of insulins acylated with fatty acids: characterization of the ligand-protein interaction and correlation between binding affinity and timing of the insulin effect in vivo," Biochem J. Dec. 15, 1995:312 ( Pt 3): 725-31.
Langer, Ret al., "Biocompatibility of polymeric delivery systems for macromolecules," J Biomed Mater Res. Mar. 1981; 15(2):267-77.
Langer, R. "Controlled release of macromolecules," Chem. Tech. 1982; 12:98-105.
Liebman, JM et al., "When less is more: enhanced bacutovirus prooduction of recombinant proteins at very low multiplicities of infection," Biotechniques. Jan. 1999: 26(1 ) 36-8, 40, 42.
Ling, MM & BH Robinson. "Approaches to DNA mutagenesis: an overview" Anal Biochem Dec. 15, 1997; 254 (2):157-78.
Van Hest, JC et al., "Efficient Incorporation of Unsaturated Methionine Analogues into Proteins in Vivo," J. Am. Chem. Soc. 2000; 122 (7): 1282-1288.
Van Solingen, P & JB van der Plaal, "Fusion of yeast spheroplasts." J Bacterial May 1977; 130(2):946-7.
Veronese, FM et al., "Surface modification of proteins. Activation of monomethoxy-polyethylene glycols by phenylchloroformates and modification of ribonuclease and superoxide dismutase." Appl Biochem Biotechnol. Apr. 1985; 11 (2):141-52.
Vlak, JM et al., "Functional studies on the p10 gene of Autographa californica nuclear polyhedrosis virus using a recombinant expressing a p10-bela-galactosidase fusion gene," J Gen Virol. Apr. 1988. 69 (PI 4):765-76.
Wang, Q., et al., "Bioconjugation by Copper( I) Catalyzed Azide-Alkyne [3 + 2] Cycloaddilion," J. Am. Chem. Soc. 2003; 125(11):3192-3193.
Wang, L et al., "Addition of the keto functional group to the genetic code of *Escherichia coli*," PNAS USA (2003): 100(1):56-61.
Wang, L et al., "Expanding the genetic code of *Escherichia coli*," Science. Apr. 20, 2001; 292(5516):498-500.
Deiters, A et al., "Adding Amino Acids with Novel Reactivity to the Genetic Code of *Saccharomyces cerevisiae*," J. Am. Chem. Soc. 2003; 125(39):11782-11783.
Delgado, C et al., "The uses and properties of PEG-linked proteins," Crit Rev Ther Drug Carrier Syst. 1992; 9 (3-4):249-304.
Dennis, MS et al., "A fegy for improving the pham okinetics of proteins," J Biol Chem Sep. 20, 2002; 277 (38):35035-43. Epub Jul. 15, 2002.
Dolphin, CT et al., "Missense mutation in flavin-containing monooxygenase 3 gene, FM03, underlies fish-odour syndrome," Nat Genet Dec. 1997; 17(4):491-4.
Döring. Vet al., "Enlarging the amino acid set of *Escherichia coli* by infiltration of the valine coding pathway," Science Apr. 20, 2001: 292(5516):501-4.
Dougherty, DA. "Unnatural amino acids as probes of protein structure and function," Curr Opin Chem Biol Dec. 2000; 4(6):645-52.
Duewel, H et al., "Incorporation of trifluoromethionine into a phage lysozyme: implications and a new marker for use in protein 19F NMR," Biochemistry Mar. 18, 1997; 36(11 ):3404-16.
Eghtedarzadeh MK & S Henikoff "Use of oligonucleotides to generate large decisions" Nucleic Acids Res Jun. 25, 1986: 14(12):5115.
Elling Let MR Kula., "Immunoaffinity partitioning: synthesis and use of polyethylene glycol-oxirane for coupling to bovine serum albumin and monoclonal antibodies," Biotechnol Appl Biochem Jun. 1991;13(3):354-62.
Ellioti, Set al., "Yeast-derived recombinant human insulin-like growth factor 1: production, purification, and structural characterization," J Protein Chem Feb. 1980; 9(1):95-104.
Ellman, JA, Mendel, D., Anthony-Cahill, S., Noren, C.J., Schultz, P.G. "Biosynthetic method for introducing unnatural amino acids site-specfically into proteins," Methods Enzymol 1991; 202:301-336.

Ellan, JA, et al. "Site-specific incorporation of novel backbone structures into proteins," Science Jan. 10, 1992; 255 (5041):197-200.
England, PM et al., "Backbone mutations in transmembrane domains of a ligand-gated ion channel: implications for the mechanism of gating," Cell Jan. 8, 1999: 96(1 ):89-98.
Eppstein et al., "Biological Activity of Liposome-Encapsulated Murine Interferon is Mediated by a Cell Membrane Receptor," PNAS USA (1985); 82: 3688-3692.
Fieschko, JC et al., "Controlled expression and purification of human immune interferon from high-cell-density fermentations of *Sacchaomyces cerevisiae*," Biotech. Bioeng. (1987) 29(9):1113-21.
Forster, AC et al.,"Programming peptidomimetic syntheses by translating genetic codes designed de novo," PNAS US A. May 27, 2003; 00(11):6353-7. Epub May 16, 2003.
Frankel, A et al., "Encodamers: unnatural peptide oligomers encoded in RNA," Chem Biol Nov. 2003; 10 (11 ):1043-50.
Fraser, MJ et al., "Expression of euc genes in insect cell cultures," In Vitro Cell Dev Biol 1989: 26:225-235.
Friedman, OM & R Chatterrji "Synthes of Derivatives of Glutamine as Model Substrates for Anti-Tumor Agents" J. Am. Chem. Soc. 1959; 81(14):3750-3752.
Fritz HJ et al., "Oligonucleotide-directed construction of mutations: a gapped duplex DNA procedure without enzymatic reactions in vitro," Nucleic Acids Res. Jul. 25, 1988; 16(148):6987-99.
Fromm, M. et al , "Expression of Genes Transferred into Monaco! and Dicot Plant Cells by Electroporation," PNAS USA (1985) 82:5824-8.
Furter, R. "Expansion of the genetic code: site-directed p-fluoro-phenylalanine incorporation *Escherichia coli*," Protein Sci Feb. 1998; 7(2):419-26.
Gaertner, HF et al., "Construction of protein analogues by site-specific condensation of unprotected fragments," Bioconjug Chem May-Jun. 1992; 3(3):262-8.
Gaertner, HF et al., "Chemo-enzymic backbone engineering of proteins. Site-specific incorporation of synthetic peptides that mimic the 64-74 disulfide loop of granulocyle colony-stimulating factor," J Biol Chem. Mar. 11, 1994; 269 (10):7224-30.
Gallivan, JP et al., "Site Specific incorporation of biotinylated amino acids to identify surface-exposed residues in integral membrane proteins," Chem Biol Oct. 1997; 4(10):739-49.
Gellissen, Get al., "Heterologous protein production in yeast." Antonie Van Leeuwenhoek Aug. 1992; 62(1-2):79-93.
Geoghegan, KF and JG Stroh, "Site-directed conjugation of nonpeptide groups to peptides and proteins via periodate oxidation of a 2-amino alcohol. Application to modification at N-terminal serine," Bioconjug Chem Mar.-Apr. 1992; 3(2):138-46.
Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.
Gleeson, MA et al., "Transformation of the methylotrophic yeast hansenula polymorphica," J. Gen. Microbiol. (1986) 132:3459-3465.
Goeddel, DV, "Systems for heterplogous gene expression," Methods Enzymol 1990; 185:3-7.
Goeddel, DV et al., "Synthesis of human fibroblast interferon by *E. coli*," Nucleic Acids Res, Sep. 25, 1980, 8 (18):4057-74.
Graves, SW et al., "Expression, purification, and initial kinetic characterization of the large subunit of the human mitochondrial DNA polymerase," Biochemistry. Apr. 28, 1998: 37(17):6050-8.
Griffin, BA et al., "Specific Covalent Labeling of Recombinant Protein Molecules Inside Live Cells," Science (1998) 281 :269-272.
Grundström T et al., "Oligonucleotide-directed mutagenesis by microscale 'shot-gun' gene synthesis," Nucleic Acids Res. May 10, 1985; 13(9):3305-16.
Guckian, KM and ET Kool, "Highly Precise Shape Mimicry by a Difluorotoluene Deoxynucleoside, a Replication- Competent Substitute for Thymidine," Angew. Chem. Int. Ed. Engl (1998) 36(24):2825-8.
Hamano-Takaku, F et al., "A mutant *Escherichia coli* tyrosyl-IRNA synthetase utilizes the unnatural amino acid azatyrosine more efficiently than tyrosine." J Bio Chem Dec. 22, 2000;275(51 ):40324-8.

(56) References Cited

OTHER PUBLICATIONS

Hang, HC and CR Bertozzi, "Chemoselective approaches to glycoprotein assembly," Acc Chem Res Sep. 2001; 34 (9):727-38.
Harris, JM et al. "Synthesis and Characterization of Poly(ethylene Glycol) Derivatives," J. Polym. Sci. Chem. Ed. 1984, 22:341-352.
Harris, JM. "Laboratory Synthesis of Polyethylene Glycol Derivatives," JMS-Rev. Macromol. Chem. Phys. 1985; C25 (3): 325-373.
Hendrickson, WA et al., "Selenomethionyl proteins produced for analysis by multiwavelength anomalous diffraction (MAD): a vehicle for direct of three-dimensional structure," EMBO J. May 1990;9(5):1665-72.
Henikoff, S and JG Henikoff "Amino Acid Substitution Matrices from Protein Blocks," PNAS USA 1992, 89:10915-9.
Hess, B et al., "Cooperation of glycolytic enzymes," J. Adv. Enzyme Reg. (1969) 7:149-67.
Hinnen, A et al., "Transformation of yeast." PNAS USA Apr. 1978, 75(4):1929-33.
Hirao, I et al., "An unnatural base pair for incorporating amino acid analogues into proteins," Nat Biotechnol Feb. 2002; 20(2): 177-82.
Hitzeman, RA et al., "Isolation and characterization of the yeast 3-phosphoglycerokinase gene (PGK) by an immunological screening technique," J. Biol. Chem. Dec. 25, 1980; 255(24):12073-80.
Hofmann, K. & H. Bohn. "Studies on polypeptides. XXXVI. The effect of pyrazole-imidazole replacements on the S-protein activating potency of an S-peptide fragment," J. Am. Chem. (1966); 88(24):5914-5919.
Hohsaka, T et al., "Efficient Incorporation of Nonnatural Amino Acids with Large Aromatic Groups into Streptavidin in In Vitro Protein Synthesizing Systems," J. Am. Chem. Soc. 1999; 121(1):34-40.
Hohsaka, T et al., "Incorporation of Two Different Nonnatural Amino Acids independently Into a Single Protein through Extension of the Genetic Code," J. Am. Chem. Soc. 1999; 121(51):12194-12195.
Tondelli. L. et al. "Polyethylene Glycol) Imidazolyl Formates as Oligomeric Drug-Binding Matrices," J. Controlled Release 1985; 1(4):251-7.
Tornøe, CW et al., "Peptidotriazoles on solid phase: [1,2,3]-triazoles by regiospecific copper(i)-catalyzed 1,3-dipolar cycloadditions of terminal alkynes to azides," J Org Chem May 3, 2002;67(9):3057-64.
Trotter, KM and HA Wood, "Transfection techniques for producing recombinant baculoviruses," in Methods in Molecular Biology-Baculovirus Expression Protocols, vol. 39 (1995); Ed. C.D. Richardson, 97-107.
Tschumper, G et al., "Sequence of a yeast DNA fragment containing a chromosomal replicator and the TRP1 gene," Gene 1980; 10(2):157-66.
Turcatti, G et al., "Probing the structure and function of the tachykinin neurokinin-2 receptor through biosynthetic incorporation of fluorescent amino acids at specific sites," J Biol Chem Aug. 16, 1996; 271(33):19991-8.
Van Den Berg, JA et al., "Kluyveromyces as a host for heterologous gene expression: expression and secretion of prochymosin," Biotechnology (NY) Feb. 1990; 8(2):135-9.
Altschul, SF et al., "Gapped BLAST and PSI-BLAST: a new generation of protein database search programs," Nucleic Acids Res. Sep. 1, 1997; 25(17):3389-402.
Altschul, SF et al., "Basic local alignment search tool," J Mol Biol Oct. 5, 1990; 215(3):403-10.
Amann, E et al., "Vectors bearing a hybrid trp-lac promoter useful for regulated expression of cloned genes in Escherichia coli," Gene Nov. 1983; 25(2-3):167-78.
Anderson, JC et al., "Exploring the limits of codon and anticodon size," Chem Biol Feb. 2002;9(2):237-44.
Abuchowski. A. et al., "Cancer therapy with chemically modified enzymes. I. Antitumor properties of polyethylene glycol-asparaginase conjugates." Cancer Biochem Biophys Jun. 1984; 7(2):175-86.

Arnold, FH. "Protein engineering for unusual environments," Curr Opin Biotechnol Aug. 1993; 4(4):450-5.
Azoulay. M. et al., "Glutamine analogues as Potential Antimalarials," Eur. J. Med. Chem. (1991); 26(2):201-5.
Bain, JD et al. "Biosynthetic site-specific incorporation of a non-natural amino acid into a polypeptide," J Am Chem Soc 1989; 111(20):8013-8014.
Ballance, DJ et al., "Transformation of Aspergillus nidulans by the orolidine-5'-phosphate decarboxylase gene of Neurospora crassa," Biochem Biophys Res Commun Apr. 15, 1983; 112(1):284-9.
Barany, F et al., "Genetic disease detection and DNA amplification using cloned thermostable ligase," PNAS USA Jan. 1, 1991; 88(1):189-93.
Barton. DHR et al., "Synthesis of Novel alpha-Amino-Acids and Derivatives Using Radical Chemistry: Synthesis of L-and D-alpha-Amino-Adipic Acids, L-alpha-aminopimelic Acid and Appropriate Unsaturated Derivatives," Tetrahedron (1887) 43:4297-4308.
Bass, S et al., "Mutant Trp repressors with new DNA-binding specificities," Science (1988) 242:240-245.
Batzer, MA et al., "Enhanced evolutionary PCR using oligonucleotides with inosine at the 3'-terminus," Nucleic Acids Res Sep. 25, 1991; 19(18):5081.
Beach, D et al., "Functionally homologous cell cycle control genes in budding and fission yeast," Nature Dec. 1982; 300:706-708.
Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem May 1983; 131(1):25-33.
Bernstein, FC, et al., "The protein data bank: a computer-based archival file for macromolecular structures," J. Mol Biol 1977; 112:535-542.
Boissel, JP et al., "Erythropoietin structure-function relationships. Mutant proteins that test a model of tertiary structure," J Biol Chem Jul. 25, 1993; 268(21):15983-93.
Boles, JO et al., "Bio-incorporation of telluromethionine into buried residues of dihydrofolate reductase," Nat Struct Biol May 1994; 1(5):283-4.
Botstein, D & D Shortie. "Strategies and applications of in vitro mutagenesis," Science Sep. 20, 1985; 229 (4719):1193-201.
Brunner, J "New photolabeling and crosslinking methods," Annu Rev Biochem 1993;62:483-514.
Buchner, J et al., "A method for increasing the yield of properly folded recombinant fusion proteins: Single-chain immunotoxins from renaturation of bacterial inclusion bodies," Anal. Biochem. 1992; 205(2): 263-270.
Bückmann et al., "Functionalization of Poly(ethylene glycol) and Monomethoxy-Poly(ethylene glycol)," Makromol Chem. 1981; 182:1379-84.
Budisa N et al., "High-level biosynthetic substitution of methionine in proteins by its analogs 2-aminohexanoic acid, selenomethionine, telluromethionine and ethionine in *Escherichia coli*." Eur J Blochem Jun. 1, 1995; 230(2):788-96.
Budisa. N et al., "Bioincorporation of tellurromethionine into proteins: a promising new approach for X-ray structure analysis of proteins," J Mol Biol Jul. 25, 1997; 270(4):616-23.
Budisa, N et al., "Toward the experimental codon reassignment in vivo: protein building with an expanded amino acid repertoire," FASEB J. Jan. 1999; 13(1):41-51.
Cai. X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.
Carbonell, LF et al., "Baculovirus-mediated expression of bacterial genes in dipteran and mammalian cells," J Viral. Oct. 1985; 56(1):153-60.
Carrasco. M. and R. Brown, "A Versatile Set of Aminooxy Amino Acids for the Synthesis of Neoglypeptides," J. Org. Chem. (2003); 68(23): 8853-8858.
Carter, P "Site-directed mutagenesis," Jul. 1, 1988; 237(1):1-7.
Carter, P et al., "Improved oligonucleotide site-directed mutagenesis using M13 vectors" Nucleic Acids Res Jun. 25, 1985; 13(12):4431-43.

(56) References Cited

OTHER PUBLICATIONS

Carter, P "Improved oligonucleotide-directed mutagenesis using M13 vectors" Methods Enzymol 1987; 154 382-403.

Chaiken, IM "Semisynthetic peptides and proteins," CRC Crit Rev Biochem 1981; 11(3):255-301.

Chin. JW et al., "Addition of p-azido-L-phenylalanine to the genetic code of *E. coli*," J Am Chem Soc Aug. 7, 2002; 124 (31 ):9026-7.

Chin, JW et al., "Addition of a photocrosslinking amino acid to the genetic code of *Escherichia coli*," PNAS USA Aug. 20, 2002; 99(17):11020-4. Epub Aug. 1, 2002.

Chin, JW et al., "An expanded eukaryotic genetic code," Science Aug. 15, 2003; 301(5635):964-7.

Chin, JW & PG Schultz, "In vivo photocrosslinking with unnatural amino acid mutagenesis," Chembiochem Nov. 4, 2002: 3(11): 1135-7.

Christie, BD & Rapoport, H "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985; 50(8):1239-1246.

Clark, R et al., "Long-acting growth hormones produced by conjugation with polyethylene glycol," J Biol Chem Sep. 6, 1996; 271 (36):21969-77.

Corey, DR & Schultz, PG "Generation of a hybrid sequence-specific single-stranded deoxyribonuclease," Science 1987; 238(4832):1401-1403.

Cornish, VW et al., "Site-Specific Protein Modification Using a Ketone Handle," J. Am. Chem. Soc. 1996; 118 (34):8150-8151.

Cornish, Vw et al., "Probing Protein Structure and Function with an Expanded Genetic Code," Angew Chem Int Ed Engl, 1995; 34(6):621-33.

Craig, JC et al., "Absolute Configuration of the Enantiomers of 7-Chloro-4 [[4-(diethylamino)-1-methylbutyl]amino] quinoline (Chloroquine)," J. Org. Chem, 1988; 53(6):1167-1170.

Cregg, JM et al., "Pichia pastoris as a host for transformations," Mol Cell Biol Dec. 1985; 5(12):3376-85.

Crick, FHC et al. "General nature of the genetic for proteins," Nature. Dec. 30, 1961, 192:1227-32.

Dale et al., "Oligonucleotide-directed random mutagenesis using the phosphorothioste method." Methods Mol. Biol. 1996; 57:369-374.

Das, S et al., "Transformation of Kluyveromyces fragilis," J Bacterial Jun. 1984; 158(3):1165-7.

Dawson, PE & SBH Kent, "Synthesis of native proteins by chemical ligation," Annu. Rev. Biochem. 2000, 69:923-60.

De Boer, HA et al., "The tac promoter a functional hybrid derived from the trp and lac promoters," PNAS USA Jan. 1983; 80(1) 21-5.

De Louvencourt, L et al., "Transformation is by Kluyveromyces lactis by killer plasmid DNA," J Bacterial May 1983; 154(2):737-42.

Kramer, W et al., "The gapped duplex DNA approach to oligonucleotide-directed mutation construction," Nucleic Acids Res Dec. 21, 1984; 12(24):9441-56.

Mehl RA et al., "Generation of a bacterium with a 21 amino acid genetic code," J Am Chem Soc Jan. 29, 2003; 125 (4):935-9.

Santoro, SW et al., "An efficient system for the evolution of aminoacyl-tRNA synthetase specificity," Nat Biotechnol Oct. 2002; 20(10):1044-8. Epub Sep. 16, 2002.

Caliceti. P & FM Veronese. "Pharmacokinetic and biodistribution properties of poly(ethylene glycol)-protein conjugates," Adv Drug Deliv Rev Sep. 26, 2003; 55(10):1261-77.

Clark, EDB, "Refolding of recombinant proteins," Curr Opin Biotechnol Apr. 1, 1998, 9(2): 157-83.

Clark, EDB, "Protein refolding for industrial processes," Curr Opin Biotechnol Apr. 2001; 12(2):202-7.

Davis, GD et al., "New fusion protein systems designed to give soluble expression in *Escherichia coli*," Biotechnol Bioeng Nov. 20, 1999; 65(4):382-8.

Raibaud O & M Schwartz "Positive control of transcription initiation in bacteria." Annu Rev Genet 1984; 18:173-206.

Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271 (39):23607-10.

Rivier, J & R McClintoc, "Reversed-Phase high-performance liquid chromatography of insulins from different species," J Chromatogr Sep. 23, 1983; 268(1 ):112-9.

Roberts, S et al., "Generation of an antibody with enhanced affinity and specificity for its antigen by protein engineering," Nature 1987: 328:731-734.

Roberts, RW & JW Szostak, "RNA-peptide fusions for the in vitro selection of peptides and proteins," PNAS USA Nov. 11, 1997; 94(23):12297-302.

Roggenkamp, R et al., "Transformation of the methylotrophic yeast Hansenula polymorpha by autonomous replica and integration vectors," Mol Genetics and Genomics 1986; 202(2):302-8.

Romani, S et al., "Synthesis of unsymmetrical cystine peptides: directed disulfide pairing with the sulfenohydrazide method," in Chemistry of Peptides and Proteins 1984; eds. Voeller, W. et al.; Walter de Gruyter et al., Berlin; vol. 2:29-34.

Romanos. MA et al., Foreign gene expression in yeast: a review, Yeast. Jun. 1992; 8(6):423-88.

Rosenthal, GA. "L-canaline: a potent antimetabolite and anti-cancer agent from leguminous plants," Life Sci 1997; 60(19):1635-41.

Rossolini, GM et al., "Use of deoxyinosine-containing primers vs degenerate primers for polymerase chain reaction based on ambiguous sequence information." Mol. Cell. Probes 1994: 8:91-98.

Rostovtsev, VV et al., "A stepwise huisgen cycloaddition process: copper(I)-catalyzed regioselective "ligation" of azides and terminal alkynes," Angew Chem Int Ed Engl Jul. 15, 2002; 41(14):2596-9.

Sandler and Karo, "Polyoxalkylation of hydroxyl compounds," in Polymer Synthesis, vol. 3, 1980; Academic Press, New York, 138-161.

Sartore, L. et al., "Enzyme modification by MPEG with an amino acid or peptide as spacer arms," Appl Biochem Biotechnol Jan. 1991; 27(1):45-54.

Sawhney, AS et al , "Bioerodible Hydrogels Based on Photopolymerized Poly(ethylene glycol)-co-poly(alpha-hydroxy acid) Diacrylat Macromers," Macromolecules 1993; 26(4):581-7.

Saxon, E & C. Bertozzi, "Cell Surface Engineering by Modified Staudinger Reaction," Science (2000); 287 (5460):2007-2010.

Sayers, Jr et al., "Strand specific cleavage of phosphorothioale-containing DNA by reaction with restriction endonucleases in the pr of athidium bromide," Nucleic Acids Res. Feb. 11, 1988; 16(3):803-14.

Sayers, Jr et al., "5'-3' exonucleases in phos xothioate-based oligonucleotide-directed mutagenesis," Nucleic Acids Res. Feb. 11, 1988; 16(3):791-802.

Schanbacher, FL et al., "Galactosyltransferase Acceptor Specificity of the Lactose Synthetase A Protein," J. Biol. Chem. 1970; 245(19):5057-5081.

Schmidt, M et al., "Baculovirus-mediated large-scale expression and purification of a polyhistidine-tagged rubella virus capsid protein," Protein Expr Purif Apr. 1998; 12(3):323-30.

Schneider, E et al., "Functional Purification of a Bacterial ATP-Binding Cassette Transporter Protein (Maik) from the Cytoplasmic Fraction of an Overproducing Strain," Protein Expr Puril 1995; 6(1):10-14.

Schnölzer. M. & SBH Kent. "Constructing proteins by dovetailing unprotected synthetic peptides: backbone- engineered HIV protease." Science Apr. 10, 1992; 256(5054):221-5.

Scouten, WH "A survey of enzyme coupling techniques." Methods Enzymol. 1987; 135:30-85.

Shao, J and JP Tam, "Unprotected Peptides as Building Blocks for the Synthesis of Peptide Dendrimers with Oxime, Hydrazone, and Thiazolidine Linkages," J. Am. Chem. Soc 1995; 117(14):3893-3899.

Sharma, N et al., "Efficient introduction of aryl bromide functionality into proteins in vivo," FEBS Lett Feb. 4, 2000; 467 (1 ):37-40.

Shimatake, H & M Rosenberg, "Purified gamma regulatory protein ell positively activates promoters for lysogenic development," Nature Jul. 1981; 292:128-132.

(56) References Cited

OTHER PUBLICATIONS

Shine, J & L Dalgarno, "Determinant of cistron specificity in bacterial ribosomes," Nature Mar. 6, 1975; 254 (5495):34-8.
Sidman, KR et al., "Controlled release of macromolecules and pharmaceuticals from synthetic polypeptides based on glutamic acid," Biopolymers Jan. 1983; 22(1):547-56.
Sieber, V. et al., "Libraries of hybrid proteins from distantly related sequences," Nature Biotechnology May 2001; 19:456-460.
Siffert, Wet al., "Association of a human G-protein beta3 subunit variant with hypertension," Nat Genet. Jan. 1998; 18(1):45-8.
Sikorski, RS et al., "A System of Shuttle Vectors and Yeast Host trains Designed for Efficient Manipulation of DNA Genetics in *Saccharommyces cerevisiae*," Genetics (1989) 122:19-27.
Sisk, WP et al , "High-level expression and purification of secreted forms of herpes simplex virus type 1 glycoprotein gD synthesized by baculovirus-infected insect cells," J Viral Feb. 8, 1994;68(2):766-75.
Sjolander. A et al., "The serum albumin-binding region of streptococcal protein G: a bacterial fusion partner with carrier-related properties," J Immunol Methods Feb. 14, 1997; 201(1):115-23.
Smith, M "In vitro mutagenesis," Ann. Rev. Genet. 1985; 19:423-462.
Smith, GE et al., "Production of human beta interferon in insect cells infected with a baculovirus expression vector," Mol Cell Biol Dec. 1983; 3(12):2156-65.
Stanley, SL et al., "The serine-rich Entamoeba histolytica protein is a phosphorylated membrane protein containing O-linked terminal N-acetylglucosamine residues," J Biol Chem Feb. 24, 1995; 270(8):4121-6.
Steitz, JA et al., "Genetic signals and nucleotide sequences in messenger RNA," in Biological Regulation and Development: Gene Expression 1979; ed. RF Goldberger; Plenum Press, New York; 349-399.
Stemmer, WPC "Rapid evolution of a protein in vitro by DNA shuffling," Nature 1994; 370(4):389-391.
Stemmer, WP "DNA shuffling by random fragmentation and reassembly: In vitro recombination for molecular evolution," PNAS USA Oct. 25, 1994; 91(22):10747-51.
Studier, FW & BA Moffatt, "Use of bacteriophage T7 RNA polymerase to direct selective high-level expression of cloned genes," J Mol Biol May 5, 1986; 189(1):113-30.
Subasinghe, N et al., "Quisqualic acid analogues: synthesis of beta-heterocyclic 2-aminopropanoic acid derivatives and their activity at a novel quisqualate-sensitized site," J Med Chem Nov. 27, 1992; 35(24):4602-7.
Switzer, C et al., "Enzymatic incorporation of a new base pair into DNA and RNA," J. Am. Chem. Soc. 1989; 111 (21):8322-8323.
Tabor, S & CC Richardson, "A bacteriophage T7 RNA polymerase/promoter system for controlled exclusive expression of specific genes," PNAS USA Feb. 1985; 82(4):1074-8.
Tae, EL et al., "Efforts toward Expansion of the Genetic Alphabet: Replication of DNA Three Base Pairs," J. Am. Chem. Soc. 2001; 123(30):7439-7440.
Tang, Y et al., "Fluorinated Coiled-Coil Proteins Prepared In Vivo Display Enhanced Thermal and Chemical Stability," Angew Chem Int Ed Engl Apr. 17, 2001; 40(8):1494-1496.
Taylor, JW et al., "The Use of phosphorothioate-modified DNA in restriction enzyme reactions to prepare nicked DNA," Nucleic Acids Res Dec. 1985; 13(24):8749-64.
Taylor, JW et al., "The rapid generation of oligonucleotide-directed mutations at high frequency using phosphoroothioate-modified DNA," Nucleic Acids Res Dec. 20, 1985; 13(24):8765-85.
Tijssen, P "Overview of principles of hybridization and the strategy of nucelic acis assays," in Laboratory Techniques in Biochemistry and Molecular Biology-Hybridization with Nucleic Probes, Part I, 1993; Elsevier Science Publishers, Amsterdam, 19-78.
Tilburn, J et al., "Transformation by integration in Apergillus nidulans," Gene Dec. 1983; 26(2-3):205-21.
Yelton, MM et al., "Transformation of Aspergillus nidulans by using a trpC plasmid," PNAS USA Mar. 1984; 81 (5):1470-4.

Yelverton, E. et al., "Bacterial synthesis of a novel human leukocyte interferon," Nucelic Acids Res Feb. 11, 1981; 9 (3):731-41.
Zalipsky, S etal., "Attachment of drugs to polyethylene glycols," Eur Polymer Journal 1983 19(12):1177-83.
Zalipsky, S. "Functionalized poly( ethylene glycol) for preparation of biologically relevant conjugates," Bioconjung Chem Mar.-Apr. 1995;6(2):150-65.
Zhang, Z et al., "A new strategy for the site-speific modification of proteins in vivo," Biochemistry Jun. 10, 2003, 42 (22):6735-46.
Zoller, MJ & M Smith, "Oligonucleotide-directed mutagenesis using M13-derived vectors: an efficient and general procedure for the production of point mutations in any fragment of DNA," Nucleic Acids Res Oct. 25, 1982; 10 (20):6487-500.
Zoller, MJ & M. Smith, "Oligonucleotide-directed mutagenesis of DNA fragments cloned into M13 vectors," Methods Enzymol. 1983; 100:468-500.
Liu, H et al., "A Method for the Generation of Glycoprotein Mimetics," J Am Chem Soc 2003 125(7): 1702-1703.
Liu, Dr & Schultz, PG, "Progress toward the evolution of an organism with an expanded genetic code," PNAS USA Apr. 27, 1999; 96(9):4780-5.
Lorimer, IA & I Pastan, "Random recombination of antibody single chain Fv sequences after fragmentation with DNasaI in the presence of Mn2+," Nucleic Acids Res Aug. 11, 1995; 23(15):3067-8.
Lu, T et al., "Probing ion permeation and gating in a K +channel with backbone the selectivity filter," Nature Neurosci Mar. 2001; 4(3):239-248.
Luckow, VA & MD Summers, "High level expression of nonfused foreign genes with Autographa californica nuclear polyhedrosis virus expression vectors," Virology May 1989; 170(1):31-9.
Ma, C et al., "In vitro protein engineering using synthetic tRNA(Ala) with different anticodons," Biochemistry Aug. 10, 1993; 32(31):7939-45.
Magliery, TJ et al. "Expanding the Genetic Code: Selection of Efficient Suppressors of Four-base Codons and Identification of "Shifty" Four-base Codons with a Library Approach in *Escherichia coli*," J Mol Biol Mar. 30, 2001, 307 (3):755-69.
Mahal, LK et al., "Engineering chemical reactivity on cell surfaces through oligosaccharide biosynthesis," Science May 16, 1997: 276(5315):1125-8.
Makrides, SC et al., "Extended in vivo half-life of human soluble complen receptor type 1 fused to a serum albumin-binding receptor," J Pharmacol Exp Ther Apr. 1996; 277(1) 534-42.
Mamot, C et al., "Epidermal growth factor receptor (EGFR)-targeted immunoliposomes mediate specific and efficient drug delivery to EGFR- and EGFRvlll-overexpressing tumor cells," Cancer Res Jun. 15, 2003; 63(12):3154-61.
Mandecki, W "Oligonucleotide-directed double-strand break repair in plasmids of *Escherichia coli*: a method for site-specific mutagenesis," PNAS USA Oct. 1986; 83(19):7177-81.
Mann, SG & LA King. "Efficient transfection of insect cells with baculovirus DNA using electroporation," J Gen Virol Dec. 1989; 70 (Pt 12):3501-5.
Matsoukas, JM et al., "Differences in backbone structure between angiotensin-II angiotensin-II agonists and type I antagonists," J Med Chem Nov. 10, 1995; 38(23):4660-9.
McMinn, DL et al., "Efforts toward Expansion of the Genetic Alphabet: DNA Polymerase Recognition of a High Stable, Self-Pairing Hydrophobic Base," J Am Chem Soc 1999; 121(49):11585-6.
Meggers, E et al., "A Novel Copper-Mediated DNA Base Pair," J Am Chem Soc 2000; 122(43):10714-10715.
Mehvar, R "Modulation of the pharmacokinetics and pharmacodynamics of proteins by polyethylene glycol conjugation" J Pharm Pharm Sci. Jan.-Apr. 2000;3(1): 125-36.
Mendel, D et al., "Site-directed mutagenesis with an expanded genetic code," Annu Rev Biophys Biomol Struct 1995; 24:435-62.
Miller, LK "Baculoviruses as gene expression vectors," Ann Rev Microbiol 1988; 42:177-99.
Miller, LK "Insect baculoviruses: powerful gene expression vectors," Bioessays Oct. 1989;11(4):91-5.
Miller, JC et al., "Flash decaging of tyrosine sidechains in an ion channel," Neuron Apr. 1998;20(4):619-24.

(56) References Cited

OTHER PUBLICATIONS

Minks, C et al., Noninvasive tracing of recombinant proteins with "fluorophenylalanine-fingers," Anal Biochem Aug. 15, 2000; 284(1):29-34.

Miyanohara, A et al., "Expression of hepatitis B surface antigen gene in yeast," PNAS USA Jan. 1983;80(1): 1-5.

Moore, B et al., "Quadruplet codons: implications for code expansion and the specification of translation step size," J Mol Biol 2000; 298(2):195-209.

Mosbach, K et al., "Formation of proinsulin by immobilized Bacillus subtilis," Nature Apr. 1983; 302:543-545.

Nakamaye, KL & Eckstein F. "Inhibition of restriction endonuclease Nci I cleavage by phosphorothioate groups and its application to oligonucleotide-directed mutagenesis," Nucleic Acids Res Dec. 22, 1986; 14(24):9679-98.

Nakatsuka, T., et al., "Peptide segment coupling catalyzed by the semisynthetic enzyme thiosubtilisin," J Am Chem Soc 1987; 109(12): 3808-3810.

Nambiar, KP et al., "Total synthesis and cloning of a gene coding for the ribonuclease S protein," Science (1984) 223: 1299-1301.

Needleman, SB & Wuns CD "A general method applicable to the search for similarities in the amino acid sequence of two proteins," J Mol Biol Mar. 1970; 48(3):443-53.

Neet, KE et al., "Properties of thiol-subtilisin. The consequences of converting the active serine residue to cysteine in a serine proteases," J Biol Chem Dec. 25, 1968; 243(24):6392-401.

Nielsen, UB, et al., "Therapeutic efficacy anti-Erb82 immunoliposomes targeted by a phage antibody selected for cellular endocytosis," Biochim Biophys Acta Aug. 19, 2002; 1591(1-3):109-118.

Nomura, T et al., "Purification, cDNA Cloning, and Expression of UDP-Gal: Glucosylceramide -1,4-Galactosyltransferase from Rat Brain," J Biol Chem 1998; 273(22):13570-7.

Noren, CJ et al., "A general method for site-specific incorporation of unnatural amino acids into proteins," Science Apr. 14, 1989; 244(4901):182-8.

Nowak, MW et al., "Nicotinic receptor binding site probed with unnatural amino acid incorporation in intact cells," Science Apr. 21, 1995; 268(5209):439-42.

Ogawa, AK et al., "Efforts toward the Expansion of the Genetic Alphabet: Information Storage and Replication with Unnatural Hydrophobic Base Pairs," J Am Chem Soc 2000; 122(14):3274-3287.

Ogawa, AK et al., "Rational Design of an Unnatural Base Pair with Increased Kinetic Selectivity," J Am Chem Soc 2000; 122(36); 8803-8804.

Ohtsuka, E et al., "An alternative approach to deoxyoligonucleotides as hybridization probes by insertion of deoxyinosine at ambiguous codon positions," J Biol Chem Mar. 10, 1985; 260(5):2605-8.

Olson et al., "Preparation and Characterization of Poly(ethylene glycol)yated Human Growth Hormone Antagonist," in Poly( ethylene glycol) Chemistry & Biological Applications, 1997; Eds. JM Harris & S. Zalipsky; ACS, Washington D.C., 170-181.

Padwa, A "Intermolecular 1,3-Dipolar Cycloadditions," in Comprehensive Organic Synthesis, vol. 4, (1991) Ed. Trost, B. M.; Pergamon, Oxford, 1069-1109.

Park, JW et al., "Development of anti-p185HER2 immunoliposomes for cancer therapy," PNAS USA Feb. 28, 1995; 92(5):1327-31.

Park, JW et al., "Anti-HER2 immunoliposomes: enhanced efficacy attributable to targeted delivery," Clin Cancer Res Apr. 2002; 8(4):1172-81.

Patnaik, R and JR Swartz "*E. coli*-based in vitro transcription/translation: in vivo-specific synthesis rates and high yields in a batch system," Biotechniques May 1998; 24(5):862-8.

Pearson, WR & DJ Lipman, "Improved tools for biological sequence comparison," PNAS USA Apr. 1988; 85(8):2444-8.

Pepinsky, RB et al., "Improved pharmacokinetic properties of a polyethylene glycol-modified form of interferon- beta-1a with preserved in vitro bioactivity," J Pharmacal Exp Ther Jun. 2001; 297(3):1059-66.

Piccirilli, JA et al., "Enzymatic incorporation of a new base pair into DNA and RNA extends the genetic alphabet," Nature 1990; 343:33-37.

Pintar, A et al. "CX, an algorithm that identifies protruding atoms in proteins," Bioinformatics. Jul. 2002; 18(7):980-4.

Pitha, J et al., "Detergents linked to polysaccharides: preparation and effects on membranes and cells," Eur J Biochem Feb. 15, 1979; 94(1):11-8.

Polgar. L and ML Bender "A new enzyme containing a synthetically formed active site Thiol-subtilisin," J Am Chem Soc 1986: 88(13): 3153-3154.

Pollack, SJ et al., "Introduction of nucleophiles and spectroscopic probes into antibody combining sites," Science Nov. 18, 1988; 242(4881):1038-40.

Preneta, AZ "Separation on the basis of size: gel permeation chromatography," in Protein Purification Methods, a practical approach, 1989; Eds. Harris & Angal; IRL Press, Oxford; 293-306.

Duncan, R "The dawning era of polymer therapeutics," Nat Rev Drug Discov May 2003; 2(5):347-60.

Gaertner, HF & RE Offord, "Site-Specific attachment offunctionalized poly(ethylene glycol) to the amino terminus of proteins," Bioconjug Chem Jan.-Feb. 1996; 7(1):38-44.

Gu, Z et al., "Chromatographic methods for the isolation of, and refolding of proteins from, *Escherichia coli* inclusion bodies," Protein Expr Purif Jun. 2002, 25(1):174-9.

Hohsaka, T & M Sisido, "Incorporation of non-natural amino acids into proteins," Curr Opin Chem Biol Dec. 2002; 6 (6):809-15.

Lilie, H et al., "Advances in refolding of proteins produced in *E. coli*," Curr Opin Biotechnol Oct. 1998; 9(6): 497-501.

Tsumoto, K et al., "Practical considerations in refolding proteins from inclusion bodies," Protein Expr Purif Mar. 2003; 28(1): 1-8.

Wang, W "Instability, stabilization, and formulation of liquid protein pharmaceuticals," Int J Pharm Aug. 20, 1999; 185 (2):129-88.

Debinski, W et al. "A wide range of human cancers express interleukin 4 (IL4) receptors that can be targeted with chimeric toxin composed of IL4 and Pseudomonas exotoxin," J Biol Chem Jul. 5, 1993: 268(19):14065-70.

Goodson RJ & NV Katre, "Site-directed pegylation of recombinant interleukin-2 at its glycosylation site," Biotechnology (NY) Apr. 1990; 8(4):343-6.

Van Hest, JC and DA Tirrell, "Efficient introduction of alkene functionality into proteins in vivo," FEBS Lett. May 22, 1996:428( 1-2):68-70.

Andresz, H et al., "Chemische Synthese verzweigter Polysaccharide, 5; Kopplung von Oligosachariden und Amylose an verschiedene Trager durch Hydrazonbindung," Makromol. Chem. 1978; 179:301 (Abstract).

Rowles, J et al., "Cloning and characterization of PDKA on 7q21.3 encoding a fourth pyruvate dehydrogenase kinasa iscenzyme in human," J Biol Chem Sep. 13, 1996; 271(37):22376-82.

Frokjaer, et al., "Protein Drug Stability: A Formulation Challenge". Nature Reviews, Drug Discovery. Apr. 30, 2005, vol. 4, pp. 298-306.

CN Application No. 201180045228.7, 2nd Office Action issued Jul. 10, 2014, with English Translation.

KR Application 10-2013-7007318, Notice of Preliminary Rejection issued Jul. 28, 2014, with English Translation.

McNally, et al (editors), "Physical Considerations in Protein and Peptide Stability", Protein Formulation and Delivery, Second Edition, 2008, pp. 53-54.

Mashimo, et al., "Quantitative analysis of aggregation-solubility relationship by in-silico solubility prediction", Journal of High Throughput Screening, 2010, 1 pp. 99-107.

Bondos, et al., "Detection and prevention of protein aggregation before, during, and after purification", Analytical Biochemistry, 2003, vol. 316, pp. 223-231.

Treuheit, M.J. et al. Inverse relationship of protein concentration and aggregation. Pharmaceutical Research, 2002. vol. 19, No. 4, p. 511-516.

Rajan. R.S. et al Modulation of protein aggregation by polyethylene glycol conjugation: GCSF as a case study. Protein Science, 2006, 15:1063-1075.

(56) References Cited

OTHER PUBLICATIONS

Cohen et al., "In vivo stimulation of granulopoiesis by recombinant human granulocyte colony-stimulating factor," Proc. Natl. Acad. Sci. 1987; 84: 2484-2488.
Heidari et al., "Expression, purification, and in vivo biological activities of recombinant bovine granulocyte-colony stimulating factor," Vet. Immol. Imunopathol, 2001; 81:45-57.
Weisbart, R. H., et al., "Colony-Stimulating Factors and Host Defense," Annals of Internal Medicine 1989: 110:297-303.
S. Kitagawa, et al., "Recombinant Human Granulocyte Colony-Stimulating Factor Enhances Superoxide Release In Human Granulocytes Stimulated By The Chemotactic Peptide," Biochem. Biophys. Res. Commun. 1987; 144:1143-1146.
C. F. Nathan, "Respiratory burst in adherent human neutrophils: triggering by colony-stimulating factors CSF-GM and CSF-G," Blood 1989: 74:301-306.
Weisbart, R. H., et al., "GM-CSF induces human neutrophil IgA-mediated phagocytosis by an IgA Fc receptor activation mechanism," Nature 1988; 332: 647-649.
Souza, L. et al., "Recombinant Human Granulocyte Colony-Stimulating Factor: Effects on Normal and Leukemie Myeloid Cells," Science 232, 61-65 (1986).
Piedmonte et al., Advanced Drug Delivery Reviews, 60: 50-58 (2008).
Herman et al., "Characterization, Formulation, and Stability of Neupogen® (Filgrastim), a Recombinant Human Granulocyte-Colony Stimulating Factor," in Formulation, Characterization, and Stability of Protein Drags, Rodney Pearlman and Y. John Wang, eds., Plenum Press, New York (1996).
Remington's Pharmaceutical Sciences, 17th ed. 1985)).
Pikal, M. "Freeze-Drying of Proteins Part II: Formulation Selection," Biopharm. 3(9)26-30 (1990).
Arakawa et al. "Protein-Solvent Interactions in Pharmaceutical Formulations," Pharm Res. 8(3):285-291 (1991).
Broadhead, J. et al., "The Spray Drying of Pharmaceuticals," in Drug Dev. Ind. Pharm. 18 (11 & 12), 1169-1206 (1992).
Heidari M, et al. Cloning, sequencing, and analysis of cDNA encoding bovine granulocyte-oolongy stimulating factor, Veterinary Immunology and Immunopathology, 2000, vol. 73, p. 183-191.
International Preliminary Report on Patentability and the Written Opinion of the International Searching Authority issued Mar. 26, 2013 in PCT/US2011/052692 (WO 2012/040421).
International Search Report dated Sep. 23, 2010 in PCT/US2011/052692 (WO 2012/040421).
Moore et al., "Synergy of interleukin 1 and granulocyte colony-stimulating factor; in vivo stimulation of stem-cell recovery and hematopoietic regeneration following 5-fluorouracil treatment of mice", PNAS USA (1987) 84 (20):7134-7138.
Morrison et al., "Transfer and expression of immunoglobulin genes", Ann. Rev. Immunol. (1984) 2:239-256.
Mollet al., "Four-Helix Bundle Growth Factors and their receptors: protein-protein interactions", Current Opinion in Structural Biology (1985) 5:114-121.
Murakami, "Using a Solid-Phase Ribozyme Aminoacylation System Reprogram the Genetic Code", Chemistry and Biology 2003, 10:1077-1084.
Nagata et al., "Molecular cloning and expression of cDNA for human granulocyte colony-stimulating factor", Nature (1986) 319(6052):415-418.
Nagata et al., "The chromosomal gene structure and two mRNAs for human granulocyte colony-stimulating factor", EMBO (1986) 5(3):575-581.
Accession No. Q8N4W3 (Q8N4W3_Human), Colony stimulating factor 3 (Granulocyte) [online]. UniProtKB/TrEMBL, 2009 [retrieved on Jan. 12, 2010]. Retrieved from the Internet:< http://www.uniprot.org/uniprot/Q8N4W3>.
Gerhard et al,. (2004) "The status, quality, and expansion of the NIH full-length cDNA project: the Mammalian Gene Collection (MGC)," Genome Res. 14(108): 2121-7 (Abstract only).
Accession No. P35833.2 Granulocyte colony-stimulating factor [online]. UniProtKB/TrEMBL, 2001 [retrieved Dec. 12, 2013]. Retrieved from the Internet: <http://www.uniprot.org/uniprot/P35833.txt>.
Cho et al., (2011) "Optimized clinical performance of growth hormone with an expanded genetic code," PNAS 108(22): 9060-5. doi: 10.1073/pnas. 1100387108. Epub May 11, 2011.
Adams et al., "Molecular cloning of mouse immunobulin heavy chain messenger ribonucleic acids coding for mu, alpha, gamma 1, gamma 28, and gamma 3 chains", Biochemistry (1980) 19(12):2711-2719.
Bain et al., "Ribosome-mediated incorporation of a non-standard amino acid into a peptide through expansion of the genetic code", Nature (1992) 356:537-539.
Bazan, "Structural Design and Molecular Evolution of a Cytokine Receptor Superfamily", PNAS. USA (1990) 87:6934-6938.
Bazan, "Unraveling the Structure of IL-2", Science (1992) 257: 410-413.
Bazan, "Haemopoietic receptors and helical cytokines", Immunology Today (1990) 11(10):350-354.
Behrens et al., "Structure of Human Serum Albumin", Fed. Proc. (1975) 34:591.
Bensinger, et al. "Autologous transplantation with peripheral blood mononuclear cells collected after administration of recombinant granulocyte stimulating factor", (1993) Blood 81 (11): 3158-3163.
Bowen et al., "Relationship between molecular mass and duration of activity of polyethylene glycol conjugated granulocyle colony-stimulating factor mutein", Experimental Hematology (1999) 27(3):425-432.
Palva, I et al., "Secretion of interferon by Bacillus subtilis," Gene May-Jun. 1983; 22(2-3):229-35.
Beaucage, SL & MH Caruthers, "Deoxynucleoside Phosphoramidites-A New Class of key Intermediates for Deoxypolynucleotide Synthesis", Tetrahedron Letts (1981) 22(20):1859-1862.
Cate et al., "Isolation of the Bovine and Human Genes for Mullerian thibiting Substance And Expression of the Human Gene In Animal Cells", Cell (1986) 45(5):685-698.
Cech, "The Chemistry of Splicing RNA and RNA Enzymes", Science, (1987) 236(4808):1532-1539.
Chiba et al. "Tryptophan residue of Trp-Ser-X-Trp-Ser motif in extracellular domains of erythropoietin receptor is essential for signal transduction," Biochim. Biophys. Res. Comm. (1992) 184:485-490.
Coloma, "Novel vectors for the expression of antibody molecules using variable regions generated by polymerase chain reaction", J. Imm. Methods (1992) 152(1):89-104.
Devlin et al., "Expression of Granulocyte Colony-Stimulating Factor by Human Cell Lines", J. Leukoc. Biol (1987) 41:302-306.
Diederichs et al. "Novel fold and putative receptor binding site of granulocyte-macrophage colony-stimulating factor," Science (1991) 154:1779-1782.
Dolby et al., "Cloning and partial nucleotide sequence of human immunoglobulin mu chain cDNA from B cells and mouse-human hybridomas", Proc. Natl. Acad. Sci. USA (1980) 77(10):6027-6031.
Drummond et al., "Liposomal drug delivery systems for cancer therapy", Teicher B (ad): Cancer Drug Discovery and Development (2002) 191-213.
Dzau et al., "Gene era rdiovascular disease", Trends in Biotechnology. (1993) 11(5):205-210.
Edwards et al., "A bacterial amber suppressor in *Saccharomyces cerevisiae* is selectively recognized by a bacterial aminoacyl-tRNA synthetase", Mol. Cell. Biol. (1990) 10(4):1633-1641.
Egei-Mitani et al.. "A novel aspartyl protease allowing KEX2-independent MF alpha propheromone processing in yeast", Yeast (1990) 6(2):127-137.
Falkner et al,. "Expression of mouse immunoglobulin genes in monkey cells", Nature (1982) 298(5871):286-288.
Friesen et al., "The Regulation of Baculovirus Gene Expression", Current Topics in Microbiology and Immunology (1986) 131:31-49.
Gabrilove, "Introduction and overview of hematopoietic growth factors", Seminars in Hematology (1989), 26(2 Suppl 2):1-13.

(56) References Cited

OTHER PUBLICATIONS

Gough et al. "Molecular Cloning of Seven Mouse Immunoglobulin K Chain Messenger Ribonucleic Acids", Biochemistry (1980) 19:2702-2710.

Hagenbuchle et al., "Mouse liver and salivary gland alpha-amylase mRNAs differ only in 5' non-translated sequences", Nature (1981) 289(5799):643-646.

Hecht et al., "Chemical Aminoacylation if tRNA's", J. Biol. Chem. (1978) 253(13):4517-4520.

Hecht, "Probing the Synthetic Capabilities of a Center of Biochemical Catalysis", Acc. Chem. Res. (1992) 25 (12):545-552.

Heckler et al., "Ribosomal binding and dipeptide formation by misacylaled tRNA(Phe)'s", Biochemistry (1988) 27 (19):7254-7262.

Hill et al. "The Structure of Granulocyte-Colony-Stimulating Factor and its Relationship to Other Growth Factors," PNAS USA (1993) 90:5167-71.

Illangakekare et al., "Aminoacyl-RNA Synthesis Catalyzed by an RNA", Science (1995) 267(5198):643-647.

Jones et al., "Growth factors in haemopoiesis", Bailliere's Clinical Hematology (1989) 2(1):83-111.

Kehrli et al., "Alterations in bovine neutrophil function during the periparturient period", Am. J. Vet. Res. (1989) 50 (2):207-214.

Kehrti et al., "Immunobiology of hematopoietic colony-stimulating factors: potential application to disease prevention in the bovine", J. Dairy Sci (1991) 74(12):4399-4412.

Kourouklis et al., "Programmable ribozymes for mischarging tRNA with nonnatural amino acids and the applications to translation", Methods (2005) 36:239-244.

Kowal et al., "Exploiting unassigned codons in Micrococcus ltueus for tRNA-based amino acid mutagenesis", Nucl. Acid. Res. (1997) 25(22):4685-4689.

Kowal et al., "Twenty-first aminoacyl synthetase-suppressor tRNA pairs for possible use in site-specific incorporation of amino acid analogues into proteins in eukaryotes and in eubacteria", PNAS USA (2001) 98 (5):2268-2273.

Lawn et al., "The sequence of human serum albumin cDNA and its expression in E. coli", Nucleic Acids Research (1981) 9(22):6102-6114.

Layton et al. "Identification of a ligand-binding site on the granulocyte colony-stimulating factor receptor by molecular and mutagenesis", J Biol Chem (1997) 272(47):29735-29741.

Layton et al. "Identification and ligand-binding site III on the immunoglobulin-like domain of the granulocyte colony- stimulating factor receptor", J Biol Chem (2001) 276(39):36779-36787.

Lohse et al., "Ribozyme-catalysed amino-acid transfer reactions", Nature (1996) 381:442-444.

Lu et al., "Site-specific incorporation of a Phosphotyrosine Mimetic Reveals a Role for Tyrosine Phosphorylation of SHP-2 in Cell Signaling", Mol Cell. (2001) 8(4):759-69.

Matsumoto et al., "Protective effect of human granulocyte colony-stimulating factor on microbial infection in neutropenic mice", Infect. Inmun. (1987) 55(11 ):2715-2720.

McCorkle et al., "RNA's as Catalysts: A New Class of Enzymes", Concepts Biochem. (1987) 64(3):221-226.

McKay, "Response", (1992) 257:412-413.

Meloun et al., "Complete amino acid sequence of human serum albumin", FEBS Letters (1975) 58(1):134-7.

Minghetti et al., "Molecular structure of the human albumin gene is revealed by nucleotide sequence within q11-22 of chromosome 4", J Biol Chem (1986) 261(15):6747-57.

Neben et al. "Mobilization of hematopoietic stem and progenitor cell subpopulations from the marrow to the blood of mice following cyclophosphamide and/or granulocyte colony-stimulating factor", Blood (1993) 61(7):1960-1967.

Needham-VanDevanter et al., "Characterization of an adduct between CC-1065 and a Defined Oligodeoxynucleotide Duplex", Nucleic Acids Res., (1984) 12(15):6159-6168.

Nicola et al. "Separation of Functionally Distinct Human Granylocyte-Macrophage Colony-Stimulating Factors", Blood (1979) 54:614-627.

\* cited by examiner

```
SEQUENCE LISTING

<160> NUMBER OF SEQ ID NOS: 14

<210> SEQ ID NO 1
<211> LENGTH: 174
<212> TYPE: PRT
<213> ORGANISM: Bos taurus

<400> SEQUENCE: 1

Thr Pro Leu Gly Pro Ala Arg Ser Leu Pro Gln Ser Phe Leu Leu Lys
1               5                   10                  15

Cys Leu Glu Gln Val Arg Lys Ile Gln Ala Asp Gly Ala Glu Leu Gln
            20                  25                  30

Glu Arg Leu Cys Ala Ala His Lys Leu Cys His Pro Glu Glu Leu Met
        35                  40                  45

Leu Leu Arg His Ser Leu Gly Ile Pro Gln Ala Pro Leu Ser Ser Cys
    50                  55                  60

Ser Ser Gln Ser Leu Gln Leu Thr Ser Cys Leu Asn Gln Leu His Gly
65                  70                  75                  80

Gly Leu Phe Leu Tyr Gln Gly Leu Leu Gln Ala Leu Ala Gly Ile Ser
                85                  90                  95

Pro Glu Leu Ala Pro Thr Leu Asp Thr Leu Gln Leu Asp Val Thr Asp
            100                 105                 110

Phe Ala Thr Asn Ile Trp Leu Gln Met Glu Asp Leu Gly Ala Ala Pro
        115                 120                 125

Ala Val Gln Pro Thr Gln Gly Ala Met Pro Thr Phe Thr Ser Ala Phe
    130                 135                 140

Gln Arg Arg Ala Gly Gly Val Leu Val Ala Ser Gln Leu His Arg Phe
145                 150                 155                 160

Leu Glu Leu Ala Tyr Arg Gly Leu Arg Tyr Leu Ala Glu Pro
                165                 170

<210> SEQ ID NO 2
<211> LENGTH: 175
<212> TYPE: PRT
<213> ORGANISM: Bos taurus

<400> SEQUENCE: 2

Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
            20                  25                  30

Gln Glu Arg Leu Cys Ala Ala His Lys Leu Cys His Pro Glu Glu Leu
        35                  40                  45
```

Met Leu Leu Arg His Ser Leu Gly Ile Pro Gln Ala Pro Leu Ser Ser
 50                  55                  60

Cys Ser Ser Gln Ser Leu Gln Leu Thr Ser Cys Leu Asn Gln Leu His
 65                  70                  75                  80

Gly Gly Leu Phe Leu Tyr Gln Gly Leu Leu Gln Ala Leu Ala Gly Ile
                 85                  90                  95

Ser Pro Glu Leu Ala Pro Thr Leu Asp Thr Leu Gln Leu Asp Val Thr
                100                 105                 110

Asp Phe Ala Thr Asn Ile Trp Leu Gln Met Glu Asp Leu Gly Ala Ala
                115                 120                 125

Pro Ala Val Gln Pro Thr Gln Gly Ala Met Pro Thr Phe Thr Ser Ala
        130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175

<210> SEQ ID NO 3
<211> LENGTH: 175
<212> TYPE: PRT
<213> ORGANISM: Bos taurus
<220> FEATURE:
<221> NAME/KEY: misc_feature
<222> LOCATION: (9)..(9)
<223> OTHER INFORMATION: wherein Xaa is para-acetylphenylalanine (pAF)

<400> SEQUENCE: 3

Met Thr Pro Leu Gly Pro Ala Arg Xaa Leu Pro Gln Ser Phe Leu Leu
1               5                   10                  15

Lys Cys Leu Glu Gln Val Arg Lys Ile Gln Ala Asp Gly Ala Glu Leu
                20                  25                  30

Gln Glu Arg Leu Cys Ala Ala His Lys Leu Cys His Pro Glu Glu Leu
            35                  40                  45

Met Leu Leu Arg His Ser Leu Gly Ile Pro Gln Ala Pro Leu Ser Ser
 50                  55                  60

Cys Ser Ser Gln Ser Leu Gln Leu Thr Ser Cys Leu Asn Gln Leu His
 65                  70                  75                  80

Gly Gly Leu Phe Leu Tyr Gln Gly Leu Leu Gln Ala Leu Ala Gly Ile
                 85                  90                  95

Ser Pro Glu Leu Ala Pro Thr Leu Asp Thr Leu Gln Leu Asp Val Thr
                100                 105                 110

Asp Phe Ala Thr Asn Ile Trp Leu Gln Met Glu Asp Leu Gly Ala Ala
                115                 120                 125

Pro Ala Val Gln Pro Thr Gln Gly Ala Met Pro Thr Phe Thr Ser Ala
        130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175

<210> SEQ ID NO 4
<211> LENGTH: 175
<212> TYPE: PRT
<213> ORGANISM: Bos taurus
<220> FEATURE:
<221> NAME/KEY: misc_feature
<222> LOCATION: (63)..(63)
<223> OTHER INFORMATION: wherein Xaa is para-acetylphenylalanine (pAF)

<400> SEQUENCE: 4

Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
                20                  25                  30

Gln Glu Arg Leu Cys Ala Ala His Lys Leu Cys His Pro Glu Glu Leu
            35                  40                  45

Met Leu Leu Arg His Ser Leu Gly Ile Pro Gln Ala Pro Leu Xaa Ser
50                  55                  60

Cys Ser Ser Gln Ser Leu Gln Leu Thr Ser Cys Leu Asn Gln Leu His
65                  70                  75                  80

Gly Gly Leu Phe Leu Tyr Gln Gly Leu Leu Gln Ala Leu Ala Gly Ile
                85                  90                  95

Ser Pro Glu Leu Ala Pro Thr Leu Asp Thr Leu Gln Leu Asp Val Thr
                100                 105                 110

Asp Phe Ala Thr Asn Ile Trp Leu Gln Met Glu Asp Leu Gly Ala Ala
            115                 120                 125

Pro Ala Val Gln Pro Thr Gln Gly Ala Met Pro Thr Phe Thr Ser Ala
130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175

<210> SEQ ID NO 5
<211> LENGTH: 175
<212> TYPE: PRT
<213> ORGANISM: Bos taurus
<220> FEATURE:
<221> NAME/KEY: misc_feature
<222> LOCATION: (70)..(70)
<223> OTHER INFORMATION: wherein Xaa is para-acetylphenylalanine (pAF)

<400> SEQUENCE: 5

Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
                20                  25                  30

Gln Glu Arg Leu Cys Ala Ala His Lys Leu Cys His Pro Glu Glu Leu
            35                  40                  45

Met Leu Leu Arg His Ser Leu Gly Ile Pro Gln Ala Pro Leu Ser Ser
50                  55                  60

Cys Ser Ser Gln Ser Xaa Gln Leu Thr Ser Cys Leu Asn Gln Leu His
65                  70                  75                  80

Gly Gly Leu Phe Leu Tyr Gln Gly Leu Leu Gln Ala Leu Ala Gly Ile
                85                  90                  95

Ser Pro Glu Leu Ala Pro Thr Leu Asp Thr Leu Gln Leu Asp Val Thr
                100                 105                 110

Asp Phe Ala Thr Asn Ile Trp Leu Gln Met Glu Asp Leu Gly Ala Ala
            115                 120                 125

Pro Ala Val Gln Pro Thr Gln Gly Ala Met Pro Thr Phe Thr Ser Ala
130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro

```
                        165                 170                 175

<210> SEQ ID NO 6
<211> LENGTH: 175
<212> TYPE: PRT
<213> ORGANISM: Bos taurus
<220> FEATURE:
<221> NAME/KEY: misc_feature
<222> LOCATION: (126)..(126)
<223> OTHER INFORMATION: wherein Xaa is para-acetylphenylalanine (pAF)

<400> SEQUENCE: 6

Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
                20                  25                  30

Gln Glu Arg Leu Cys Ala Ala His Lys Leu Cys His Pro Glu Glu Leu
            35                  40                  45

Met Leu Leu Arg His Ser Leu Gly Ile Pro Gln Ala Pro Leu Ser Ser
        50                  55                  60

Cys Ser Ser Gln Ser Leu Gln Leu Thr Ser Cys Leu Asn Gln Leu His
65                  70                  75                  80

Gly Gly Leu Phe Leu Tyr Gln Gly Leu Leu Gln Ala Leu Ala Gly Ile
                85                  90                  95

Ser Pro Glu Leu Ala Pro Thr Leu Asp Thr Leu Gln Leu Asp Val Thr
                100                 105                 110

Asp Phe Ala Thr Asn Ile Trp Leu Gln Met Glu Asp Leu Xaa Ala Ala
            115                 120                 125

Pro Ala Val Gln Pro Thr Gln Gly Ala Met Pro Thr Phe Thr Ser Ala
        130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175

<210> SEQ ID NO 7
<211> LENGTH: 175
<212> TYPE: PRT
<213> ORGANISM: Bos taurus
<220> FEATURE:
<221> NAME/KEY: misc_feature
<222> LOCATION: (134)..(134)
<223> OTHER INFORMATION: wherein Xaa is para-acetylphenylalanine (pAF)

<400> SEQUENCE: 7

Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
                20                  25                  30

Gln Glu Arg Leu Cys Ala Ala His Lys Leu Cys His Pro Glu Glu Leu
            35                  40                  45

Met Leu Leu Arg His Ser Leu Gly Ile Pro Gln Ala Pro Leu Ser Ser
        50                  55                  60

Cys Ser Ser Gln Ser Leu Gln Leu Thr Ser Cys Leu Asn Gln Leu His
65                  70                  75                  80

Gly Gly Leu Phe Leu Tyr Gln Gly Leu Leu Gln Ala Leu Ala Gly Ile
                85                  90                  95

Ser Pro Glu Leu Ala Pro Thr Leu Asp Thr Leu Gln Leu Asp Val Thr
                100                 105                 110
```

```
Asp Phe Ala Thr Asn Ile Trp Leu Gln Met Glu Asp Leu Gly Ala Ala
            115                 120                 125

Pro Ala Val Gln Pro Xaa Gln Gly Ala Met Pro Thr Phe Thr Ser Ala
        130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175

<210> SEQ ID NO 8
<211> LENGTH: 175
<212> TYPE: PRT
<213> ORGANISM: Bos taurus
<220> FEATURE:
<221> NAME/KEY: misc_feature
<222> LOCATION: (137)..(137)
<223> OTHER INFORMATION: wherein Xaa is para-acetylphenylalanine (pAF)

<400> SEQUENCE: 8

Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
            20                  25                  30

Gln Glu Arg Leu Cys Ala Ala His Lys Leu Cys His Pro Glu Glu Leu
        35                  40                  45

Met Leu Arg His Ser Leu Gly Ile Pro Gln Ala Pro Leu Ser Ser
    50                  55                  60

Cys Ser Ser Gln Ser Leu Gln Leu Thr Ser Cys Leu Asn Gln Leu His
65                  70                  75                  80

Gly Gly Leu Phe Leu Tyr Gln Gly Leu Leu Gln Ala Leu Ala Gly Ile
                85                  90                  95

Ser Pro Glu Leu Ala Pro Thr Leu Asp Thr Leu Gln Leu Asp Val Thr
            100                 105                 110

Asp Phe Ala Thr Asn Ile Trp Leu Gln Met Glu Asp Leu Gly Ala Ala
        115                 120                 125

Pro Ala Val Gln Pro Thr Gln Gly Xaa Met Pro Thr Phe Thr Ser Ala
    130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175

<210> SEQ ID NO 9
<211> LENGTH: 175
<212> TYPE: PRT
<213> ORGANISM: Bos taurus
<220> FEATURE:
<221> NAME/KEY: misc_feature
<222> LOCATION: (9)..(9)
<223> OTHER INFORMATION: wherein Xaa is para-acetylphenylalanine (pAF)
      linked to a poly(ethylene glycol) moiety

<400> SEQUENCE: 9

Met Thr Pro Leu Gly Pro Ala Arg Xaa Leu Pro Gln Ser Phe Leu Leu
1               5                   10                  15

Lys Cys Leu Glu Gln Val Arg Lys Ile Gln Ala Asp Gly Ala Glu Leu
            20                  25                  30

Gln Glu Arg Leu Cys Ala Ala His Lys Leu Cys His Pro Glu Glu Leu
        35                  40                  45
```

```
Met Leu Leu Arg His Ser Leu Gly Ile Pro Gln Ala Pro Leu Ser Ser
    50                  55                  60

Cys Ser Ser Gln Ser Leu Gln Leu Thr Ser Cys Leu Asn Gln Leu His
 65                  70                  75                  80

Gly Gly Leu Phe Leu Tyr Gln Gly Leu Leu Gln Ala Leu Ala Gly Ile
                 85                  90                  95

Ser Pro Glu Leu Ala Pro Thr Leu Asp Thr Leu Gln Leu Asp Val Thr
                100                 105                 110

Asp Phe Ala Thr Asn Ile Trp Leu Gln Met Glu Asp Leu Gly Ala Ala
                115                 120                 125

Pro Ala Val Gln Pro Thr Gln Gly Ala Met Pro Thr Phe Thr Ser Ala
                130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175

<210> SEQ ID NO 10
<211> LENGTH: 175
<212> TYPE: PRT
<213> ORGANISM: Bos taurus
<220> FEATURE:
<221> NAME/KEY: misc_feature
<222> LOCATION: (63)..(63)
<223> OTHER INFORMATION: wherein Xaa is para-acetylphenylalanine (pAF)
      linked to a poly(ethylene glycol) moiety

<400> SEQUENCE: 10

Met Thr Pro Leu Gly Pro Ala Arg Ser Leu Pro Gln Ser Phe Leu Leu
  1               5                  10                  15

Lys Cys Leu Glu Gln Val Arg Lys Ile Gln Ala Asp Gly Ala Glu Leu
                 20                  25                  30

Gln Glu Arg Leu Cys Ala Ala His Lys Leu Cys His Pro Glu Glu Leu
             35                  40                  45

Met Leu Leu Arg His Ser Leu Gly Ile Pro Gln Ala Pro Leu Xaa Ser
 50                  55                  60

Cys Ser Ser Gln Ser Leu Gln Leu Thr Ser Cys Leu Asn Gln Leu His
 65                  70                  75                  80

Gly Gly Leu Phe Leu Tyr Gln Gly Leu Leu Gln Ala Leu Ala Gly Ile
                 85                  90                  95

Ser Pro Glu Leu Ala Pro Thr Leu Asp Thr Leu Gln Leu Asp Val Thr
                100                 105                 110

Asp Phe Ala Thr Asn Ile Trp Leu Gln Met Glu Asp Leu Gly Ala Ala
                115                 120                 125

Pro Ala Val Gln Pro Thr Gln Gly Ala Met Pro Thr Phe Thr Ser Ala
                130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175

<210> SEQ ID NO 11
<211> LENGTH: 175
<212> TYPE: PRT
<213> ORGANISM: Bos taurus
<220> FEATURE:
<221> NAME/KEY: misc_feature
<222> LOCATION: (70)..(70)
```

<223> OTHER INFORMATION: wherein Xaa is para-acetylphenylalanine (pAF)
linked to a poly(ethylene glycol) moiety

<400> SEQUENCE: 11

```
Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
            20                  25                  30

Gln Glu Arg Leu Cys Ala Ala His Lys Leu Cys His Pro Glu Glu Leu
        35                  40                  45

Met Leu Leu Arg His Ser Leu Gly Ile Pro Gln Ala Pro Leu Ser Ser
    50                  55                  60

Cys Ser Ser Gln Ser Xaa Gln Leu Thr Ser Cys Leu Asn Gln Leu His
65                  70                  75                  80

Gly Gly Leu Phe Leu Tyr Gln Gly Leu Leu Gln Ala Leu Ala Gly Ile
                85                  90                  95

Ser Pro Glu Leu Ala Pro Thr Leu Asp Thr Leu Gln Leu Asp Val Thr
            100                 105                 110

Asp Phe Ala Thr Asn Ile Trp Leu Gln Met Glu Asp Leu Gly Ala Ala
        115                 120                 125

Pro Ala Val Gln Pro Thr Gln Gly Ala Met Pro Thr Phe Thr Ser Ala
    130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175
```

<210> SEQ ID NO 12
<211> LENGTH: 175
<212> TYPE: PRT
<213> ORGANISM: Bos taurus
<220> FEATURE:
<221> NAME/KEY: misc_feature
<222> LOCATION: (126)..(126)
<223> OTHER INFORMATION: wherein Xaa is para-acetylphenylalanine (pAF)
linked to a poly(ethylene glycol) moiety

<400> SEQUENCE: 12

```
Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
            20                  25                  30

Gln Glu Arg Leu Cys Ala Ala His Lys Leu Cys His Pro Glu Glu Leu
        35                  40                  45

Met Leu Leu Arg His Ser Leu Gly Ile Pro Gln Ala Pro Leu Ser Ser
    50                  55                  60

Cys Ser Ser Gln Ser Leu Gln Leu Thr Ser Cys Leu Asn Gln Leu His
65                  70                  75                  80

Gly Gly Leu Phe Leu Tyr Gln Gly Leu Leu Gln Ala Leu Ala Gly Ile
                85                  90                  95

Ser Pro Glu Leu Ala Pro Thr Leu Asp Thr Leu Gln Leu Asp Val Thr
            100                 105                 110

Asp Phe Ala Thr Asn Ile Trp Leu Gln Met Glu Asp Leu Xaa Ala Ala
        115                 120                 125

Pro Ala Val Gln Pro Thr Gln Gly Ala Met Pro Thr Phe Thr Ser Ala
    130                 135                 140

Phe Gln Arg Arg Ala Gly Gly Val Leu Val Ala Ser Gln Leu His Arg
```

```
145                 150                 155                 160

Phe Leu Glu Leu Ala Tyr Arg Gly Leu Arg Tyr Leu Ala Glu Pro
                165                 170                 175

<210> SEQ ID NO 13
<211> LENGTH: 175
<212> TYPE: PRT
<213> ORGANISM: Bos taurus
<220> FEATURE:
<221> NAME/KEY: misc_feature
<222> LOCATION: (134)..(134)
<223> OTHER INFORMATION: wherein Xaa is para-acetylphenylalanine (pAF)
      linked to a poly(ethylene glycol) moiety

<400> SEQUENCE: 13

Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
                20                  25                  30

Gln Glu Arg Leu Cys Ala Ala His Lys Leu Cys His Pro Glu Glu Leu
            35                  40                  45

Met Leu Leu Arg His Ser Leu Gly Ile Pro Gln Ala Pro Leu Ser Ser
    50                  55                  60

Cys Ser Ser Gln Ser Leu Gln Leu Thr Ser Cys Leu Asn Gln Leu His
65                  70                  75                  80

Gly Gly Leu Phe Leu Tyr Gln Gly Leu Leu Gln Ala Leu Ala Gly Ile
                85                  90                  95

Ser Pro Glu Leu Ala Pro Thr Leu Asp Thr Leu Gln Leu Asp Val Thr
            100                 105                 110

Asp Phe Ala Thr Asn Ile Trp Leu Gln Met Glu Asp Leu Gly Ala Ala
        115                 120                 125

Pro Ala Val Gln Pro Xaa Gln Gly Ala Met Pro Thr Phe Thr Ser Ala
    130                 135                 140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165                 170                 175

<210> SEQ ID NO 14
<211> LENGTH: 175
<212> TYPE: PRT
<213> ORGANISM: Bos taurus
<220> FEATURE:
<221> NAME/KEY: misc_feature
<222> LOCATION: (137)..(137)
<223> OTHER INFORMATION: wherein Xaa is para-acetylphenylalanine (pAF)
      linked to a poly(ethylene glycol) moiety

<400> SEQUENCE: 14

Met Thr Pro Leu Gly Pro Ala Arg Ser Leu Pro Gln Ser Phe Leu Leu
1               5                   10                  15

Lys Cys Leu Glu Gln Val Arg Lys Ile Gln Ala Asp Gly Ala Glu Leu
                20                  25                  30

Gln Glu Arg Leu Cys Ala Ala His Lys Leu Cys His Pro Glu Glu Leu
            35                  40                  45

Met Leu Leu Arg His Ser Leu Gly Ile Pro Gln Ala Pro Leu Ser Ser
    50                  55                  60

Cys Ser Ser Gln Ser Leu Gln Leu Thr Ser Cys Leu Asn Gln Leu His
65                  70                  75                  80
```

```
Gly Gly Leu Phe Leu Tyr Gln Gly Leu Leu Gln Ala Leu Ala Gly Ile
            85                   90                   95

Ser Pro Glu Leu Ala Pro Thr Leu Asp Thr Leu Gln Leu Asp Val Thr
            100                  105                  110

Asp Phe Ala Thr Asn Ile Trp Leu Gln Met Glu Asp Leu Gly Ala Ala
        115                  120                  125

Pro Ala Val Gln Pro Thr Gln Gly Xaa Met Pro Thr Phe Thr Ser Ala
        130                 135             140

Phe Gln Arg Arg Ala Gly Gly Val Leu Val Ala Ser Gln Leu His Arg
145                 150                 155                 160

Phe Leu Glu Leu Ala Tyr Arg Gly Leu Arg Tyr Leu Ala Glu Pro
                165             170                 175
```

FORMULATIONS FOR BOVINE GRANULOCYTE COLONY STIMULATING FACTOR AND VARIANTS THEREOF

CROSS-REFERENCE TO RELATED APPLICATIONS

This application is a continuation of U.S. application Ser. No. 13/239,493 filed on Sep. 22, 2011, and claims the benefit of U.S. Provisional Application No. 61/385,629 filed on Sep. 23, 2010, the disclosures of which are incorporated by reference herein in its entirety.

Granulocyte Colony Stimulating Factor (G-CSF) is a member of the growth hormone supergene family. G-CSF stimulates the proliferation of specific bone marrow precursor cells and their differentiation into granulocytes. Furthermore, G-CSF is a potent stimulus for neutrophil proliferation and maturation in vivo (Cohen et al., Proc. Natl. Acad. Sci. 1987; 84: 2484-2488; see also Heidari et al., Vet. Immol. Imunopathol. 2001; 81:45-57). G-CSF is also capable of inducing functional activation or "priming" of mature neutrophils in vitro (Weisbart, R. H. et al., Annals of Internal Medicine 1989; 110:297-303). G-CSF has been shown to prime human granulocytes and enhance superoxide release stimulated by the chemotactic peptide N-formyl-methionyl-leucyl-phenalalanine (S. Kitagawa, et al., Biochem. Biophys. Res. Commun. 1987; 144:1143-1146, and C. F. Nathan, Blood 1989; 74:301-306), and to activate human neutrophil IgA mediated phagocytosis (Weisbart, R. H., et al., Nature 1988; 332: 647-649).

G-CSF has been found to be useful in the treatment of indications where an increase in neutrophils will provide benefits. G-CSF is also useful alone, or in combination with other compounds (such as other cytokines) for growth or expansion of cells in culture, for example, for bone marrow transplants.

The cDNA cloning and expression of recombinant human G-CSF (hG-CSF) has been described, and the recombinant hG-CSF exhibits most, if not all, of the biological properties of the native molecule (Souza, L et al., Science 232, 61-65 (1986)). Sequence analysis of the cDNA and genomic DNA clones has allowed the deduction of the amino acid sequence and reveals that the protein is 204 amino acids long with a signal sequence of 30 amino acids. The mature protein is 174 amino acids long and possesses no potential N-linked glycosylation sites but several possible sites for O-linked glycosylation.

Pharmaceutical preparations containing hG-CSF are known in the art and include numerous formulations. For example, various formulations of hG-CSF are described in Piedmonte et al., Advanced Drug Delivery Reviews, 60: 50-58 (2008), Herman et al., in Formulation, Characterization, and Stability of Protein Drugs, Rodney Pearlman and Y. John Wang, eds., Plenum Press, New York (1996), U.S. Pat. No. 5,919,757 to Michaelis et al., and U.S. Pat. No. 6,908,610 to Sato et al. Traditionally, surfactants are included in hG-CSF formulations and may protect hG-CSF at potentially destabilizing interfaces, against surfaces encountered during processing, and against the alteration of its conformational stability.

The cDNA cloning and expression of recombinant bovine G-CSF (bG-CSF) has also been described. For example, the polynucleotide and polypeptide sequence of mature bG-CSF is presented in U.S. Pat. No. 5,849,883, which also describes methods to clone, isolate, and purify the polypeptide and analogs thereof. Mature bG-CSF is 174 amino acids in length and has 82% homology to hG-CSF. Heidari et al., supra, describe the expression, purification, and biological activities of bG-CSF.

Administration of bG-CSF to cattle can provide therapeutic benefits. Accordingly, a pharmaceutical formulation containing bG-CSF is desirable to utilize its therapeutic potential. However, bG-CSF pharmaceutical formulations developed according to traditional methods known in the art result in undesirable product properties, such as aggregation and destabilization of the bG-CSF polypeptide and/or the formulation.

Therefore, there exists a need for a stable bG-CSF pharmaceutical formulation with desirable properties, such as minimal product aggregation and destabilization properties. Accordingly, the present invention provides stable aqueous pharmaceutical formulations with a bG-CSF polypeptide or a variant thereof which exhibit desirable properties and provide related advantages as well.

This invention provides stable aqueous formulations comprising a bG-CSF polypeptide or a variant thereof, a buffer substance, and an excipient, wherein said formulation is substantially free of polyoxyethylene (20) sorbitan monolaurate. The invention also provides methods of using, a lyophilized or powdered form of, and processes for preparing the formulation.

The stable aqueous formulations of bovine granulocyte colony stimulating factor ("bG-CSF") according to the invention contain a bG-CSF polypeptide or a variant thereof. As used herein, "bovine G-CSF polypeptide" (alternatively referred to as "bG-CSF polypeptide," "bovine G-CSF," or "bG-CSF") and variants thereof shall include those polypeptides and proteins that have at least one biological activity of a CSF, bG-CSF analogs, bG-CSF mutants, altered glycosylated bG-CSF, PEG conjugated bG-CSF, bG-CSF isoforms, bG-CSF mimetics, bG-CSF fragments, hybrid bG-CSF proteins, fusion proteins, oligomers and multimers, homologues, glycosylation pattern variants, variants, splice variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. Additionally, the term bG-CSF polypeptide or a variant thereof encompasses bG-CSF polypeptides comprising one or more amino acid substitutions, additions or deletions. See U.S. Pat. No. 5,849,883 for examples of analogs of bovine G-CSF. The sequence of mature bG-CSF polypeptide is 174 amino acids in length is as follows (SEQ ID NO: 1):

```
T P L G P A R S L P Q S F L L K C L E Q V R K I Q A D G A E L Q E R L C A A H K
L C H P E E L M L L R H S L G I P Q A P L S S C S S Q S L Q L T S C L N Q L H G G
L F L Y Q G L L Q A L A G I S P E L A P T L D T L Q L D V T D F A T N I W L Q M
```

E D L G A A P A V Q P T Q G A M P T F T S A F Q R R A G G V L V A S Q L H R F

L E L A Y R G L R Y L A E P

Furthermore, bG-CSF polypeptide with an initial methionine amino acid residue is as follows (SEQ ID NO: 2):

M T P L G P A R S L P Q S F L L K C L E Q V R K I Q A D G A E L Q E R L C A A H

K L C H P E E L M L L R H S L G I P Q A P L S S C S S Q S L Q L T S C L N Q L H G

G L F L Y Q G L L Q A L A G I S P E L A P T L D T L Q L D V T D F A T N I W L Q

M E D L G A A P A V Q P T Q G A M P T F T S A F Q R R A G G V L V A S Q L H R

F L E L A Y R G L R Y L A E P

Substitutions in a wide variety of amino acid positions in bG-CSF have been described. Substitutions including but not limited to those that modulate pharmaceutical stability, increase agonist activity, increase protease resistance, convert the polypeptide into an antagonist, etc. are encompassed by the term bG-CSF polypeptide or a variant thereof.

The term bG-CSF polypeptide or a variant thereof also includes glycosylated bG-CSF, such as but not limited to polypeptides glycosylated at any amino acid position, N-linked glycosylated forms of the polypeptide, or O-linked glycosylated forms of the polypeptide. Variants containing single nucleotide changes are also considered as biologically active variants of bG-CSF polypeptide. Variants containing single nucleotide changes are also considered as biologically active variants of bG-CSF. In addition, splice variants are also included. The term bG-CSF polypeptide or a variant thereof also includes bG-CSF heterodimers, homodimers, heteromultimers, or homomultimers of any one or more bG-CSF or any other polypeptide, protein, carbohydrate, polymer, small molecule, linker, ligand, or other active molecule of any type, linked by chemical means or expressed as a fusion protein (see, for example, U.S. Pat. Nos. 6,261,550; 6,166,183; 6,204,247; 6,261,550; and 6,017,876), as well as polypeptide analogues containing, for example, specific deletions or other modifications yet maintain biological activity (see, for example, U.S. Pat. Nos. 6,261,550; 6,004,548; and 6,632,426). bG-CSF polypeptides and variants thereof are described, for example, in U.S. patent application Ser. No. 12/507,237 (now U.S. Patent Application Publication 2010/0035812), herein incorporated by reference. In some embodiments, one or more non-naturally encoded amino acids are incorporated in one or more of the following positions in bG-CSF: 8, 62, 69, 125, 133, 136, and any combination thereof (mature bG-CSF polypeptide or the corresponding amino acids in bG-CSF polypeptide with an initial methionine amino acid residue). In some embodiments, the non-naturally encoded amino acid para-acetylphenylalanine (pAF) is substituted for the naturally encoded amino acid at the one of the following positions: S8, S62, L69, G125, T133, A136, and any combination thereof (mature bG-CSF polypeptide or the corresponding amino acids in bG-CSF polypeptide with an initial methionine amino acid residue).

In one embodiment, the bG-CSF polypeptide or a variant thereof is bG-CSF-S8pAF, which has a sequence of (SEQ ID NO: 1):

T P L G P A R S L P Q S F L L K C L E Q V R K I Q A D G A E L Q E R L C A A H

K L C H P E E L M L L R H S L G I P Q A P L S S C S S Q S L Q L T S C L N Q L H G

G L F L Y Q G L L Q A L A G I S P E L A P T L D T L Q L D V T D F A T N I W L Q

M E D L G A A P A V Q P T Q G A M P T F T S A F Q R R A G G V L V A S Q L H R

F L E L A Y R G L R Y L A E P in which a single para-acetylphenylalanine (pAF) substitution is made at position S8.

In one embodiment, the bG-CSF polypeptide or a variant thereof is bG-CSF-S62pAF, which has a sequence of (SEQ ID NO: 1):

T P L G P A R S L P Q S F L L K C L E Q V R K I Q A D G A E L Q E R L C A A H

K L C H P E E L M L L R H S L G I P Q A P L S S C S S Q S L Q L T S C L N Q L H G

G L F L Y Q G L L Q A L A G I S P E L A P T L D T L Q L D V T D F A T N I W L Q

M E D L G A A P A V Q P T Q G A M P T F T S A F Q R R A G G V L V A S Q L H R

F L E L A Y R G L R Y L A E P in which a single para-acetylphenylalanine (pAF) substitution is made at position S62.

In one embodiment, the bG-CSF polypeptide or a variant thereof is bG-CSF-L69pAF, which has a sequence of (SEQ ID NO: 1):

T P L G P A R S L P Q S F L L K C L E Q V R K I Q A D G A E L Q E R L C A A H

K L C H P E E L M L L R H S L G I P Q A P L S S C S S Q S L Q L T S C L N Q L H G

G L F L Y Q G L L Q A L A G I S P E L A P T L D T L Q L D V T D F A T N I W L Q

M E D L G A A P A V Q P T Q G A M P T F T S A F Q R R A G G V L V A S Q L H R

F L E L A Y R G L R Y L A E P in which a single para-acetylphenylalanine (pAF) substitution is made at position L69.

In one embodiment, the bG-CSF polypeptide or a variant thereof is bG-CSF-G125pAF, which has a sequence of (SEQ ID NO: 1):

T P L G P A R S L P Q S F L L K C L E Q V R K I Q A D G A E L Q E R L C A A H

K L C H P E E L M L L R H S L G I P Q A P L S S C S S Q S L Q L T S C L N Q L H G

G L F L Y Q G L L Q A L A G I S P E L A P T L D T L Q L D V T D F A T N I W L Q

M E D L G A A P A V Q P T Q G A M P T F T S A F Q R R A G G V L V A S Q L H R

F L E L A Y R G L R Y L A E P in which a single para-acetylphenylalanine (pAF) substitution is made at position G125.

In one embodiment, the bG-CSF polypeptide or a variant thereof is bG-CSF-T133pAF, which has a sequence of (SEQ ID NO: 1):

T P L G P A R S L P Q S F L L K C L E Q V R K I Q A D G A E L Q E R L C A A H

K L C H P E E L M L L R H S L G I P Q A P L S S C S S Q S L Q L T S C L N Q L H G

G L F L Y Q G L L Q A L A G I S P E L A P T L D T L Q L D V T D F A T N I W L Q

M E D L G A A P A V Q P T Q G A M P T F T S A F Q R R A G G V L V A S Q L H R

F L E L A Y R G L R Y L A E P in which a single para-acetylphenylalanine (pAF) substitution is made at position T133.

In one embodiment, the bG-CSF polypeptide or a variant thereof is bG-CSF-A136pAF, which has a sequence of (SEQ ID NO: 1):

T P L G P A R S L P Q S F L L K C L E Q V R K I Q A D G A E L Q E R L C A A H

K L C H P E E L M L L R H S L G I P Q A P L S S C S S Q S L Q L T S C L N Q L H G

G L F L Y Q G L L Q A L A G I S P E L A P T L D T L Q L D V T D F A T N I W L Q

M E D L G A A P A V Q P T Q G A M P T F T S A F Q R R A G G V L V A S Q L H R

F L E L A Y R G L R Y L A E P in which a single para-acetylphenylalanine (pAF) substitution is made at position A136.

The formulation of the present invention can include a bG-CSF polypeptide or a variant thereof that is linked to a linker, a polymer, or a biologically active molecule. The linkers, polymers, and biologically active molecule are described in U.S. patent application Ser. No. 12/507,237 (now U.S. Patent Application Publication 2010/0035812). The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including, but not limited to, under physiological conditions for an extended period of time, perhaps even indefinitely. Hydrolytically unstable or degradable linkages mean that the linkages are degradable in water or in aqueous solutions, including, for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

In some embodiments, the bG-CSF polypeptide or a variant thereof is linked to a water soluble polymer. As used herein, the term "water soluble polymer" refers to any polymer that is soluble in aqueous solvents. Linkage of water soluble polymers to a bG-CSF polypeptide or a variant thereof can result in changes including, but not limited to, increased or modulated serum half-life, increased or modulated therapeutic half-life relative to the unmodified form, modulated immunogenicity, modulated physical association characteristics such as aggregation and multimer formation, altered receptor binding, altered binding to one or more binding partners, and altered receptor dimerization or multimerization. The water soluble polymer may or may not have its own biological activity, and may be utilized as a linker for attaching bG-CSF to other substances, including but not limited to one or more bG-CSF polypeptides or variants thereof, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin. WO 03/074087 and WO 03/074088 describe the conjugation of proteins or small molecules to hydroxyalkyl starch (HAS). Examples of hydroxylalkyl starches, include but are not limited to, hydroxyethyl starch. Conjugates of hydroxyalkyl starch and another molecule, for example, may comprise a covalent linkage between terminal aldehyde groups of the HAS and reactive groups of the other molecule.

In some embodiments, the water soluble polymer is a poly(ethylene glycol) moiety. In some embodiments, the poly(ethylene glycol) moiety has a molecular weight of between about 0.1 kDa and about 100 kDa. In another embodiment, the water soluble polymer has a molecular weight of between about 0.1 kDa to about 50 kDa. In some embodiments, the water soluble polymer has a molecular weight of between about 10 kDa to about 30 kDa. In another embodiment, the water soluble polymer has a molecular weight of between about 15 kDa to about 25 kDa. In yet another embodiment, the water soluble polymer has a molecular weight of about 20 kDa. A person skilled in the art would understand that a water soluble polymer with a molecular weight of "about 20 kDa" includes variability in the molecular weight of approximately 15% (i.e., about 17 kDa to about 23 kDa) based on the specification and polydispersion of the moiety.

In one embodiment, the bG-CSF polypeptide or a variant thereof is bG-CSF-S8pAF, which has a sequence of (SEQ ID NO: 1):

T P L G P A R S L P Q S F L L K C L E Q V R K I Q A D G A E L Q E R L C A A H

K L C H P E E L M L L R H S L G I P Q A P L S S C S S Q S L Q L T S C L N Q L H G

G L F L Y Q G L L Q A L A G I S P E L A P T L D T L Q L D V T D F A T N I W L Q

M E D L G A A P A V Q P T Q G A M P T F T S A F Q R R A G G V L V A S Q L H R

F L E L A Y R G L R Y L A E P in which a single para-acetylphenylalanine (pAF) substitution is made at position S8 and is linked to a poly(ethylene glycol) moiety. For example, if the poly(ethylene glycol) moiety had a molecular weight of about 20 kDa, the bG-CSF polypeptide or a variant thereof in this embodiment could be identified as "bG-CSF-S8pAF-20K PEG", indicating that a 20 kDa poly(ethylene glycol) moiety is linked to the pAF substitution made at position S8.

In one embodiment, the bG-CSF polypeptide or a variant thereof is bG-CSF-S62pAF, which has a sequence of (SEQ ID NO: 1):

T P L G P A R S L P Q S F L L K C L E Q V R K I Q A D G A E L Q E R L C A A H

K L C H P E E L M L L R H S L G I P Q A P L S S C S S Q S L Q L T S C L N Q L H G

G L F L Y Q G L L Q A L A G I S P E L A P T L D T L Q L D V T D F A T N I W L Q

M E D L G A A P A V Q P T Q G A M P T F T S A F Q R R A G G V L V A S Q L H R

F L E L A Y R G L R Y L A E P in which a single para-acetylphenylalanine (pAF) substitution is made at position S62 and is linked to a poly(ethylene glycol) moiety. For example, if the poly(ethylene glycol) moiety had a molecular weight of about 20 kDa, the bG-CSF polypeptide or a variant thereof in this embodiment could be identified as "bG-CSF-S62pAF-20K PEG", indicating that a 20 kDa poly(ethylene glycol) moiety is linked to the pAF substitution made at position S62.

In one embodiment, the bG-CSF polypeptide or a variant thereof is bG-CSF-L69pAF, which has a sequence of (SEQ ID NO: 1):

TPLGPARSLPQSFLLKCLEQVRKIQADGAELQERLCAAH

KLCHPEELMLLRHSLGIPQAPLSSCSSQSLQLTSCLNQLHG

GLFLYQGLLQALAGISPELAPTLDTLQLDVTDFATNIWLQ

MEDLGAAPAVQPTQGAMPTFTSAFQRRAGGVLVASQLHR

FLELAYRGLRYLAEP in which a single para-acetylphenylalanine (pAF) substitution is made at position L69 and is linked to a poly(ethylene glycol) moiety. For example, if the poly(ethylene glycol) moiety had a molecular weight of about 20 kDa, the bG-CSF polypeptide or a variant thereof in this embodiment could be identified as "bG-CSF-L69pAF-20K PEG", indicating that a 20 kDa poly(ethylene glycol) moiety is linked to the pAF substitution made at position L69.

In one embodiment, the bG-CSF polypeptide or a variant thereof is bG-CSF-G125pAF, which has a sequence of (SEQ ID NO: 1):

TPLGPARSLPQSFLLKCLEQVRKIQADGAELQERLCAAH

KLCHPEELMLLRHSLGIPQAPLSSCSSQSLQLTSCLNQLHG

GLFLYQGLLQALAGISPELAPTLDTLQLDVTDFATNIWLQ

MEDLGAAPAVQPTQGAMPTFTSAFQRRAGGVLVASQLHR

FLELAYRGLRYLAEP in which a single para-acetylphenylalanine (pAF) substitution is made at position G125 and is linked to a poly (ethylene glycol) moiety. For example, if the poly(ethylene glycol) moiety had a molecular weight of about 20 kDa, the bG-CSF polypeptide or a variant thereof in this embodiment could be identified as "bG-CSF-G125pAF-20K PEG", indicating that a 20 kDa poly(ethylene glycol) moiety is linked to the pAF substitution made at position G125.

In one embodiment, the bG-CSF polypeptide or a variant thereof is bG-CSF-T133pAF, which has a sequence of (SEQ ID NO: 1):

TPLGPARSLPQSFLLKCLEQVRKIQADGAELQERLCAAH

KLCHPEELMLLRHSLGIPQAPLSSCSSQSLQLTSCLNQLHG

GLFLYQGLLQALAGISPELAPTLDTLQLDVTDFATNIWLQ

MEDLGAAPAVQPTQGAMPTFTSAFQRRAGGVLVASQLHR

FLELAYRGLRYLAEP in which a single para-acetylphenylalanine (pAF) substitution is made at position T133 and is linked to a poly(ethylene glycol) moiety. For example, if the poly(ethylene glycol) moiety had a molecular weight of about 20 kDa, the bG-CSF polypeptide or a variant thereof in this embodiment could be identified as "bG-CSF-T133pAF-20K PEG", indicating that a 20 kDa poly(ethylene glycol) moiety is linked to the pAF substitution made at position T133.

In one embodiment, the bG-CSF polypeptide or a variant thereof is bG-CSF-A136pAF, which has a sequence of (SEQ ID NO: 1):

TPLGPARSLPQSFLLKCLEQVRKIQADGAELQERLCAAH

KLCHPEELMLLRHSLGIPQAPLSSCSSQSLQLTSCLNQLHG

GLFLYQGLLQALAGISPELAPTLDTLQLDVTDFATNIWLQ

-continued

```
M E D L G A A P A V Q P T Q G A M P T F T S A F Q R R A G G V L V A S Q L H R

F L E L A Y R G L R Y L A E P
``` in which a single para-acetylphenylalanine (pAF) substitution is made at position A136 and is linked to a poly (ethylene glycol) moiety. For example, if the poly(ethylene glycol) moiety had a molecular weight of about 20 kDa, the bG-CSF polypeptide or a variant thereof in this embodiment could be identified as "bG-CSF-A136pAF-20K PEG", indicating that a 20 kDa poly(ethylene glycol) moiety is linked to the pAF substitution made at position A136.

As used herein, the terms "stability" and "stable" in the context of a formulation comprising a bG-CSF polypeptide or a variant thereof refer to the thermal and chemical unfolding, aggregation, degradation, denaturation, fragmentation, or destabilization of the bG-CSF polypeptide or variant thereof under given manufacture, preparation, transportation and storage conditions. The "stable" formulations of the invention maintain structural integrity, which results in a retention of biological activity, desirably more than 80%, 85%, 90%, 95%, 98%, 99%, or 99.5% under given manufacture, transportation and storage conditions. The stability of the formulations can be assessed by degrees of aggregation, depegylation, degradation, denaturation, or fragmentation by methods known to those skilled in the art and described further herein.

As used herein, the term "aqueous" in the context of a formulation comprising a bG-CSF polypeptide or a variant thereof refers to water, one or more water-soluble organic solvents, or a mixture thereof. The term "organic solvent" is used herein in its conventional sense to refer to a liquid organic compound, typically a monomeric organic material in the form of a liquid, preferably a relatively non-viscous liquid, the molecular structure of which contains hydrogen atoms, carbon atoms, and optionally other atoms as well, and which is capable of dissolving solids gases or liquids.

The pharmaceutical formulations of the invention may comprise a pharmaceutically acceptable carrier. Pharmaceutically acceptable carriers are determined in part by the particular composition being administered, as well as by the particular method used to administer the composition (see, e.g., Remington's Pharmaceutical Sciences, 17th ed. 1985). Suitable pharmaceutically acceptable carriers include but are not limited to buffer substances and excipients, such as those containing saline, buffered saline, dextrose, water, glycerol, ethanol, and/or combinations thereof. Suitable carriers can be buffer substances containing succinate, phosphate, borate, HEPES, citrate, histidine, imidazole, acetate, bicarbonate, and other organic acids. Suitable carriers can be excipients containing polyhydric sugar alcohols, amino acids such as arginine, lysine, glycine, glutamine, asparagine, histidine, alanine, ornithine, leucine, phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Citrate, histidine, maleate, succinate, phosphate, or a combination thereof can be used according to the invention as buffer substances. In some embodiments, citrate or succinate is used as a buffer substance in the stable aqueous formulations. In some embodiments, the buffer substance has a molarity between about 10 mM and about 50 mM. In one embodiment, the buffer substance has a molarity of about 30 mM. The buffer substances can either be present in the form of the corresponding free acid or in the form of the alkali, alkaline-earth or ammonium salts. The formulation can in addition contain further common pharmaceutical auxiliary substances. The sequence of addition of the various auxiliary substances or of the active substance during the production of the liquid pharmaceutical formulations is largely independent of the stabilizing effect in storage found according to the invention and is at the discretion of the person skilled in the art.

Sodium chloride, trehalose, sorbitol, arginine, or a combination thereof can be used as excipients according to the invention. In one embodiment, the excipient is arginine. In some embodiments, arginine has a molarity between about 100 mM to about 500 mM. In other embodiments, arginine has a molarity of about 200 to about 300 mM. In some embodiments, arginine has a molarity of about 250 mM.

Traditionally, pharmaceutical formulations of proteins include surfactants. The inclusion of surfactants may protect proteins at potentially destabilizing interfaces, against surfaces encountered during processing, and against the alteration of their thermodynamic conformational stability. Surfactants are well known in the art, for example polysorbate surfactants. One example of a polysorbate surfactant is polyoxyethylene (20) sorbitan monolaurate, also known by the brand name Tween 20®. However, studies of a bG-CSF formulation containing trace levels of polyoxyethylene (20) sorbitan monolaurate indicate that aggregates increase up to 3.2% (as measured by size exclusion chromatography (SEC)) after 5 days of incubation at 25° C. Thus, the formulations of the present invention are substantially free of a surfactant, a polysorbate surfactant, and/or polyoxyethylene (20) sorbitan monolaurate. As used herein, the term "substantially free" of a surfactant, a polysorbate surfactant, and/or polyoxyethylene (20) sorbitan monolaurate refers to a formulation containing less than 0.033%, less than 0.001%, less than 0.0005%, less than 0.0003%, or less than 0.0001% of the surfactant, polysorbate surfactant, and/or polyoxyethylene (20) sorbitan monolaurate. The formulations of the present invention are substantially free of surfactant, polysorbate surfactant, and/or polyoxyethylene (20) sorbitan monolaurate in order to achieve a stable formulation with desirable properties, such as minimal product aggregation and minimal destabilization, and, where applicable, reduced depegylation.

The term "biologically active molecule" as used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, vaccines, immunogens, hard drugs, soft drugs, carbohydrates, inorganic atoms or molecules, dyes, lipids, nucleosides, radionuclides, oligonucleotides, toxoids, toxins, prokaryotic and eukaryotic cells, viruses, polysaccharides, nucleic acids and portions thereof obtained or derived from viruses, bacteria, insects, animals or any other cell or cell type, liposomes, microparticles and micelles.

The pharmaceutical formulations of the present invention include those that also optionally contain one or more other active ingredients, in addition to a bG-CSF polypeptide or a variant thereof. As used herein, the term "active ingredient" or "therapeutic ingredient" refers to a therapeutically active compound, as well as any prodrugs thereof and pharmaceutically acceptable salts, hydrates and solvates of the compound and the prodrugs. Other active ingredients may be combined with a bG-CSF polypeptide or a variant thereof and may be either administered separately or in the same pharmaceutical formulation. The amount of other active ingredients to be given may be readily determined by one skilled in the art based upon therapy with bG-CSF.

The pharmaceutical formulations of the present invention include those that also optionally contain one or more other inactive ingredients, in addition to a bG-CSF polypeptide or a variant thereof. As used herein, the term "inactive ingredient" refers to a therapeutically inactive compound, as well as any prodrugs thereof and pharmaceutically acceptable salts, hydrates and solvates of the compound and the prodrugs. Other inactive ingredients may be combined with a bG-CSF polypeptide or a variant thereof and may be either administered separately or in the same pharmaceutical formulation. The amount of other inactive ingredients to be given may be readily determined by one skilled in the art based upon therapy with bG-CSF.

The amount of the bG-CSF polypeptide or a variant thereof in the stable aqueous formulations is adequate to achieve a therapeutic effect. As used herein, the term "therapeutically effective amount" refers to an amount which gives the desired benefit to an animal and includes both treatment and prophylactic administration. The amount will vary from one individual to another and will depend upon a number of factors, including the overall physical condition of the patient and the underlying cause of the condition to be treated. The amount of bG-CSF polypeptide or variant thereof used for therapy gives an acceptable rate of change and maintains desired response at a beneficial level. A therapeutically effective amount of the present compositions may be readily ascertained by one of ordinary skill in the art using publicly available materials and procedures. For example, the amount of the bG-CSF polypeptide or variant thereof can be present in the formulation in an amount of between about 0.5 and about 12 grams/liter, preferably about grams/liter.

According to the present invention, the stable aqueous formulations of a bG-CSF polypeptide or variant thereof can be formulated at various pH values. In some embodiments, the stable aqueous formulation can have a pH value of between about 5.7 to about 6.6. In one embodiment, the stable aqueous formulation has a pH of between about 6.0 to about 6.3. The desired pH value of the formulation is adjusted by adding bases such as alkali hydroxides, alkaline-earth hydroxides or ammonium hydroxide.

Sodium hydroxide is preferably used for pH adjustment. The adjustment of the desired pH value can in principle be achieved by adding basic solutions. In general, salts of strong bases with weak acids can be used, such as sodium acetate, sodium citrate, di-sodium or di-potassium hydrogen phosphate or sodium carbonate. If the pharmaceutical solution of auxiliary substance has a basic pH value, it is adjusted by titration with an acid until the desired pH range of 4-5 or 7-8 is reached. Physiologically tolerated inorganic or organic acids come into consideration as acids such as for example hydrochloric acid, phosphoric acid, acetic acid, citric acid, or conventional solutions of substances which have an acidic pH value. In this respect, some example substances are salts of strong acids with weak bases such as e.g., sodium dihydrogen phosphate or potassium dihydrogen phosphate.

As demonstrated in the examples below, bG-CSF formulations of the present invention show desirably low aggregate concentrations of bG-CSF polypeptide or a variant thereof at stressed storage conditions and at accelerated storage conditions. As used herein, stressed storage conditions are evaluated after formulation samples are incubated at 25° C. for 5 days. As used herein, accelerated storage conditions are evaluated after formulation samples are incubated at 40° C. for 1 day. Storage conditions can also be evaluated at other various temperatures and durations for the purposes of the present invention. For example, storage conditions could be evaluated after formulation samples are incubated at 25° C. for 28 days or after formulation samples are incubated at 40° C. for 3 days. Aggregate concentration of bG-CSF polypeptide or a variant thereof are analyzed following stressed storage conditions and accelerated storage conditions. In some embodiments, bG-CSF formulations of the present invention have an aggregate concentration of bG-CSF polypeptide or a variant thereof of less than about 2.1% (weight/weight percentage) at stressed storage conditions. In other embodiments, bG-CSF formulations of the present invention have an aggregate concentration of bG-CSF polypeptide or a variant thereof of less than about 1.5% (weight/weight percentage) at stressed storage conditions. In some embodiments, bG-CSF formulations of the present invention have an aggregate concentration of bG-CSF polypeptide or a variant thereof of less than about 1.5% (weight/weight percentage) at accelerated storage conditions. In other embodiments, bG-CSF formulations of the present invention have an aggregate concentration of bG-CSF polypeptide or a variant thereof of less than about 1.5% (weight/weight percentage) at stressed storage conditions.

In addition, forced agitation studies or freeze-thaw studies can be utilized to assess stability properties of a formulation of the present invention. For example, a forced agitation study could consist of mixing a formulation sample in a glass beaker at a set speed, such as 60 rpm, using a magnetic stirrer. The agitation could occur for a determined period of time, such as two hours, in order to determine the characteristics of the formulation sample. A freeze-thaw cycle could consist of freezing a formulation sample for 1 hour at about −75° C. and thawing at room temperature for approximately 1 hour until no ice was observed.

Moreover, as demonstrated in the examples below, bG-CSF formulations of the present invention can show desirable destabilization and/or depegylation properties of bG-CSF polypeptide or a variant thereof at stressed storage conditions and at accelerated storage conditions. As used herein, the term "depegylation" can refer to the stability of the attachment of pegylated moieties bound to a bG-CSF polypeptide or a variant thereof, i.e. whether such pegylated moieties remain bound to the polypeptide over time, for example during storage in an aqueous solution, or whether they tend to detach, for example as a result of ester bond hydrolysis.

In some embodiments, the stable aqueous formulations of a bG-CSF polypeptide or variant thereof can be formulated using citrate as a buffer substance and arginine as an excipient. In one embodiment, the aqueous formulation can be prepared using citric acid monohydrate (Fisher, C/6200/60 or equivalent) as the buffer substance and L-Arginine (Sigma, A8094 or equivalent) as the excipient. The aqueous formulation can be prepared by adding 1.6±0.1 grams of citric acid monohydrate and 10.9±0.1 grams of L-arginine to 200 mL of high quality water. Thereafter, the pH can be adjusted to 6.0±0.1 using hydrochloric acid and the mixture can be diluted to 250 mL using high quality water. The resultant formulation can comprise 30 mM citrate, 250 mM arginine, and a bG-CSF polypeptide or variant thereof at a pH of 6.0.

The aqueous preparations according to the invention can be used to produce lyophilisates by conventional lyophilization or powders. The preparations according to the invention are obtained again by dissolving the lyophilisates in water or other aqueous solutions. The term "lyophilization," also known as freeze-drying, is a commonly employed technique for presenting proteins which serves to remove water from the protein preparation of interest. Lyophilization is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. For example, see Pikal, M. Biopharm. 3(9)26-30 (1990) and Arakawa et al. Pharm. Res. 8(3):285-291 (1991).

The spray drying of pharmaceutical ingredients is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried including: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. For example, U.S. Pat. Nos. 6,235,710 and 6,001,800 describe the preparation of recombinant erythropoietin by spray drying.

Methods of using a formulation containing a bG-CSF polypeptide or a variant thereof are also encompassed by the present invention. bG-CSF has a variety of biological activities including but not limited to binding to its receptor, causing dimerization of its receptor, stimulation of neutrophil production, and stimulating cell proliferation and differentiation. Examples of some of the biological activities of granulocyte colony stimulating factor and bG-CSF are described above and in U.S. Pat. Nos. 6,676,947; 6,579,525; 6,531,121; 6,521,245; 6,489,293; 6,368,854; 6,316,254; 6,268,336; 6,239,109; 6,165,283; 5,986,047; 5,830,851; 5,043,156; and 5,773,569. The formulations containing b-GCSF polypeptide or a variant thereof of the invention are useful for treating or preventing a wide range of disorders. "Preventing" refers to reducing the likelihood that the recipient will incur or develop any of the pathological conditions described herein and includes prophylactic administration. The term "preventing" is particularly applicable to a patient that is susceptible to the particular patholical condition. "Treating" refers to mediating a disease or condition and preventing, reversing the clinical effects of the disease, or mitigating, its further progression or ameliorate the symptoms associated with the disease or condition.

Administration of G-CSF products results in white blood cell formation. Thus, administration of a formulation containing bG-CSF polypeptide or a variant thereof of the present invention may be useful to prevent infection in animals that are at risk of infection. A formulation containing bG-CSF polypeptide or a variant thereof of the present invention may be administered to animals that have an infection. Infections that may be treated with a formulation containing bG-CSF polypeptide or a variant thereof of the invention include, but are not limited to, mastitis and shipping fever. A formulation containing a bG-CSF polypeptide or a variant thereof of the present invention could be administered to an animal, for example, between two weeks and one day before giving birth and optionally an additional administration could be given on the day of giving birth or up to one week after giving birth. In some embodiments, the animal that is administered the formulation containing a bG-CSF polypeptide or a variant thereof of the present invention is a cow, and giving birth is referred to as "calving." In one embodiment, a formulation containing bG-CSF polypeptide or a variant thereof of the present invention may be administered to periparturient cows for the prevention of mastitis.

According to the invention, a formulation containing bG-CSF polypeptide or a variant thereof may be administered by any conventional route suitable for proteins or peptides, including, but not limited to, parenterally, e.g. injections including, but not limited to, subcutaneously or intravenously or any other form of injections or infusions. Formulations containing bG-CSF polypeptide or a variant thereof can be administered by a number of routes including, but not limited to oral, intravenous, intraperitoneal, intramuscular, transdermal, subcutaneous, topical, sublingual, intravascular, intramammary, or rectal means. Formulations containing bG-CSF polypeptide or a variant thereof can also be administered via liposomes. Such administration routes and appropriate formulations are generally known to those of skill in the art. Formulations containing bG-CSF polypeptide or a variant thereof, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations containing bG-CSF polypeptide or a variant thereof suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations containing bG-CSF polypeptide or a variant thereof can be presented in unit-dose or multi-dose sealed containers, such as ampules and vials. The formulations containing bG-CSF polypeptide or a variant thereof can also be presented in syringes, such as prefilled syringes.

Parenteral administration and intravenous administration are possible methods of administration of the formulations of the present invention. In particular, the routes of administration already in use for natural amino acid homologue therapeutics (including but not limited to, those typically used for EPO, GH, G-CSF, GM-CSF, IFNs, interleukins, antibodies, FGFs, and/or any other pharmaceutically delivered protein), along with formulations in current use, provide possible routes of administration and formulations containing bG-CSF polypeptide or a variant thereof of the invention.

In some embodiments, the formulations of the present invention containing bG-CSF polypeptide or a variant thereof in an amount between about 0.5 and about 12 grams/liter. The dose administered to an animal, in the context of the present invention, is sufficient to have a beneficial therapeutic response in the animal over time, or other appropriate activity, depending on the application. The dose is determined by the efficacy of the particular vector, or formulation, and the activity, stability or serum half-life of the unnatural amino acid polypeptide employed and the condition of the animal, as well as the body weight or surface area of the animal to be treated. The size of the dose is also determined by the existence, nature, and extent of any adverse side-effects that accompany the administration of a particular vector, formulation, or the like in a particular animal.

The dose administered to an animal in the context of the present invention should be sufficient to cause a beneficial response in the subject over time. Generally, the total pharmaceutically effective amount of the bG-CSF polypeptide or a variant thereof of the present invention administered parenterally per dose is in the range of about 0.01 μg/kg/day to about 100 μg/kg, or about 0.05 mg/kg to about 1 mg/kg, of animal body weight, although this is subject to therapeutic discretion. Alternatively, the pharmaceutically effective amount of the bG-CSF polypeptide or a variant thereof of the present invention administered parenterally per dose is about 1 mg to about 25 mg, or about 5 mg to about 20 mg. For example, the pharmaceutically effective amount of the bG-CSF polypeptide or a variant thereof of the present invention administered parenterally per dose can be about 14 mg. The frequency of dosing is also subject to therapeutic discretion.

The pharmaceutically effective amount of the bG-CSF polypeptide or a variant thereof may be administered to animals as a single dose or as part of a multi-dose schedule. For example, the bG-CSF polypeptide or a variant thereof may be administered in a multi-dose schedule wherein the schedule is at least a two dose regimen. In one embodiment, the multi-dose schedule is a two dose regimen.

In one embodiment, the multi-dose schedule comprises a first dose administered to an animal about 1 days to about 14 days before the animal gives birth and the second dose is administered to the animal about 4 days prior to about 7 days after the animal gives birth.

In another embodiment, the multi-dose schedule comprises a first dose administered to an animal about 7 days before the animal gives birth and the second dose is administered to the animal on the day the animal gives birth.

The following embodiments are also contemplated:

1. A stable aqueous formulation comprising a bG-CSF polypeptide or a variant thereof, a buffer substance, and an excipient, wherein said formulation is substantially free of polyoxyethylene (20) sorbitan monolaurate.
2. The formulation of clause 1 wherein the bG-CSF polypeptide or the variant thereof is linked to a linker, a polymer, or a biologically active molecule.
3. The formulation of clause 1 or clause 2 wherein the bG-CSF polypeptide or the variant thereof is linked to a water soluble polymer.
4. The formulation of clause 3 wherein the water soluble polymer comprises a poly(ethylene glycol) moiety.
5. The formulation of clause 3 or clause 4 wherein the water soluble polymer has a molecular weight of between about 0.1 kDa and about 100 kDa.
6. The formulation of any one of clauses 3 to 5 wherein the water soluble polymer has a molecular weight of between about 0.1 kDa and about 50 kDa.
7. The formulation of any one of clauses 3 to 6 wherein the water soluble polymer has a molecular weight of about 20 kDa.
8. The formulation of any one of clauses 1 to 7 wherein the bG-CSF polypeptide or variant thereof is bG-CSF-T133pAF-20K PEG.
9. The formulation of any one of clauses 1 to 8 wherein bG-CSF polypeptide or variant thereof is present in an amount of between about 0.5 and about 12 grams/liter.
10. The formulation of any one of clauses 1 to 9 wherein bG-CSF polypeptide or variant thereof is present in an amount of about 5 grams/liter.
11. The formulation of any one of clauses 1 to 10 wherein the buffer substance is citrate, histidine, maleate, succinate, phosphate, or a combination thereof.
12. The formulation of any one of clauses 1 to 11 wherein the buffer substance is citrate or succinate.
13. The formulation of any one of clauses 1 to 12 wherein the buffer substance is citrate.
14. The formulation of any one of clauses 1 to 12 wherein the buffer substance is succinate.
15. The formulation of any one of clauses 1 to 14 wherein the buffer substance has a molarity between about 10 mM and about 50 mM.
16. The formulation of any one of clauses 1 to 15 wherein the buffer substance has a molarity of about 30 mM.
17. The formulation of any one of clauses 1 to 16 wherein the excipient is sodium chloride, trehalose, sorbitol, arginine, or a combination thereof.
18. The formulation of any one of clauses 1 to 17 wherein the excipient is arginine.
19. The formulation of clause 18 wherein arginine has a molarity of between about 100 mM to about 500 mM.
20. The formulation of clause 18 or clause 19 wherein arginine has a molarity of about 200 to about 300 mM.
21. The formulation of any one of clauses 18 to 20 wherein arginine has a molarity of about 250 mM.
22. The formulation of any one of clauses 1 to 21 wherein the formulation has a pH of between about 5.7 to about 6.6.
23. The formulation of any one of clauses 1 to 22 wherein the formulation has a pH of between about 6.0 to about 6.3.
24. The formulation of any one of clauses 1 to 23 wherein the formulation has an average aggregate concentration of bG-CSF polypeptide or variant thereof of less than about 2.1% wt/wt % after a five day incubation period at stressed storage conditions.
25. The formulation of any one of clauses 1 to 24 wherein the formulation has an average aggregate concentration of bG-CSF polypeptide or variant thereof of less than about 1.5% wt/wt % after a one day incubation period at accelerated storage conditions.

26. The formulation of any one of clauses 1 to 25 optionally including one or more other therapeutic ingredients.

27. A lyophilisate or powder of the formulation of any one of clauses 1 to 26.

28. An aqueous solution produced by dissolving the lyophilisate or powder of clause 27 in water.

29. A process for preparing the formulation of any one of clauses 1 to 26 comprising forming a stable aqueous solution comprising bG-CSF polypeptide or a variant thereof, a buffer substance, and an excipient, wherein said formulation is substantially free of polyoxyethylene (20) sorbitan monolaurate.

30. A method of treating an animal having a disorder modulated by bG-CSF comprising administering to said animal a therapeutically effective amount of the formulation of any one of clauses 1 to 26.

31. The method of clause 30 wherein said disorder is an infection.

32. The method of clause 31 wherein said infection is mastitis and wherein said animal is a periparturient cow.

33. A stable aqueous formulation comprising a bG-CSF polypeptide or a variant thereof, a citrate or succinate buffer, arginine, and optionally a counter ion for arginine.

34. The formulation of clause 33 wherein the formulation is substantially free of a polysorbate surfactant.

35. The formulation of clause 33 or clause 34 wherein the bG-CSF polypeptide or the variant thereof is linked to a linker, a polymer, or a biologically active molecule.

36. The formulation of any one of clauses 33 to 35 wherein the bG-CSF polypeptide or the variant thereof is linked to a water soluble polymer.

37. The formulation of clause 36 wherein the water soluble polymer comprises a poly(ethylene glycol) moiety.

38. The formulation of clause 36 or clause 37 wherein the water soluble polymer has a molecular weight of between about 0.1 kDa and about 100 kDa.

39. The formulation of any one of clauses 36 to 38 wherein the water soluble polymer has a molecular weight of between about 0.1 kDa and about 50 kDa.

40. The formulation of any one of clauses 36 to 39 wherein the water soluble polymer has a molecular weight of about 20 kDa.

41. The formulation of any one of clauses 34 to 40 wherein said polysorbate surfactant is a polyoxyethylene derivative of sodium monolaurate.

42. The formulation of any one of clauses 34 to 41 wherein said polysorbate surfactant is polyoxyethylene (20) sorbitan monolaurate.

43. The formulation of any one of clauses 33 to 42 wherein the bG-CSF polypeptide or variant thereof is bG-CSF-T133pAF-20K PEG.

44. The formulation of clause 43 wherein bG-CSF-T133pAF-20K PEG is present in an amount of between about 0.5 and about 12 grams/liter, the citrate buffer has a molarity of about 30 mM, arginine has a molarity of about 250 mM, and wherein the formulation has a pH value of about 6.0.

45. The formulation of clause 43 or clause 44 wherein the formulation has an average aggregate concentration of bG-CSF-T133pAF-20K PEG of less than about 1.6% wt/wt % after a 28-day incubation period at 25° C.

46. The formulation of any one of clauses 43 to 45 wherein the formulation has an average aggregate concentration of bG-CSF-T133pAF-20K PEG of less than about 2.8% wt/wt % after a 3-day incubation period at 40° C.

47. The formulation of any one of clauses 43 to 46 wherein the formulation has an average aggregate concentration of bG-CSF-T133pAF-20K PEG of about 1.6% wt/wt % or less after a forced agitation study.

48. The formulation of any one of clauses 43 to 47 wherein the formulation has an average aggregate concentration of bG-CSF-T133pAF-20K PEG of less than about 1.6% wt/wt % after five freeze-thaw cycles.

49. The formulation of any one of clauses 33 to 48 wherein the counter ion for arginine is chloride or sulfate.

50. The formulation of any one of clauses 33 to 49 optionally including one or more other therapeutic ingredients.

51. A lyophilisate or powder of the formulation of any one of clauses 33 to 50.

52. An aqueous solution produced by dissolving the lyophilisate or powder of clause 51 in water.

53. A process for preparing the formulation of any one of clauses 33 to 50 comprising forming a stable aqueous solution comprising a bG-CSF polypeptide or variant thereof, a citrate buffer, arginine, and optionally a counter ion for arginine.

54. The process of clause 53 wherein the formulation is substantially free of a polysorbate surfactant.

55. The process of clause 53 or clause 54 wherein the bG-CSF polypeptide or variant thereof is bG-CSF-T133pAF-20K PEG.

56. A method of treating an animal having a disorder modulated by bG-CSF comprising administering to said animal a therapeutically effective amount of the formulation of any one of clauses 33 to 50.

57. The method of clause 56 wherein said disorder is an infection.

58. The method of clause 57 wherein said infection is mastitis and wherein said animal is a periparturient cow.

59. A stable aqueous formulation consisting essentially of a bG-CSF polypeptide or a variant thereof, a citrate or succinate buffer, arginine, and optionally a counter ion for arginine.

60. The formulation of clause 59 wherein the formulation is substantially free of a surfactant.

61. The formulation of clause 59 or clause 60 wherein the bG-CSF polypeptide or the variant thereof is linked to a linker, a polymer, or a biologically active molecule.

62. The formulation of any one of clauses 59 to 61 wherein the bG-CSF polypeptide or the variant thereof is linked to a water soluble polymer.

63. The formulation of clause 62 wherein the water soluble polymer comprises a poly(ethylene glycol) moiety.

64. The formulation of clause 62 or clause 63 wherein the water soluble polymer has a molecular weight of between about 0.1 kDa and about 100 kDa.

65. The formulation of any one of clauses 62 to 64 wherein the water soluble polymer has a molecular weight of between about 0.1 kDa and about 50 kDa.

66. The formulation of any one of clauses 62 to 65 wherein the water soluble polymer has a molecular weight of about 20 kDa.

67. The formulation of any one of clauses 60 to 66 wherein said surfactant is a polysorbate surfactant.

68. The formulation of any one of clauses 60 to 67 wherein said surfactant is a polyoxyethylene derivative of sodium monolaurate.
69. The formulation of any one of clauses 60 to 68 wherein said surfactant is polyoxyethylene (20) sorbitan monolaurate.
70. The formulation of any one of clauses 59 to 69 wherein the bG-CSF polypeptide or variant thereof is bG-CSF-T133pAF-20K PEG.
71. The formulation of clause 70 wherein bG-CSF-T133pAF-20K PEG is present in an amount of between about 0.5 and about 12 grams/liter, the citrate buffer has a molarity of about 30 mM, arginine has a molarity of about 250 mM, and wherein the formulation has a pH value of about 6.0.
72. The formulation of clause 70 or clause 71 wherein the formulation has an average aggregate concentration of bG-CSF-T133pAF-20K PEG of less than about 1.6% wt/wt % after a 28-day incubation period at 25° C.
73. The formulation of any one of clauses 70 to 72 wherein the formulation has an average aggregate concentration of bG-CSF-T133pAF-20K PEG of less than about 2.8% wt/wt % after a 3-day incubation period at 40° C.
74. The formulation of any one of clauses 70 to 73 wherein the formulation has an average aggregate concentration of bG-CSF-T133pAF-20K PEG of about 1.6% wt/wt % or less after a forced agitation study.
75. The formulation of any one of clauses 70 to 74 wherein the formulation has an average aggregate concentration of bG-CSF-T133pAF-20K PEG of less than about 1.6% wt/wt % after five freeze-thaw cycles.
76. The formulation of any one of clauses 59 to 75 wherein the counter ion for arginine is chloride or sulfate.
77. The formulation of any one of clauses 59 to 76 optionally including one or more other therapeutic ingredients.
78. A lyophilisate or powder of the formulation of any one of clauses 59 to 77.
79. An aqueous solution produced by dissolving the lyophilisate or powder of clause 78 in water.
80. A process for preparing the formulation of any one of clauses 59 to 77 comprising forming a stable aqueous solution consisting essentially of a bG-CSF polypeptide or variant thereof, a citrate buffer, arginine, and optionally a counter ion for arginine.
81. The process of clause 80 wherein the formulation is substantially free of a surfactant.
82. The process of clause 80 or clause 81 wherein the bG-CSF polypeptide or variant thereof is bG-CSF-T133pAF-20K PEG.
83. A method of treating an animal having a disorder modulated by bG-CSF comprising administering to said animal a therapeutically effective amount of the formulation of any one of clauses 59 to 77.
84. The method of clause 83 wherein said disorder is an infection.
85. The method of clause 84 wherein said infection is mastitis and wherein said animal is a periparturient cow.
86. A stable aqueous formulation consisting essentially of bG-CSF-T133pAF-20K PEG, a citrate buffer wherein the citrate buffer has a molarity of about 30 mM, arginine wherein arginine has a molarity of about 250 mM, and optionally a counter ion for arginine.

EXAMPLE 1

Buffer and Excipient Screening Study bGCSF-T133-20K PEG formulations without polyoxyethylene (20) sorbitan monolaurate in the background can be screened to assess product stability using multiple buffers and excipients (sodium chloride, trehalose, and arginine). The target pH for all dialysis buffers is pH 6.0. For comparison, a formulation containing 10 mM phosphate, 180 mM mannitol, and 60 mM trehalose at pH 6.0 can be prepared. The formulations can be evaluated for effects on protein aggregation and depegylation in the presence and absence of oxygen.

The samples can be prepared by dialyzing 1 mL of bGCSF-T133-20K PEG at 2-8° C. into each formulation. Protein concentration of the dialyzed samples can be determined before normalizing the protein concentration to 5 mg/mL. After dialysis and concentration normalization, approximately 3×1 mL of the post-dialyzed and diluted pool can be filled into 5 mL glass vials. One set of samples can be tested to provide initial conditions. A second set can be stored at 25° C./60% RH for 5 days before testing. The third set of samples can be degassed in the lyophilization chamber, closed under an inert atmosphere (nitrogen), and then stored at 25° C./60% RH for 5 days before testing. If the level of aggregate as measured by SEC after 5 days is ≤2.0%, both the degassed and non-degassed samples can be incubated at 40° C. for one day.

After five days of incubation, protein concentration of each sample can be measured. Table 1 shows protein concentrations.

TABLE 1

Protein Concentrations from the Buffer and Excipient Screening Study

| Sample No. | Sample Description | Post 5-Day at 2-8° C. Concentration (mg/mL) | Post 5-Day at 25° C. Concentration (mg/mL) UN-DEGAS | Post 5-Day at 26° C. Concentration (mg/mL) DEGAS |
|---|---|---|---|---|
| 1 | 10 mM Citrate, 0.1M Arginine | 5.75 | 5.29 | 5.93 |
| 2 | 10 mM Citrate, 0.15M NaCl | 6.35 | 6.71 | 5.45 |
| 3 | 10 mM Citrate, 0.3M Trehalose | 5.71 | 5.78 | 5.79 |
| 4 | 10 mM Histidine, 0.15M NaCl | 5.39 | 5.19 | 5.42 |
| 5 | 10 mM Histidine, 0.3M Trehalose | 5.30 | 5.08 | 5.34 |
| 6 | 10 mM Histidine, 0.1M Arginine | 5.56 | 5.06 | 5.27 |
| 7 | 10 mM Maleate, 0.15M NaCl | 5.50 | 5.40 | 5.73 |
| 8 | 10 mM Maleate, 0.3M Trehalose | 4.41 | 4.01 | 4.13 |
| 9 | 10 mM Maleate, 0.1M Arginine | 5.69 | 5.41 | 5.39 |
| 10 | 10 mM Succinate, 0.15M NaCl | 5.94 | 5.88 | 5.83 |

TABLE 1-continued

Protein Concentrations from the Buffer and Excipient Screening Study

| Sample No. | Sample Description | Post 5-Day at 2-8° C. Concentration (mg/mL) | Post 5-Day at 25° C. Concentration (mg/mL) UN-DEGAS | Post 5-Day at 26° C. Concentration (mg/mL) DEGAS |
|---|---|---|---|---|
| 11 | 10 mM Succinate, 0.3M Trehalose | 5.57 | 5.79 | 5.66 |
| 12 | 10 mM Succinate, 0.1M Arginine | 4.96 | 4.92 | 4.78 |
| 13 | 10 mM Phosphate, 0.15M NaCl | 5.20 | 5.18 | 5.03 |
| 14 | 10 mM Phosphate, 0.3M Trehalose | 5.13 | 5.30 | 5.24 |
| 15 | 10 mM Phosphate, 0.1M Arginine | 5.22 | 5.04 | 5.12 |
| 16 | 10 mM Phosphate, 180 mM Mannitol, 60 mM Trehalose | 5.28 | 5.22 | 5.21 |

Table 2 shows the pH results for each sample.

TABLE 2 pH Results from the Buffer and Excipient Screening Study

| Buffer Condition | Dialysis Buffer pH | Post Dialysis pH | 5-Day 2-8 C. pH | 5-Day 25 C. pH | 5-Day 25 C. Degassed pH |
|---|---|---|---|---|---|
| 10 mM Citrate, 0.1M Arginine | 6.49 | 6.44 | 6.48 | 6.57 | 6.53 |
| 10 mM Citrate, 0.15M NaCl | 6.51 | 6.47 | 6.52 | 6.55 | 6.61 |
| 10 mM Citrate, 0.3M Trehalose | 6.11 | 6.07 | 6.10 | 6.16 | 6.18 |
| 10 mM Histidine, 0.15M NaCl | 5.86 | 5.85 | 5.91 | 5.91 | 5.95 |
| 10 mM Histidine, 0.3M Trehalose | 5.78 | 5.81 | 5.92 | 5.96 | 5.95 |
| 10 mM Histidine, 0.1M Arginine | 6.22 | 6.23 | 6.30 | 6.32 | 6.29 |
| 10 mM Maleate, 0.15M NaCl | 6.22 | 6.22 | 6.28 | 6.32 | 6.29 |
| 10 mM Maleate, 0.3M Trehalose | 6.06 | 6.03 | 6.11 | 6.13 | 6.12 |
| 10 mM Maleate, 0.1M Arginine | 6.24 | 6.23 | 6.34 | 6.34 | 6.32 |
| 10 mM Succinate, 0.15M NaCl | 6.14 | 6.13 | 6.19 | 6.26 | 6.31 |
| 10 mM Succinate, 0.3M Trehalose | 6.09 | 6.07 | 6.13 | 6.13 | 6.16 |
| 10 mM Succinate, 0.1M Arginine | 6.14 | 6.14 | 6.30 | 6.34 | 6.34 |
| 10 mM Phosphate, 0.15M NaCl | 6.29 | 6.26 | 6.30 | 6.33 | 6.37 |
| 10 mM Phosphate, 0.3M Trehalose | 5.97 | 5.98 | 6.03 | 6.10 | 6.13 |
| 10 mM Phosphate, 0.1M Arginine | 6.40 | 6.38 | 6.41 | 6.47 | 6.47 |
| 10 mM Phosphate, 180 mM Mannitol, 60 mM Trehalose | 6.09 | 6.04 | 6.14 | 6.11 | 6.12 |

Protein aggregation and depegylation levels in each formulation can be analyzed by SEC. Table 3 shows the SEC results and indicates that the aggregation and depegylation levels were similar across all samples.

TABLE 3

SEC Results from the Buffer and Excipient Screening Study (Post 5 Days Incubation)

| Sample | Control Samples (2-8° C.) | | | 5-Day Incubation at 25° C. | | | 5-Day Incubation at 25° C. (DEGAS) | | |
|---|---|---|---|---|---|---|---|---|---|
| | Avg % Aggregate | Avg % PEG-bGCSF | Avg % bGCSF | Avg % Aggregate | Avg % PEG-bGCSF | Avg % bGCSF | Avg % Aggregate | Avg % PEG-bGCSF | Avg % bGCSF |
| Pre-dialyzed bGCSF-T133-20K PEG NBJ0801-04-04 | 0.7 | 98.5 | 0.7 | | | | N/A | | |
| 10 mM Citrate, 0.15M NaCl | 1.2 | 98.3 | 0.5 | 1.6 | 98.0 | 0.5 | 1.6 | 98.0 | 0.4 |
| 10 mM Citrate, 0.3M Trehalose | 1.3 | 98.3 | 0.4 | 1.5 | 98.1 | 0.4 | 1.7 | 97.8 | 0.4 |
| 10 mM Citrate, 0.1M Arginine | 1.3 | 98.2 | 0.4 | 1.4 | 98.1 | 0.5 | 1.5 | 98.0 | 0.5 |
| 10 mM Histidine, 0.15M NaCl | 1.3 | 98.1 | 0.6 | 1.5 | 97.8 | 0.7 | 1.6 | 97.8 | 0.7 |
| 10 mM Histidine, 0.3M Trehalose | 1.3 | 98.2 | 0.5 | 1.7 | 97.8 | 0.5 | 1.9 | 97.6 | 0.5 |
| 10 mM Histidine, 0.1M Arginine | 1.3 | 98.1 | 0.6 | 1.3 | 98.1 | 0.7 | 1.5 | 97.8 | 0.6 |
| 10 mM Maleate, 0.15M NaCl | 1.4 | 98.1 | 0.5 | 1.6 | 97.8 | 0.6 | 1.7 | 97.7 | 0.6 |
| 10 mM Maleate, 0.3M Trehalose | 1.3 | 98.2 | 0.4 | 1.7 | 97.9 | 0.4 | 1.7 | 97.9 | 0.4 |
| 10 mM Maleate, 0.1M Arginine | 1.3 | 98.2 | 0.6 | 1.3 | 98.1 | 0.6 | 1.4 | 97.9 | 0.6 |
| 10 mM Succinate, 0.15M NaCl | 1.4 | 98.1 | 0.5 | 1.6 | 97.8 | 0.6 | 1.9 | 97.5 | 0.5 |
| 10 mM Succinate, 0.3M Trehalose | 1.3 | 98.3 | 0.4 | 1.7 | 97.9 | 0.4 | 1.9 | 97.7 | 0.4 |
| 10 mM Succinate, 0.1M Arginine | 1.5 | 98.0 | 0.6 | 1.5 | 97.9 | 0.6 | 2.0 | 97.4 | 0.6 |

TABLE 3-continued

SEC Results from the Buffer and Excipient Screening Study (Post 5 Days Incubation)

| Sample | Control Samples (2-8° C.) | | | 5-Day Incubation at 25° C. | | | 5-Day Incubation at 25° C. (DEGAS) | | |
| --- | --- | --- | --- | --- | --- | --- | --- | --- | --- |
| | Avg % Aggregate | Avg % PEG-bGCSF | Avg % bGCSF | Avg % Aggregate | Avg % PEG-bGCSF | Avg % bGCSF | Avg % Aggregate | Avg % PEG-bGCSF | Avg % bGCSF |
| 10 mM Phosphate, 0.15M NaCl | 1.1 | 98.2 | 0.7 | 1.3 | 98.0 | 0.7 | 1.4 | 97.9 | 0.7 |
| 10 mM Phosphate, 0.3M Trehalose | 1.1 | 98.4 | 0.5 | 1.7 | 97.8 | 0.6 | 1.8 | 97.6 | 0.6 |
| 10 mM Phosphate, 0.1M Arginine | 1.1 | 98.2 | 0.6 | 1.3 | 98.1 | 0.7 | 1.5 | 97.8 | 0.7 |
| 10 mM, Phosphate, 0.18M Mannitol, 0.06M Trehalose | 1.2 | 98.3 | 0.5 | 2.0 | 97.5 | 0.5 | 2.1 | 97.4 | 0.5 |

Table 4 shows the SEC results for samples incubated at 40° C. for one day. Comparison of the aggregate composition indicates that formulations containing arginine had the lowest product aggregation. Furthermore, the reference formulation 10 mM phosphate, 180 mM Mannitol, and 60 mM Trebalose pH 6 has the highest level of aggregation if compared to all the other formulations in the screening study.

TABLE 4

SEC Results from the Buffer and Excipient Screening Study (Post 1 Day Incubation)

| | 1-Day Incubation 40° C. | | | 1-Day Incubation 40° C. (DEGAS) | | |
| --- | --- | --- | --- | --- | --- | --- |
| | Avg % Aggregate | Avg % PEG-bGCSF | Avg % bGCSF | Avg % Aggregate | Avg % PEG-bGCSF | Avg % bGCSF |
| 10 mM Citrate, 0.15M NaCl | 6.5 | 93.3 | 0.1 | 7.2 | 92.7 | 0.1 |
| 10 mM Citrate, 0.3M Trehalose | 4.1 | 95.8 | 0.1 | 4.3 | 95.6 | 0.1 |
| 10 mM Citrate, 0.1M Arginine | 3.9 | 95.9 | 0.2 | 3.3 | 96.5 | 0.2 |
| 10 mM Histidine, 0.15M NaCl | 6.0 | 93.8 | 0.2 | 5.9 | 93.9 | 0.2 |
| 10 mM Histidine, 0.3M Trehalose | 8.4 | 91.5 | 0.1 | 9.3 | 90.6 | 0.1 |
| 10 mM Histidine, 0.1M Arginine | 3.0 | 96.7 | 0.3 | 2.9 | 96.8 | 0.3 |
| 10 mM Maleate, 0.15M NaCl | 5.9 | 93.9 | 0.2 | 6.0 | 93.9 | 0.1 |
| 10 mM Maleate, 0.3M Trehalose | 7.3 | 92.7 | 0.1 | 7.4 | 92.5 | 0.1 |
| 10 mM Maleate, 0.1M Arginine | 3.0 | 96.8 | 0.2 | 3.1 | 96.7 | 0.2 |
| 10 mM Succinate, 0.15M NaCl | 4.3 | 95.5 | 0.2 | 5.3 | 94.6 | 0.1 |
| 10 mM Succinate, 0.3M Trehalose | 9.6 | 90.3 | 0.1 | 10.8 | 89.1 | 0.2 |
| 10 mM Succinate, 0.1M Arginine | 2.1 | 97.6 | 0.3 | 2.6 | 97.2 | 0.2 |
| 10 mM Phosphate, 0.15M NaCl | 5.9 | 94.0 | 0.2 | 5.9 | 93.9 | 0.1 |
| 10 mM Phosphate, 0.3M Trehalose | 16.0 | 84.0 | 0.0 | 18.2 | 81.8 | 0.0 |
| 10 mM Phosphate, 0.1M Arginine | 4.5 | 95.2 | 0.2 | 3.8 | 96.0 | 0.2 |
| 10 mM, Phosphate, 0.18M Mannitol, 0.06M Trehalose | 22.8 | 77.2 | 0.0 | 25.0 | 75.0 | 0.0 |

Results from this screening study indicate that succinate, histidine, maleate, and citrate formulations without polyoxyethylene (20) sorbitan monolaurate all have negligible aggregate increase (less than 1% by SEC) after a five day incubation at 25° C. Also, no difference exists in protein stability between the degassed and non-degassed samples. Furthermore, SEC results from stressed samples at 40° C. for one day show that formulations containing 0.1 M arginine have less aggregation compared with formulations containing sodium chloride and trehalose excipients.

EXAMPLE 2

Effect of Polyoxyethylene (20) Sorbitan Monolaurate on bG-CSF Formulations

The effect of polyoxyethylene (20) sorbitan monolaurate on aggregation can be evaluated to determine the impact on future formulations for agitation studies. The samples can be prepared by dialyzing 4 mL of bGCSF-T133-20K PEG at 2-8° C. into 10 mM Phosphate and 150 mM NaCl at pH 6.0. Following dialysis, the dialyzed pool can be spiked with a 1% polyoxyethylene (20) sorbitan monolaurate stock solution and then can be diluted with 10 mM Phosphate and 150 mM NaCl at pH 6.0 to a final protein concentration of 5 mg/mL. Samples from each formulation can be divided into 2×1 mL aliquots filled in 1 mL glass vials to form two sets of samples. One set can be stored at 2-8° C. and tested at initial conditions; a second set can be can be stored at 40° C. for one day.

Table 5 shows the SEC integration data and indicates that the aggregation level increases with increasing polyoxyethylene (20) sorbitan monolaurate concentration. SEC analysis of the samples indicates that bGCSF-T133-20K PEG aggregation increases with polyoxyethylene (20) sorbitan monolaurate concentration. As a result, polyoxyethylene (20) sorbitan monolaurate can be excluded from future formulation testing for bGCSF-T133-20K PEG.

TABLE 5

SEC Results from the Polyoxyethylene (20) Sorbitan Monolaurate Study
(Post 1 Day Incubation)

| | Initial | | | 1-Day Incubation 40° C. | | |
|---|---|---|---|---|---|---|
| Buffer | Avg % Aggregate | Avg % PEG-bGCSF | Avg % bGCSF | Avg % Aggregate | Avg % PEG-bGCSF | Avg % bGCSF |
| Pre-Dialyze Pool NBJ0801-04-04 | 0.7 | 99.0 | 0.3 | | N/A | |
| 10 mM Phosphate, 150 mM NaCl | 0.8 | 98.2 | 1.0 | 2.6 | 96.6 | 0.8 |
| 10 mM Phosphate, 150 mM NaCl, 0.0033% Tween-20 | 0.8 | 98.1 | 1.1 | 3.7 | 95.6 | 0.7 |
| 10 mM Phosphate, 150 mN NaCl, 0.05% Tween-20 | 0.9 | 98.0 | 1.1 | 9.2 | 90.1 | 0.7 |

EXAMPLE 3

Box-Behnken Response Surface Design (DOE #1)

The effect of various arginine concentrations along with other key historical formulation parameters can be tested to evaluate the main effects as well as their interactions. The experimental design can be a Box-Behnken response surface where each numeric factor is varied at the low, center, and high level. Furthermore, the buffer type can be a categorical factor. The parameter combination can be duplicated for citrate and succinate, each with three centerpoints. The pH can be set at 6.0 for all conditions. A control condition comprising 10 mM Phosphate, 150 mM NaCl, and 0.0033% polyoxyethylene (20) sorbitan monolaurate at pH 6 can be included for comparison with historical results.

All dialysis buffers can be prepared at pH 6.0 t 0.1. PEG-bGCSF can be dialyzed into 18 buffer conditions that represent all the buffer conditions of the DOE #1 study. The protein recovery across the dialysis step can be generally ≥78% and, thus, is consistent within the dialysis sample set. Following dialysis, the protein concentration of dialyzed pool can be adjusted with the dialysis buffer to the target value shown in the Box-Behnken response surface design. This could result in 24 formulation combinations plus three centerpoints in citrate and three centerpoints in succinate. Each formulation can be divided into 3×1 mL aliquots filled in 1 mL glass vials to form three sets of samples: one set can be tested as initial conditions and then stored at 2-8° C., a second can be stored at 25° C. for two weeks, and the third set can be stored at 40° C. for one day.

Changes in product concentration can be analyzed to assess product stability. Table 6 shows the product concentration of samples before and after incubation. Samples at 10 mM Citrate, 300 mM Arginine (8 mg/mL) and 10 mM Succinate, 300 mM Arginine (8 mg/mL) have the highest increase (0.5-0.6 mg/mL) whereas the difference is less for all other samples.

TABLE 6

Summary of Protein Concentration from the DOE #1
Study (Initial and 1-day at 40° C.)

| | Protein Concentration (mg/mL) | | |
|---|---|---|---|
| Sample | Initial | 40° C. for 1 Day | Difference |
| 10 mM Citrate, 100 mM Arginine (5 mg/mL) | 4.89 | 5.16 | 0.27 |
| 10 mM Citrate, 300 mM Arginine (2 mg/mL) | 1.99 | 2.05 | 0.06 |
| 10 mM Citrate, 300 mM Arginine (8 mg/mL) | 7.60 | 8.19 | 0.59 |
| 10 mM Citrate, 500 mM Arginine (5 mg/mL) | 4.97 | 4.89 | −0.08 |
| 30 mM Citrate, 100 mM Arginine (2 mg/mL) | 1.99 | 2.01 | 0.02 |
| 30 mM Citrate, 100 mM Arginine (8 mg/mL) | 8.23 | 8.14 | −0.09 |
| 30 mM Citrate, 300 mM Arginine (5 mg/mL) Vial A | 5.03 | 4.86 | −0.17 |
| 30 mM Citrate, 300 mM Arginine (5 mg/mL) Vial B | 5.07 | 4.93 | −0.14 |
| 30 mM Citrate, 300 mM Arginine (5 mg/mL) Vial C | 5.08 | 5.01 | −0.07 |
| 30 mM Citrate, 500 mM Arginine (2 mg/mL) | 2.00 | 2.01 | 0.01 |
| 30 mM Citrate, 500 mM Arginine (8 mg/mL) | 8.05 | 7.95 | −0.10 |
| 50 mM Citrate, 100 mM Arginine (5 mg/mL) | 5.07 | 5.01 | −0.06 |
| 50 mM Citrate, 300 mM Arginine (2 mg/mL) | 1.99 | 2.00 | 0.01 |
| 50 mM Citrate, 300 mM Arginine (8 mg/mL) | 8.17 | 8.17 | 0.00 |
| 50 mM Citrate, 500 mM Arginine (5 mg/mL) | 4.89 | 4.93 | 0.04 |
| 10 mM Succinate, 100 mM Arginine (5 mg/mL) | 5.25 | 5.06 | −0.19 |
| 10 mM Succinate, 300 mM Arginine (2 mg/mL) | 1.94 | 1.88 | −0.06 |
| 10 mM Succinate, 300 mM Arginine (8 mg/mL) | 8.21 | 8.72 | 0.51 |
| 10 mM Succinate, 500 mM Arginine (5 mg/mL) | 5.03 | 4.91 | −0.12 |
| 30 mM Succinate, 100 mM Arginine (2 mg/mL) | 2.04 | 1.75 | −0.29 |
| 30 mM Succinate, 100 mM Arginine (5 mg/mL) | 7.97 | 7.79 | −0.18 |
| 30 mM Succinate, 300 mM Arginine (5 mg/mL) Vial A | 4.92 | 4.77 | −0.15 |

TABLE 6-continued

Summary of Protein Concentration from the DOE #1
Study (Initial and 1-day at 40° C.)

| | Protein Concentration (mg/mL) | | |
|---|---|---|---|
| Sample | Initial | 40° C. for 1 Day | Difference |
| 30 mM Succinate, 300 mM Arginine (5 mg/mL) Vial B | 4.87 | 4.85 | −0.02 |
| 30 mM Succinate, 300 mM Arginine (5 mg/mL) Vial C | 4.97 | 4.80 | −0.17 |
| 30 mM Succinate, 500 mM Arginine (2 mg/mL) | 1.90 | 1.86 | −0.04 |
| 30 mM Succinate, 500 mM Arginine (8 mg/mL) | 7.81 | 7.69 | −0.12 |
| 50 mM Succinate, 100 mM Arginine (5 mg/mL) | 4.80 | 4.94 | 0.14 |
| 50 mM Succinate, 300 mM Arginine (2 mg/mL) | 1.86 | 1.84 | −0.02 |
| 50 mM Succinate, 300 mM Arginine (8 mg/mL) | 7.88 | 7.76 | −0.12 |
| 50 mM Succinate, 600 mM Arginine (5 mg/mL) | 4.91 | 4.92 | 0.00 |
| 10 mM Phosphate, 150 mM NaCl, 0.0033% Tween-20 (w/v) (6 mg/mL)4 | 5.05 | 5.02 | −0.02 |

Changes in pH can be analyzed to assess pH stability of the samples. All sample pH can be within the range of 6.0-6.3. Table 7 shows the pH values and the difference from the time zero. Sample pH is stable for the entire duration of the DOE #1 study.

TABLE 7

Summary of pH from the DOE #1
Study (Initial and 1-day at 40° C.)

| | pH | | |
|---|---|---|---|
| Sample | Initial | 40° C. for 1 Day | Difference |
| 10 mM Citrate, 100 mM Arginine (5 mg/mL) | 6.14 | 6.16 | 0.02 |
| 10 mM Citrate, 300 mM Arginine (2 mg/mL) | 6.10 | 6.12 | 0.02 |
| 10 mM Citrate, 300 mM Arginine (8 mg/mL) | 6.08 | 6.10 | 0.02 |
| 10 mM Citrate, 500 mM Arginine (5 mg/mL) | 6.25 | 6.27 | 0.02 |
| 30 mM Citrate, 100 mM Arginine (2 mg/mL) | 6.15 | 6.19 | 0.04 |
| 30 mM Citrate, 100 mM Arginine (8 mg/mL) | 6.13 | 6.19 | 0.06 |
| 30 mM Citrate, 300 mM Arginine (5 mg/mL) Vial A | 6.19 | 6.21 | 0.02 |
| 30 mM Citrate, 300 mM Arginine (5 mg/mL) Vial B | 6.31 | 6.21 | −0.10 |
| 30 mM Citrate, 300 mM Arginine (5 mg/mL) Vial C | 6.24 | 6.21 | −0.03 |
| 30 mM Citrate, 500 mM Arginine (2 mg/mL) | 6.16 | 6.16 | 0.00 |
| 30 mM Citrate, 500 mM Arginine (8 mg/mL) | 6.12 | 6.15 | 0.03 |
| 50 mM Citrate, 100 mM Arginine (5 mg/mL) | 6.28 | 6.22 | −0.06 |
| 50 mM Citrate, 300 mM Arginine (2 mg/mL) | 6.19 | 6.18 | −0.01 |
| 50 mM Citrate, 300 mM Arginine (8 mg/mL) | 6.19 | 6.16 | −0.03 |
| 50 mM Citrate, 500 mM Arginine (5 mg/mL) | 6.19 | 6.15 | −0.04 |
| 10 mM Succinate, 100 mM Arginine (5 mg/mL) | 6.11 | 6.16 | 0.05 |
| 10 mM Succinate, 300 mM Arginine (2 mg/mL) | 6.05 | 6.08 | 0.03 |
| 10 mM Succinate, 300 mM Arginine (8 mg/mL) | 6.04 | 6.05 | 0.01 |
| 10 mM Succinate, 500 mM Arginine (5 mg/mL) | 6.17 | 6.17 | 0.00 |
| 30 mM Succinate, 100 mM Arginine (2 mg/mL) | 6.25 | 6.23 | −0.02 |
| 30 mM Succinate, 100 mM Arginine (8 mg/mL) | 6.25 | 6.23 | −0.02 |
| 30 mM Succinate, 300 mM Arginine (5 mg/mL) Vial A | 6.31 | 6.31 | 0.00 |
| 30 mM Succinate, 300 mM Arginine (5 mg/mL) Vial B | 6.30 | 6.30 | 0.00 |
| 30 mM Succinate, 300 mM Arginine (5 mg/mL) Vial C | 6.30 | 6.29 | −0.01 |
| 30 mM Succinate, 500 mM Arginine (2 mg/mL) | 6.19 | 6.19 | 0.00 |
| 30 mM Succinate, 500 mM Arginine (8 mg/mL) | 6.19 | 6.18 | −0.01 |
| 50 mM Succinate, 100 mM Arginine (5 mg/mL) | 6.18 | 6.17 | −0.01 |
| 50 mM Succinate, 300 mM Arginine (2 mg/mL) | 6.22 | 6.19 | −0.03 |
| 50 mM Succinate, 300 mM Arginine (8 mg/mL) | 6.21 | 6.21 | 0.00 |
| 50 mM Succinate, 600 mM Arginine (5 mg/mL) | 6.22 | 6.21 | −0.01 |
| 10 mM Phosphate, 150 mM NaCl, 0.0033% Tween-20 (w/v) (6 mg/mL)4 | 6.11 | 6.10 | −0.01 |

Changes in SEC aggregate, monomer, and depegylation levels can be analyzed to assess protein stability. Tables 8, 9 and 10 show the compositions of aggregation, monomer, and depegylation in each sample composition, respectively.

TABLE 8

SEC Aggregate Results from DOE #1 Study

| | % Aggregate for Citrate | | | % Aggregate for Succinate | | |
|---|---|---|---|---|---|---|
| Sample | Initial | 40° C. for 1 Day | Difference | Initial | 40° C. for 1 Day | Difference |
| Pre-Dialyze Pool NBJ0801-04-04 for (Buffer) | 1.1 | N/A | | 0.07 | N/A | |
| 10 mM Buffer, 100 mM Arginine (5 mg/mL) | 1.1 | 1.5 | 0.4 | 1.3 | 2.9 | 1.6 |
| 10 mM Buffer, 300 mM Arginine (2 mg/mL) | 1.0 | 1.0 | 0.0 | 1.5 | 1.4 | −0.1 |
| 10 mM Buffer, 300 mM Arginine (8 mg/mL) | 1.0 | 1.2 | 0.2 | 1.2 | 1.4 | 0.3 |
| 10 mM Buffer, 500 mM Arginine (5 mg/mL) | 1.1 | 1.3 | 0.2 | 1.1 | 1.4 | 0.2 |
| 30 mM Buffer, 100 mM Arginine (2 mg/mL) | 1.2 | 1.3 | 0.0 | 1.6 | 1.7 | 0.1 |
| 30 mM Buffer, 100 mM Arginine (8 mg/mL) | 1.1 | 1.5 | 0.4 | 1.2 | 2.6 | 1.3 |
| 30 mM Buffer, 300 mM Arginine (5 mg/mL) Vial A | 1.1 | 1.1 | 0.0 | 1.4 | 1.4 | 0.0 |
| 30 mM Buffer, 300 mM Arginine (5 mg/mL) Vial B | 1.0 | 1.2 | 0.2 | 1.2 | 1.5 | 0.3 |
| 30 mM Buffer, 300 mM Arginine (5 mg/mL) Vial C | 1.0 | 1.1 | 0.1 | 1.2 | 1.4 | 0.2 |
| 30 mM Buffer, 500 mM Arginine (2 mg/mL) | 1.1 | 1.2 | 0.1 | 1.9 | 1.4 | −0.5 |
| 30 mM Buffer, 500 mM Arginine (8 mg/mL) | 1.1 | 1.3 | 0.2 | 1.3 | 1.4 | 0.1 |
| 50 mM Buffer, 100 mM Arginine (5 mg/mL) | 1.3 | 1.5 | 0.2 | 1.5 | 2.7 | 1.3 |
| 50 mM Buffer, 300 mM Arginine (2 mg/mL) | 1.2 | 1.1 | −0.1 | 1.6 | 1.4 | −0.2 |
| 50 mM Buffer, 300 mM Arginine (8 mg/mL) | 1.1 | 1.4 | 0.3 | 1.3 | 1.8 | 0.5 |
| 50 mM Buffer, 500 mM Arginine (5 mg/mL) | 1.4 | 1.2 | −0.2 | 1.4 | 1.4 | 0.0 |
| 10 mM Phosphate, 150 mM NaCl, 0.0033% Tween-20 (5 mg/mL) | Initial = 0.8 | | | 40° C. for 1 Day = 3.7 | | Difference = 2.8 |

TABLE 9

SEC Monomer Results from DOE #1 Study

| | % Monomer for Citrate | | | % Monomer for Succinate | | |
|---|---|---|---|---|---|---|
| Sample | Initial | 40° C. for 1 Day | Difference | Initial | 40° C. for 1 Day | Difference |
| Pre-Dialyze Pool NBJ0801-04-04 for (Buffer) | 98.7 | N/A | | 99.0 | N/A | |
| 10 mM Buffer, 100 mM Arginine (5 mg/mL) | 98.8 | 98.4 | −0.4 | 97.9 | 96.6 | −1.4 |
| 10 mM Buffer, 300 mM Arginine (2 mg/mL) | 98.8 | 98.7 | −0.1 | 97.9 | 98.0 | 0.2 |
| 10 mM Buffer, 300 mM Arginine (8 mg/mL) | 98.9 | 98.6 | −0.3 | 97.8 | 97.7 | −0.1 |
| 10 mM Buffer, 500 mM Arginine (5 mg/mL) | 98.7 | 98.4 | −0.3 | 97.9 | 97.8 | −0.1 |
| 30 mM Buffer, 100 mM Arginine (2 mg/mL) | 98.6 | 98.5 | −0.1 | 98.0 | 97.9 | −0.1 |
| 30 mM Buffer, 100 mM Arginine (8 mg/mL) | 98.7 | 98.3 | −0.4 | 98.1 | 96.9 | −1.2 |
| 30 mM Buffer, 300 mM Arginine (5 mg/mL) Vial A | 98.7 | 98.6 | −0.1 | 98.0 | 98.1 | 0.1 |
| 30 mM Buffer, 300 mM Arginine (5 mg/mL) Vial B | 98.8 | 98.5 | −0.2 | 98.2 | 98.0 | −0.2 |
| 30 mM Buffer, 300 mM Arginine (5 mg/mL) Vial C | 98.8 | 98.6 | −0.2 | 98.2 | 98.1 | −0.1 |
| 30 mM Buffer, 500 mM Arginine (2 mg/mL) | 98.7 | 98.5 | −0.2 | 97.6 | 98.1 | 0.4 |
| 30 mM Buffer, 500 mM Arginine (8 mg/mL) | 98.7 | 98.4 | −0.3 | 98.0 | 98.0 | 0.0 |
| 50 mM Buffer, 100 mM Arginine (5 mg/mL) | 98.5 | 98.3 | −0.2 | 98.1 | 96.9 | −1.2 |
| 50 mM Buffer, 300 mM Arginine (2 mg/mL) | 98.6 | 98.6 | 0.0 | 97.9 | 98.2 | 0.2 |
| 50 mM Buffer, 300 mM Arginine (8 mg/mL) | 98.7 | 98.3 | −0.3 | 98.1 | 97.7 | −0.4 |
| 50 mM Buffer, 500 mM Arginine (5 mg/mL) | 98.4 | 98.5 | 0.1 | 98.0 | 98.0 | 0.0 |
| 10 mM Phosphate, 150 mM NaCl, 0.0033% Tween-20 (5 mg/mL) | Initial = 98.1 | | | 40° C. for 1 Day = 95.6 | | Difference = −2.5 |

TABLE 10

SEC Depegylation Results from DOE #1 Study

| | % Depegylation for Citrate | | | % Depegylation for Succinate | | |
|---|---|---|---|---|---|---|
| Sample | Initial | 40° C. for 1 Day | Difference | Initial | 40° C. for 1 Day | Difference |
| Pre-Dialyze Pool NBJ0801-04-04 for (Buffer) | 0.2 | N/A | | 0.3 | N/A | |
| 10 mM Buffer, 100 mM Arginine (5 mg/mL) | 0.2 | 0.1 | 0.0 | 0.8 | 0.6 | −0.3 |
| 10 mM Buffer, 300 mM Arginine (2 mg/mL) | 0.2 | 0.3 | 0.1 | 0.6 | 0.6 | 0.0 |

TABLE 10-continued

SEC Depegylation Results from DOE #1 Study

| | % Depegylation for Citrate | | | % Depegylation for Succinate | | |
|---|---|---|---|---|---|---|
| Sample | Initial | 40° C. for 1 Day | Difference | Initial | 40° C. for 1 Day | Difference |
| 10 mM Buffer, 300 mM Arginine (8 mg/mL) | 0.2 | 0.3 | 0.1 | 1.0 | 0.8 | −0.2 |
| 10 mM Buffer, 500 mM Arginine (5 mg/mL) | 0.2 | 0.3 | 0.1 | 1.0 | 0.8 | −0.1 |
| 30 mM Buffer, 100 mM Arginine (2 mg/mL) | 0.2 | 0.2 | 0.0 | 0.4 | 0.4 | 0.0 |
| 30 mM Buffer, 100 mM Arginine (8 mg/mL) | 0.2 | 0.2 | 0.0 | 0.6 | 0.5 | −0.1 |
| 30 mM Buffer, 300 mM Arginine (5 mg/mL) Vial A | 0.2 | 0.3 | 0.1 | 0.6 | 0.5 | −0.1 |
| 30 mM Buffer, 300 mM Arginine (5 mg/mL) Vial B | 0.2 | 0.3 | 0.1 | 0.6 | 0.5 | −0.1 |
| 30 mM Buffer, 300 mM Arginine (5 mg/mL) Vial C | 0.2 | 0.2 | 0.0 | 0.6 | 0.5 | 0.0 |
| 30 mM Buffer, 500 mM Arginine (2 mg/mL) | 0.2 | 0.3 | 0.1 | 0.5 | 0.5 | 0.0 |
| 30 mM Buffer, 500 mM Arginine (8 mg/mL) | 0.2 | 0.3 | 0.1 | 0.7 | 0.7 | −0.1 |
| 50 mM Buffer, 100 mM Arginine (5 mg/mL) | 0.2 | 0.2 | 0.0 | 0.4 | 0.4 | −0.1 |
| 50 mM Buffer, 300 mM Arginine (2 mg/mL) | 0.2 | 0.3 | 0.1 | 0.4 | 0.4 | 0.0 |
| 50 mM Buffer, 300 mM Arginine (8 mg/mL) | 0.2 | 0.2 | 0.0 | 0.6 | 0.6 | −0.1 |
| 50 mM Buffer, 500 mM Arginine (5 mg/mL) | 0.2 | 0.3 | 0.1 | 0.6 | 0.6 | 0.0 |
| 10 mM Phosphate, 150 mM NaCl, 0.0033% Tween-20 (5 mg/mL) | Initial = 1.1 | | | 40° C. for 1 Day = 0.7 | | Difference = −0.3 |

The SEC results indicate that the aggregate level in citrate samples is relatively unchanged. Succinate samples also have low aggregate levels except for samples with 100 mM arginine, suggesting that succinate-based buffers would require more than 100 mM arginine to maintain low protein aggregation. The control condition (10 mM Phosphate, 150 mM NaCl, and 0.0033% (w/v) polyoxyethylene (20) sorbitan monolaurate at pH 6 and at 5 mg/mL) have 3.7% aggregate after one day incubation at 40° C. (see Table 8).

Depegylation is another protein degradation pathway. Table 10 shows SEC results for depegylated product and indicates that the depegylation level in succinate samples is higher (0.4%-0.8%) than those in citrate samples (≤0.3%). The depegylation level in the phosphate control is higher than all citrate formulation samples and is slightly higher than most succinate formulations.

Since SEC results for citrate samples incubated at 40° C. for one day have minimal aggregate, a subset of the DOE #1 samples can be incubated at 25° C. for 28 days. The following sample conditions can be analyzed by SEC:

1. 30 mM Citrate, 100 mM Arginine at 2 mg/mL
2. 30 mM Citrate, 500 mM Arginine at 2 mg/mL
3. 30 mM Citrate, 100 mM Arginine at 8 mg/mL
4. 30 mM Citrate, 500 mM Arginine at 8 mg/mL
5. 30 mM Citrate, 300 mM Arginine at 5 mg/mL Table 11 shows the SEC results of the 28 day experiment. Moreover, analysis by RP-HPLC can be performed on the samples incubated at 28 days to ensure lack of product degradation. Table 12 shows these results.

TABLE 11

SEC Results from DOE #1 Study Incubated 28 days at 25° C.

| | 28-Day Incubation at 25° C. | | |
|---|---|---|---|
| Sample | Avg % Aggregate | Avg % PEG-bGCSF | Avg % bGCSF |
| 100 mM Arginine 2 mg/mL | 1.3 | 98.1 | 0.6 |
| 100 mM Arginine 8 mg/mL | 1.6 | 98.0 | 0.4 |
| 300 mM Arginine 5 mg/mL Vial A | 1.4 | 98.0 | 0.7 |
| 300 mM Arginine 5 mg/mL Vial B | 1.3 | 98.1 | 0.6 |
| 300 mM Arginine 5 mg/mL Vial C | 1.3 | 98.0 | 0.7 |
| 500 mM Arginine 2 mg/mL | 1.4 | 97.8 | 0.8 |
| 500 mM Arginine 8 mg/mL | 1.5 | 97.7 | 0.7 |

TABLE 12

RP-HPLC Results from DOE #1 Study Incubated 28 days at 25° C.

| | % Monomer | | |
|---|---|---|---|
| Sample | Initial | 28 Day at 25° C. | Difference |
| 100 mM Arginine 2 mg/mL | 97.3 | 97.8 | 0.4 |
| 100 mM Arginine 8 mg/mL | 97.0 | 97.4 | 0.4 |
| 300 mM Arginine 5 mg/mL Vial A | 97.3 | 97.3 | 0.0 |
| 300 mM Arginine 5 mg/mL Vial B | 97.1 | 95.2 | −2.0 |
| 300 mM Arginine 5 mg/mL Vial C | 97.1 | 97.4 | 0.3 |
| 500 mM Arginine 2 mg/mL | 97.2 | 97.0 | −0.2 |
| 500 mM Arginine 8 mg/mL | 97.2 | 97.2 | 0.0 |

EXAMPLE 4

Counter Ion and Syringe Compatibility Evaluation

A comparison of chloride and sulfate as counter ions for arginine can be evaluated. The sample condition can be 30 mM citrate and 300 mM arginine at 5 mg/mL (pH 6). In addition, product compatibility in MONOJECT 3 mL polypropylene syringe for containing the drug product can be compared to 1 mL glass vials. The 30 mM citrate, 300 mM arginine pH 6 (Chloride) buffer can be prepared using sodium citrate and arginine-HCl, and the solution can be titrated with 6N HCl. The 30 mM citrate, 300 mM arginine pH 6 (Sulfate) buffer can be prepared using citric acid monohydrate, sodium citrate, and arginine base, and the solution can be titrated with concentrated sulfuric acid. bGCSFT133-20K PEG can be dialyzed into the two buffers.

Samples can be analyzed by SEC at time zero. One set of samples can be placed in 1 mL glass lyophilization vial and a second in 3 mL syringes prior to incubation at 40° C. for up to 3 days.

Table 13 shows SEC results. The SEC results indicate that aggregate formation is two to three times higher in samples stored in syringes than in glass vials. Product depegylation remains the same as the time zero samples. For both counter ions, samples in glass vials have minimal change in aggregate after 3 days at 40° C. Chloride could be used in place of sulfate as a counter ion without impact on aggregate formation.

TABLE 13

SEC Results from the Counter Ion and Syringe Compatibility Evaluation

| | Initial | | | 1-Day Incubation at 40° C. | | | 2-Day Incubation at 40° C. | | | 3-Day Incubation at 40° C. | | |
|---|---|---|---|---|---|---|---|---|---|---|---|---|
| Sample | % Aggregate | % PEG-bGCSG | % bGCSF | % Aggregate | % PEG-bGCSG | % bGCSF | % Aggregate | % PEG-bGCSG | % bGCSF | % Aggregate | % PEG-bGCSG | % bGCSF |
| Pre-dialyzed Pool | 0.5 | 99.2 | 0.3 | | | | N/A | | | | | |
| Chloride (Glass Vial) | 1.2 | 98.5 | 0.3 | 1.2 | 98.5 | 0.4 | 1.2 | 98.3 | 0.4 | 1.2 | 98.2 | 0.7 |
| Sulfate (Glass Vial) | 1.6 | 98.1 | 0.3 | 1.2 | 98.5 | 0.3 | 1.2 | 98.3 | 0.5 | 1.4 | 97.9 | 0.6 |
| Chloride (Syringes) | 1.2 | 98.5 | 0.3 | 2.2 | 97.5 | 0.3 | 4.0 | 95.5 | 0.4 | 4.9 | 94.6 | 0.5 |
| Sulfate (Syringe) | 1.6 | 98.1 | 0.3 | 2.1 | 97.5 | 0.3 | 3.5 | 96.1 | 0.4 | 4.5 | 95.0 | 0.5 |

EXAMPLE 5

Three Parameter, 2-Level Full Factorial (DOE #2)

A second DOE study can be performed to evaluate the effect of pH, arginine concentration, and protein concentration in citrate buffer. Table 14 shows the formulation conditions used in DOE #2.

TABLE 14

Formulation Conditions Used for the DOE #2 Study

| Sample No. | Arginine Concentration (mM) | pH | Product Concentration (mg/mL) |
|---|---|---|---|
| 1 | 200 | 5.0 | 2 |
| 2 | 200 | 6.0 | 8 |
| 3 | 200 | 6.0 | 2 |
| 4 | 200 | 6.0 | 8 |
| 5 | 250 | 5.5 | 5 |
| 6 | 250 | 5.6 | 5 |
| 7 | 250 | 6.5 | 5 |
| 8 | 300 | 5.0 | 6 |
| 9 | 300 | 6.0 | 2 |
| 10 | 300 | 6.0 | 8 |
| 11 | 300 | 6.0 | 2 | bGCSF-T133-20K PEG can be dialyzed into 5 buffer conditions. Samples 1 and 2 can be dialyzed in a buffer containing 30 mM citrate and 200 mM arginine at pH 5.0. Samples 3 and 4 can be dialyzed in a buffer containing 30 mM citrate and 200 mM arginine at pH 5.0. Samples 5 and 6 can be dialyzed in a buffer containing 30 mM citrate and 250 mM arginine at pH 6.0. Samples 7 and 8 can be dialyzed in a buffer containing 30 mM citrate and 300 mM arginine at pH 6.0. Samples 9 and 10 can be dialyzed in a buffer containing 30 mM citrate and 300 mM arginine at pH 5.5. Each post-dialyzed sample can be adjusted to the final target product concentration and then divided into 2×1 mL aliquots in glass lyophilization vials to form two sets of samples: one set can be stored at 2-8° C. as controls and a second set can be stored at 40° C. for three days.

Table 15 shows SEC results. The change in aggregate is between −0.1% and 2.1%. Higher aggregate strongly correlates with higher product concentration. Delta depegylation is between 0.1% and 0.8%. Slightly higher depegylation correlates with low product concentration at low pH. As pH decreases, depegylation increases, and this trend is consistent with historical observations in the pre-formulation studies.

TABLE 15

Summary of SEC Results for DOE #2 Study

| | % Aggregate | | | % Monomer | | | % Depegylation | | |
|---|---|---|---|---|---|---|---|---|---|
| Run # | Initial | 40° C. for 3 Day | Difference | Initial | 40° C. for 3 Day | Difference | Initial | 40° C. for 3 Day | Difference |
| 1 | 1.0 | 1.2 | 0.2 | 98.7 | 97.8 | −0.9 | 0.3 | 1.0 | 0.7 |
| 2 | 0.8 | 2.8 | 2.0 | 98.9 | 96.6 | −2.3 | 0.3 | 0.7 | 0.4 |
| 3 | 1.4 | 1.3 | −0.1 | 98.4 | 98.3 | −0.1 | 0.2 | 0.4 | 0.2 |
| 4 | 0.9 | 2.6 | 1.7 | 98.8 | 97.1 | −1.8 | 0.2 | 0.3 | 0.1 |
| 5 | 0.9 | 2.0 | 1.1 | 98.8 | 97.4 | −1.4 | 0.3 | 0.6 | 0.3 |
| 6 | 1.0 | 2.0 | 1.0 | 98.7 | 97.4 | −1.3 | 0.3 | 0.6 | 0.3 |
| 7 | 1.0 | 1.8 | 0.8 | 98.8 | 97.7 | −1.1 | 0.3 | 0.6 | 0.3 |
| 8 | 1.1 | 1.2 | 0.1 | 98.6 | 97.7 | −0.9 | 0.3 | 1.1 | 0.8 |

TABLE 15-continued

Summary of SEC Results for DOE #2 Study

| | % Aggregate | | | % Monomer | | | % Depegylation | | |
|---|---|---|---|---|---|---|---|---|---|
| Run # | Initial | 40° C. for 3 Day | Difference | Initial | 40° C. for 3 Day | Difference | Initial | 40° C. for 3 Day | Difference |
| 9 | 0.7 | 2.8 | 2.1 | 99.0 | 96.4 | −2.6 | 0.3 | 0.8 | 0.5 |
| 10 | 1.2 | 1.2 | 0.0 | 98.6 | 98.4 | −0.2 | 0.2 | 0.5 | 0.2 |
| 11 | 0.9 | 2.2 | 1.3 | 98.8 | 97.3 | −1.5 | 0.3 | 0.4 | 0.1 |

EXAMPLE 6

Agitation Study

A forced agitation study can be performed to assess protein stability in the formulations. The samples can be prepared by dialyzing bGCSF-T133-20K PEG (16.6 mg/mL protein in 10 mM sodium acetate, 5% sorbitol pH 4.0) against 30 mM Citrate and 250 mM Arginine at pH 6.0. A portion of the dialyzed material can be diluted to a target concentration of 5 mg/mL using buffer 30 mM Citrate and 250 mM Arginine at pH 6.0. The pool cans then be filtered through a 0.22 micron filter and then be subjected to forced agitation in a glass beaker by mixing at 60 rpm using a magnetic stirrer for two hours at room temperature. Samples can be taken every 30 minutes.

All samples are clear, colorless, and free of visible particulates for all timepoints. The protein concentration, absorbance at 550 nm, and pH measurement for each timepoint are shown in Table 16.

TABLE 16

Summary of Protein Concentration, $A_{550}$, and pH Results from the Agitation (Mixing) Study

| | A280 nm Assay | | | | |
|---|---|---|---|---|---|
| Sample | Protein Concentration (mg/mL) | Std. Dev. (%) | RSD (%) | A550 Absorbance | pH |
| $T_0$ | 4.9 | 0.03 | 0.60% | 0.00942 | 6.0 |
| $T_{30min}$ Control | 5.0 | 0.01 | 0.30% | −0.00015 | 6.0 |
| $T_{30min}$ Agitated | 4.9 | 0.04 | 0.70% | 0.00972 | 6.0 |
| $T_{60min}$ Control | 4.9 | 0.03 | 0.60% | 0.00407 | 6.0 |
| $T_{60min}$ Agitated | 4.9 | 0.02 | 0.40% | 0.03547 | 6.0 |
| $T_{90min}$ Control | 5.0 | 0.05 | 1.00% | 0.09031 | 6.0 |
| $T_{90min}$ Agitated | 4.9 | 0.03 | 0.60% | 0.08798 | 6.0 |
| $T_{120min}$ Control | 5.0 | 0.03 | 0.60% | 0.08761 | 6.0 |
| $T_{120min}$ Agitated | 4.9 | 0.03 | 0.60% | 0.08775 | 6.0 |

The protein concentration remains stable throughout the mixing duration. The pH remains consistent throughout the experiment. Product composition by SEC is also consistent throughout the study, as shown in Table 17. Overall, results from this study indicate that the protein is stable for the entire duration of forced agitation.

TABLE 17

Summary of SEC Results from the Agitation (Mixing) Study

| Sample | % Aggregate | % PEG-bGCSF | % bGCSF |
|---|---|---|---|
| $T_0$ | 1.6 | 98.1 | 0.3 |
| $T_{30\,min}$ Control | 1.6 | 98.2 | 0.3 |
| $T_{30\,min}$ Agitated | 1.6 | 98.2 | 0.3 |
| $T_{60\,min}$ Control | 1.6 | 98.1 | 0.3 |

TABLE 17-continued

Summary of SEC Results from the Agitation (Mixing) Study

| Sample | % Aggregate | % PEG-bGCSF | % bGCSF |
|---|---|---|---|
| $T_{60\,min}$ Agitated | 1.6 | 98.2 | 0.3 |
| $T_{90\,min}$ Control | 1.6 | 98.2 | 0.3 |
| $T_{90\,min}$ Agitated | 1.6 | 98.2 | 0.3 |
| $T_{120\,min}$ Control | 1.6 | 98.1 | 0.3 |
| $T_{120\,min}$ Agitated | 1.6 | 98.2 | 0.3 |

EXAMPLE 7

Freeze-Thaw Study

A freeze-thaw study can be performed to determine protein concentration and pH of various samples. Protein in the samples can be subjected up to five freeze and thaw cycles. Samples can be filtered through 0.22 micron filters and dispensed into 15 mL vials. One aliquot can be set aside as the control. For the remaining three aliquots, each freeze-thaw cycle could consist of freezing the protein solution for one hour at −75±5° C. and thawing at room temperature for approximately one hour until no ice is observed. The sample vial can be gently swirled three times to mix the sample. One aliquot can be set aside after the first, second, and fifth freeze and thaw cycles for testing.

All samples are clear, colorless, and free of visible particulates for all timepoints. The protein concentration, absorbance at 550 nm, and pH measurement for each timepoint are shown in Table 18.

TABLE 18

Summary of Protein Concentration, $A_{550}$, and pH Results from the Freeze-Thaw Study

| | A280 nm Assay | | | | |
|---|---|---|---|---|---|
| Sample | Protein Concentration (mg/mL) | Std. Dev. (%) | RSD (%) | A550 Absorbance | pH |
| Cycle 0 | 20.6 | 0.5 | 2.20% | 0.11563 | 5.9 |
| Cycle 1 | 21.9 | 1.4 | 6.40% | 0.09471 | 5.9 |
| Cycle 2 | 22.6 | 0.3 | 1.40% | 0.12685 | 5.9 |
| Cycle 5 | 21.3 | 1.0 | 4.60% | 0.13357 | 5.9 |

The protein concentration remains stable after each freeze-thaw cycle. Furthermore, the pH remains consistent throughout the five freeze-thaw cycles. Product composition by SEC is similar across all timepoints and is shown in Table 19.

TABLE 19

Summary of SEC Results from the Freeze-Thaw Study

| Sample | % Aggregate | % PEG-bGCSF | % bGCSF |
|---|---|---|---|
| Cycle 0 | 1.6 | 98.1 | 0.3 |
| Cycle 1 | 1.5 | 98.1 | 0.4 |
| Cycle 2 | 1.6 | 98.0 | 0.4 |
| Cycle 5 | 1.5 | 98.1 | 0.4 |

INCORPORATION OF SEQUENCE LISTING

Incorporated herein by reference in its entirety is the Sequence Listing for the above-identified Application. The Sequence Listing is disclosed on a computer-readable ASCII text file titled "Sequence_Listing_2848-22_CON.txt", created on Feb. 2, 2022. The sequence.txt file is 24 KB in size.

What is claimed is:

1. A stable aqueous formulation comprising
   (a) a bovine granulocyte colony stimulating factor (bG-CSF) polypeptide of SEQ IDS NO: 1 or SEQ ID NO: 2 comprising a non-naturally encoded amino acid substituted at position 133 of SEQ ID NO: 1 or the corresponding amino acid in SEQ ID NO: 2 wherein the non-naturally encoded amino acid is para-acetylphenylalanine, wherein said para-acetylphenylalanine is bonded to a water soluble polymer being a poly(ethylene) glycol moiety;
   (b) a citrate buffer;
   (c) arginine, and optionally a counter ion for arginine;
   (d) wherein pH of the formulation ranges from 5.7 to 6.6.

2. The formulation of claim 1 wherein the formulation is substantially free of a polysorbate surfactant.

3. The formulation of claim 1 wherein the water soluble polymer has a molecular weight of about 20 kDa.

4. The formulation of claim 2 wherein said polysorbate surfactant is a polyoxyethylene derivative of sodium monolaurate.

5. The formulation of claim 2 wherein said polysorbate surfactant is polyoxyethylene (20) sorbitan monolaurate.

6. The formulation of claim 1 wherein the counter ion for arginine is chloride or sulfate.

7. The formulation of claim 1 optionally comprising one or more other therapeutic ingredients.

8. A lyophillisate or powder of the formulation of claim 1.

9. A process for preparing the formulation of claim 1 comprising a stable aqueous solution comprising said bG-CSF polypeptide, a citrate buffer, arginine, and optionally a counter ion for arginine.

10. The formulation of claim 1 wherein said citrate buffer has a molarity of about 30 mM.

11. The formulation of claim 1 wherein said arginine has a molarity of about 250 mM.

12. The formulation of claim 1 wherein said arginine has a molarity of about 200 to about 300 mM.

13. The formulation of claim 1 wherein the pH ranges from 6.0-6.3.

14. The formulation of claim 1 wherein the pH is 6.0±0.1.

* * * * *